(12) United States Patent
Togino

(10) Patent No.: US 7,929,219 B2
(45) Date of Patent: Apr. 19, 2011

(54) OPTICAL ELEMENT, OPTICAL SYSTEM AND ENDOSCOPE USING THE SAME

(75) Inventor: Takayoshi Togino, Koganei (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/653,257

(22) Filed: Dec. 9, 2009

(65) Prior Publication Data

US 2010/0091385 A1    Apr. 15, 2010

Related U.S. Application Data

(63) Continuation of application No. PCT/JP2008/060816, filed on Jun. 6, 2008.

(30) Foreign Application Priority Data

Jun. 12, 2007 (JP) ................................ 2007-155157
Jun. 12, 2007 (JP) ................................ 2007-155159

(51) Int. Cl.
    *G02B 17/00* (2006.01)
(52) U.S. Cl. ........................................ 359/736; 359/726
(58) Field of Classification Search .......... 359/726–736, 359/754–795; 600/101–183
    See application file for complete search history.

(56) References Cited

U.S. PATENT DOCUMENTS

| 5,930,055 A * | 7/1999 | Eisenberg ...................... 359/728 |
| 6,449,103 B1 | 9/2002 | Charles |
| 2004/0254424 A1 | 12/2004 | Simkulet et al. |
| 2009/0082629 A1 * | 3/2009 | Dotan et al. .................. 600/160 |

FOREIGN PATENT DOCUMENTS

| JP | 60-042728 | 3/1985 |
| JP | 2001-174713 | 6/2001 |
| JP | 2002-523801 | 7/2002 |
| JP | 2002-341409 | 11/2002 |
| JP | 2006-58412 | 3/2006 |
| JP | 2006-113096 | 4/2006 |
| JP | 2006-126322 | 5/2006 |
| JP | 2006-154364 | 6/2006 |
| JP | 2006-209041 | 8/2006 |
| WO | WO 03-042743 | 5/2003 |
| WO | WO 2005/110186 | 11/2005 |

* cited by examiner

*Primary Examiner* — Darryl J Collins
(74) *Attorney, Agent, or Firm* — Kenyon & Kenyon LLP

(57) ABSTRACT

A flux of light entering a transparent medium proceeds along a side view optical path by way of a first transmissive surface so as to be reflected to the side opposite to an image plane by a first reflective surface and then to the image plane side by a second reflective surface to form an optical path before going out from the transparent medium to the outside at the image plane side by way of a second transmissive surface in the order of forward ray tracing and also along a direct view optical path by way of a third transmissive surface to form another optical path before going out from the transparent medium into the outside at the image plane side by way of a fourth transmissive surface also as viewed in the order of forward ray tracing.

32 Claims, 40 Drawing Sheets

(a)

(b)

(c)

(a)

(b)

OPTICAL ELEMENT, OPTICAL SYSTEM AND ENDOSCOPE USING THE SAME

CROSS-REFERENCE TO RELATED APPLICATIONS

This application is a continuation of International Application No. PCT/JP2008/060816 filed on Jun. 6, 2008, which claims priority to Japanese Application No. 2007-155157 filed on Jun. 12, 2007 and to Japanese Patent Application No. 2007-155159 filed on Jun. 12, 2007, each of which is expressly incorporated herein in its entirety by reference thereto.

BACKGROUND OF THE INVENTION AND RELATED ART STATEMENT

The present invention relates to an optical element, an optical system having such an optical element and an endoscope using such an optical system. More particularly, the present invention relates to an optical element having two optical paths and designed to synthetically combine the image on the axis of rotational symmetry thereof and the two optical paths that are substantially orthogonal to the axis of rotational symmetry and also to an image formation optical system or a projection optical system having such an optical element and includes a function of forming circular and annular images on a single imaging element.

Patent Document 1 listed below describes a known image pickup optical system having a refraction optical system, a reflection optical system and an image formation optical system arranged therein along with two optical paths so as to be capable of picking up a panoramic image and an axial image. Patent Document 2 describes a known endoscope similarly having two optical paths. Furthermore, Patent Document 3 describes a known endoscope by means of which it is possible to omni-directionally observe the surroundings and Patent Document 4 describes a known capsule endoscope by means of which it is also possible to omni-directionally observe the surroundings. Finally, Patent Document 5 describes an image pickup device that can shoot omni-directionally the surroundings and also only forward at the same time.

[Patent Document 1] Jpn. PCT National Publication No. 2003-042743
[Patent Document 2] U.S. Patent Application Publication No. 2004-0254424
[Patent Document 3] JP-A-60-42728
[Patent Document 4] JP-A-2001-174713
[Patent Document 5] JP-A-2002-341409

SUMMARY OF THE INVENTION

In an aspect of the present invention, an optical element rotationally symmetric around a central axis is formed by a transparent medium having a refractive index greater than 1, wherein the transparent medium has a first transmissive surface, a first reflective surface arranged at the side of the central axis thereof relative to the first transmissive surface, a second reflective surface arranged at the side opposite to the image plane relative to the first reflective surface, a second transmissive surface arranged at the image plane side relative to the second reflective surface, a third transmissive surface and a fourth transmissive surface arranged at the image plane side relative to the third transmissive surface, that the flux of light entering the transparent medium has a side view optical path and a direct view optical path therein and goes into the transparent medium to proceed along the side view optical path by way of the first transmissive surface so as to be reflected to the side opposite to the image plane by the first reflective surface and then to the image plane side by the second reflective surface to form an optical path before going out from the transparent medium to the outside at the image plane side by way of the second transparent surface in the order of forward ray tracing and also along the direct view optical path by way of the third transmissive surface to form another optical path before going out from the transparent medium into the outside at the image plane side by way of the fourth transmissive surface also as viewed in the order of forward ray tracing.

Preferably, the side view optical path is formed a substantially Z-shaped optical path.

Preferably, the side view optical path is formed only at a side relative to the central axis.

Preferably, the second transmissive surface is arranged in the vicinity of the central axis and the first reflective surface and the second reflective surface are arranged in a peripheral part thereof, while the first transmissive surface is arranged in the outermost peripheral part thereof.

Preferably, the first reflective surface is a surface arranged at a position same as that of and having a shape same as that of the second transmissive surface.

Preferably, the first reflective surface is a surface arranged at a position same as that of and having a shape same as that of the fourth transmissive surface.

Preferably, the second reflective surface is a surface arranged at a position same as that of and having a shape same as that of the third transmissive surface.

Preferably, the first reflective surface and the second reflective surface have a total reflection effect.

Preferably, the first transmissive surface is a cylindrical or conical surface.

Preferably, at least either the first reflective surface and the second reflective surface is formed by an extended rotary free curved surface formed by rotating a line segment of arbitrary shape having no plane of symmetry around the central axis.

Preferably, at least one of the surfaces that the transparent medium has is formed by an extended rotary free curved surface formed by rotating a line segment of arbitrary shape including one or more than one odd-number-th degree terms.

In another aspect of the present invention, an optical system includes a front group, a back group arranged at the side of the image plane relative to the front group and an aperture arranged between the front group and the back group and that optical elements are arranged in the front group and the direct view optical path picks up or projects an image of an object point in the vicinity of the central axis while the side view optical path picks up or projects an image of an object point on the periphery of the central axis.

Preferably, the side view optical path and the direct view optical path share part of the optical elements for use and a circular image of the direct view optical path and an annular image of the side view optical path on the outer periphery thereof are formed on the same plane.

Preferably, the second reflective surface is arranged with its concave surface directed to the aperture.

Preferably, the first reflective surface is arranged with its concave surface directed to the aperture.

Preferably, the image of the side view optical path does not form any intermediate image on the optical path.

Preferably, an optical system as defined above is further wherein it satisfies the condition of $$D < 100 \text{ m} \tag{1},$$

where D is the external dimension of the optical element.

Preferably, an optical system as defined above is further wherein it satisfies the condition of $$D/Dr<2 \qquad (2),$$

where Dr is the external dimension of the image of the side view optical path.

In another aspect of the present invention, an optical system rotationally symmetric relative to the central axis thereof and having a front group with negative power, an aperture and a back group with positive power to form or project an image without forming an intermediate image on any optical path, wherein the front group has an effect of synthetically combining a direct view optical path for forming or projecting an image on the central axis by a transmission effect and a side view optical path for forming or projecting an omni-directional image in a direction substantially orthogonal to the central axis by a reflection effect, that the optical system includes a transparent medium having a first transmissive surface arranged opposite to and outside an object surface, a first reflective surface arranged at the central axis side relative to the first transmissive surface, a second reflective surface arranged at the side opposite to an image plane relative to the first reflective surface, a second transmissive surface arranged at the image plane side relative to the second reflective surface, a third transmissive surface and a fourth transmissive surface arranged at the image plane side relative to the third transmissive surface, that the flux of light entering the front group enters the transparent medium by way of the first transmissive surface to proceed along the side view optical path so as to be reflected to the side opposite to the image plane by the first reflective surface and then to the image plane side by the second reflective surface to form an optical path before going out from the transparent medium to the outside at the image plane side by way of the second transparent surface in the order of forward ray tracing and also along the direct view optical path by way of the third transmissive surface before going out from the transparent medium into the outside at the image plane side by way of the fourth transmissive surface also as viewed in the order of forward ray tracing and that, if the ray of light passing through the center of the aperture is referred to as central principal ray of light, the central principal ray of light striking the first transparent surface is inclined toward the image plane side relative to a line orthogonal to the central axis.

Preferably, the side view optical path is formed a substantially Z-shaped optical path.

Preferably, the first reflective surface and the second reflective surface are arranged with their concave surfaces directed to the aperture and, if the center of the view angle of the meridional cross section of an omni-directional image is referred to as the central view angle and the ray of light passing through the center of the aperture is referred to as a central principal ray of light, the position at which the central principal ray of light strikes the first reflective surface is located at the side opposite to the image plane relative to the aperture.

Preferably, the first reflective surface has a total reflection effect.

Preferably, a transmissive surface is arranged at the side opposite to the image plane relative to the first reflective surface, and that the first reflective surface and the second transmissive surface are formed at the same position with the same surface shape.

Preferably, the first reflective surface and the fourth transmissive surface are formed at the same position with the same surface shape.

Preferably, the second reflective surface and the third transmissive surface are formed at the same position with the same surface shape.

Preferably, the optical path from the first reflective surface to the second reflective surface is in a direction divergent relative to the central axis.

Preferably, at least one of the surfaces that the front group has is formed by an extended rotary free curved surface formed by rotating a line segment of arbitrary shape having no plane of symmetry around the central axis.

Preferably, at least one of the surfaces that the front group has is formed by a rotary free curved surface formed by rotating a line segment of arbitrary shape including one or more than one odd-number-th degree terms.

In another aspect of the present invention, an endoscope is formed by using an optical system as defined above.

DETAILED DESCRIPTION OF PREFERRED EMBODIMENTS

Now, an optical element and an optical system including such an optical element according to the present invention will be described below based on examples.

Figure 3:
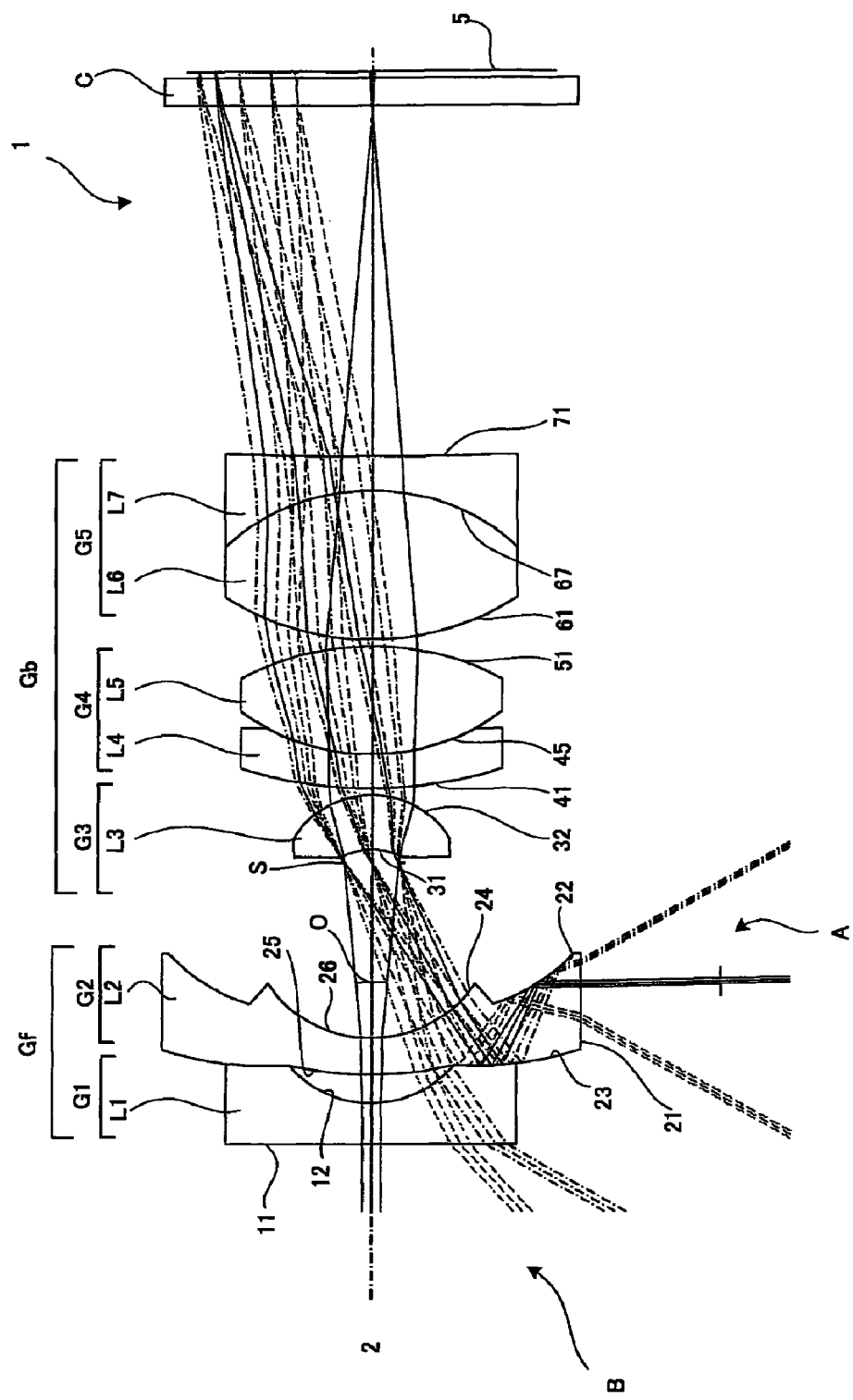
FIG. 3 is a schematic cross sectional view of the optical system of Example 1 of the present invention taken along the central axis thereof.

FIG. 3 is a schematic cross sectional view of the optical system 1 of Example 1 of the present invention, which will be described in greater detail hereinafter, taken along the central axis (axis of rotational symmetry) 2 thereof. Note that, while the optical system is described below in terms of image formation optical system, it is also applicable to a projection optical system by using the optical path reversely.

The optical system 1 of the present invention includes a front group Gf that is rotationally symmetric relative to central axis 2 and has negative power, an aperture S and a back group Gb having positive power and can form or project an image without forming an intermediate image on any optical path.

The optical system 1 of Example 1 includes a front group Gf that is rotationally symmetric relative to central axis 2 and a back group Gb that is also rotationally symmetric relative to the central axis 2. The front group Gf of the optical system is formed by a first group G1 having negative power and a second group G2 that is an optical path synthesizing optical system and the back group Gb if the optical system arranged at the back of the aperture S is formed by a third group G3 having positive power, a fourth group G4 and a fifth group G5 that are cemented lenses having positive power.

In this example, the second group G2 of the front group has a side view optical path A and a direct view optical path B and the third group G3, the fourth group G4 and the fifth group G5 of the back group Gb have an effect of forming the aerial image synthesized by the second group G2. It operates to form a circle for the image at the image center on the central axis 2 by means of the direct view optical path B and a different annular image of the side view optical path A at the outside of the circle.

Therefore, the embodiment of the present invention provides a compact and inexpensive optical element that has a simple configuration and forms both an image of an object point and an omni-directional image in a direction substantially orthogonal to the central axis on a single imaging element at the same time, an optical system having such an optical element and also an endoscope using such an optical system.

Thus, the embodiment of the present invention provides a compact optical system having a simple configuration and excellent resolving power for which aberrations are corrected satisfactorily and that can observe or project an image in different directions. Additionally, an optical system according to the embodiment of the present invention can provide a wide view angle for observation at the image plane side relative to a direction orthogonal to the central axis. Still additionally, an optical system according to the embodiment of the present invention can suppress and minimize the comatic aberration and the eccentric aberration. Furthermore, an optical system according to the embodiment of the present invention can be processed in a simple manner and prepared inexpensively. Finally, the pixels of an optical system according to the embodiment of the present invention can be effectively utilized.

The parallel flat plate arranged near the aperture S in each of Example 6 and the succeeding examples typically operates as filter F. The parallel flat plate near the image plane 5 is typically a cover glass C for the imaging element.

The optical system becomes of the so-called retro-focus type when the front group Gf is made negative and the back group is made positive. Such an arrangement is effective particularly when a wide view angle needs to be secured for observation relative to the direct view optical path B for an object point on the central axis 2.

An optical element according to the present invention is made of a transparent medium L2 that is rotationally symmetric around the central axis 2 and has a refractive index not less than 1. The transparent medium L2 has a first transmissive surface 21, a first reflective surface 22 arranged at the side of the central axis 2 thereof relative to the first transmissive surface 21, a second reflective surface 23 arranged at the side opposite to the image plane 5 relative to the first reflective surface 22, a second transmissive surface 24 arranged at the side of the image plane 5 relative to the second reflective surface 23, a third transmissive surface 25 and a fourth transmissive surface 26 arranged at the side of the image plane 5 relative to the third transmissive surface 25 and the flux of light striking the transparent medium L2 has a side view optical path A and a direct view optical path B therein and enters the transparent medium L2 to proceed along the side view optical path A by way of the first transmissive surface 21 so as to be reflected to the side opposite to the image plane 5 by the first reflective surface 22 and then to the side of the image plane 5 by the second reflective surface 23 to form a substantially Z-shaped optical path before going out from the transparent medium L2 to the outside at the side of the image plane 5 by way of the second transparent surface 24 in the order of forward ray tracing and along the direct view optical path B by way of the third transmissive surface 25 before going out from the transparent medium L2 to the outside at side of the image plane 5 by way of the fourth transmissive surface 26.

With this arrangement, the angle of incidence relative to the first reflective surface 22 and the second reflective surface 23 of the side view optical path A can be made relatively small to minimize the eccentric aberration that arises at each of the reflective surfaces. Additionally, the continuity of the image of the central axis 2 and its vicinity of the direct view optical path B for shooting the central axis 2 and its vicinity is secured to make it possible to form a smooth central image.

Additionally, an optical element according to the present invention can be made thin when the side view optical path A is formed only at a side of the central axis because the optical path does not cross the central axis 2 in the optical element.

Still additionally, the side view optical path A can be made to enter an optical element according to the present invention in a direction substantially orthogonal to the central axis 2 and pass through the second transmissive surface 24 after being reflected by the first reflective surface 22 and the second reflective surface 23 when the second transmissive surface 24 is arranged in the vicinity of the central axis 2 and the first reflective surface 22 and the second reflective surface 23 are arranged in a peripheral part thereof, while the first transmissive surface 21 is arranged in the outermost peripheral part thereof. Then, the first reflective surface 22 and the second reflective surface 23 can be arranged as internal reflective surfaces. Thus, it is possible to minimize the eccentric aberration that may arise by using internal reflective surfaces.

Still additionally, the processibility of an optical system according to the present invention can be improved to facilitate the preparation thereof when the first reflective surface 22 is a surface arranged at a position same as that of and having a shape same as that of the second transmissive surface 24 and the first reflective surface 22 is a surface arranged at a position same as that of and having a shape same as that of the fourth transmissive surface 26, while the second reflective surface 23 is a surface arranged at a position same as that of and having a shape same as that of the third transmissive surface 25. Since the flux of light of the direct view optical path B and that of the side view optical path A can be separated from each other with difficulty at a surface at a side of the aperture. Thus, the region between the two images where no image is formed can be minimized by arranging the first reflective surface 22 and the second transmissive surface 24 at the same position and making them have the same shape.

Still additionally, no reflection film needs to be provided to facilitate the preparation of an optical element according to the present invention when the first reflective surface 22 and the second reflective surface 23 are made to have a total reflection effect. Then, the reflectivity can be made equal to 100% at the same time to make it possible to pick up a bright image.

Still additionally, an optical element according to the present invention can be formed as a single and stand-along element to make it advantageous from the viewpoint of preparation when the first transmissive surface 21 is a cylindrical or conical surface.

Still additionally, the distortions at and near the view angle can be corrected when at least either the first reflective surface 22 and the second reflective surface 23 is formed by an extended rotary free curved surface formed by rotating a line segment of arbitrary shape having no plane of symmetry around the central axis 2.

Still additionally, an optical element according to the present invention can be made to have a shape that is vertically asymmetric relative to the center of the view angle to make it advantageous for correcting aberrations when at least one of the surfaces that the transparent medium L2 has is formed by an extended rotary free curved surface formed around the central axis 2 by rotating a line segment of arbitrary shape including one or more than one odd-number-th degree terms.

An optical system according to the present invention includes a front group Gf, a back group Gb arranged at the side of the image plane 5 relative to the front group Gf and an aperture S arranged between the front group and the back group Gb. Optical elements are arranged in the front group Gf and the direct view optical path B picks up or projects an image of an object point in the vicinity of the central axis 2 while the side view optical path A picks up or projects an image of an object point on the periphery of the central axis 2. Thus, the continuity of the image for the view angle at the central axis 2 and its vicinity is secured to make it possible to obtain a clear image and prevent the direct view optical path B from intersecting the side view optical path A so as to reduce the angle of incidence relative to the reflective surfaces. The image of the direct view optical path B and that of the side view optical path A overlap each other when the optical elements are arranged near the aperture S. The number of optical elements that can be used for forming an image is reduced to make it impossible to form a clear image when they are arranged at the side of the image plane 5 relative to the aperture S. On the other hand, the region of the image formed by the direct view optical path B and the region of the image formed by the side view optical path A can be separated from electric potential and, at the same time, the number of optical elements that can be shared by the two optical paths is increased to make it possible to obtain a clear image.

Additionally, a compact optical system can be formed and both of the images can be brought into focus by a single imaging element to make it possible to pick up a clear image when the side view optical path A and the direct view optical path B share part of the optical elements for use and a circular image of the direct view optical path B and an annular image of the side view optical path A on the outer periphery thereof are formed on the same plane.

Still additionally, the side view optical path A and the direct view optical path B can advantageously be synthetically combined by reflecting the flux of light coming in from a direction substantially orthogonal to the central axis 2 into the direction of the central axis 2 when the first reflective surface 22 or the second reflective surface 23 is arranged with its concave surface directed to the aperture S. Additionally, the strong negative power can be arranged at the object side that is a so-called telephoto type power arrangement to provide a wide view angle.

Still additionally, the power arrangement of the reflective surfaces is a negative/positive arrangement that is a telephoto type power arrangement to provide a wide view angle when both the first reflective surface 22 and the second reflective surface 23 are arranged with their concave surfaces directed to the aperture S. Such an arrangement is advantageous because the comatic aberration scarcely arises on the side view optical path A.

Still additionally, an optical system according to the present invention can advantageously be downsized when the image of the side view optical path A does not form any intermediate image on the optical path.

Preferably, an optical system according to the present invention satisfies the condition of $$D < 10 \text{ mm} \qquad (1),$$

where D is the external dimension of the optical elements.

It is highly preferable that an optical system according to the present invention satisfies the condition of the above formula from the viewpoint of alleviating the load on the subject of examination when it is employed for the image pickup system of an endoscope.

Still preferably, an optical system according to the present invention satisfies the condition of $$D/Dr < 2 \qquad (2),$$

where Dr is the external dimension of the reflection optical path.

When the above upper limit is exceeded, the imaging area of the optical system 1 becomes too small relative to the external dimension of the entire optical system 1 to make it impossible to pick up a good image due to the noise of the imaging element and the like.

Now, Examples 1 through 5 of optical system according to the present invention will be described below. The parameters of the optical systems of these examples will be described hereinafter.

Figure 1:
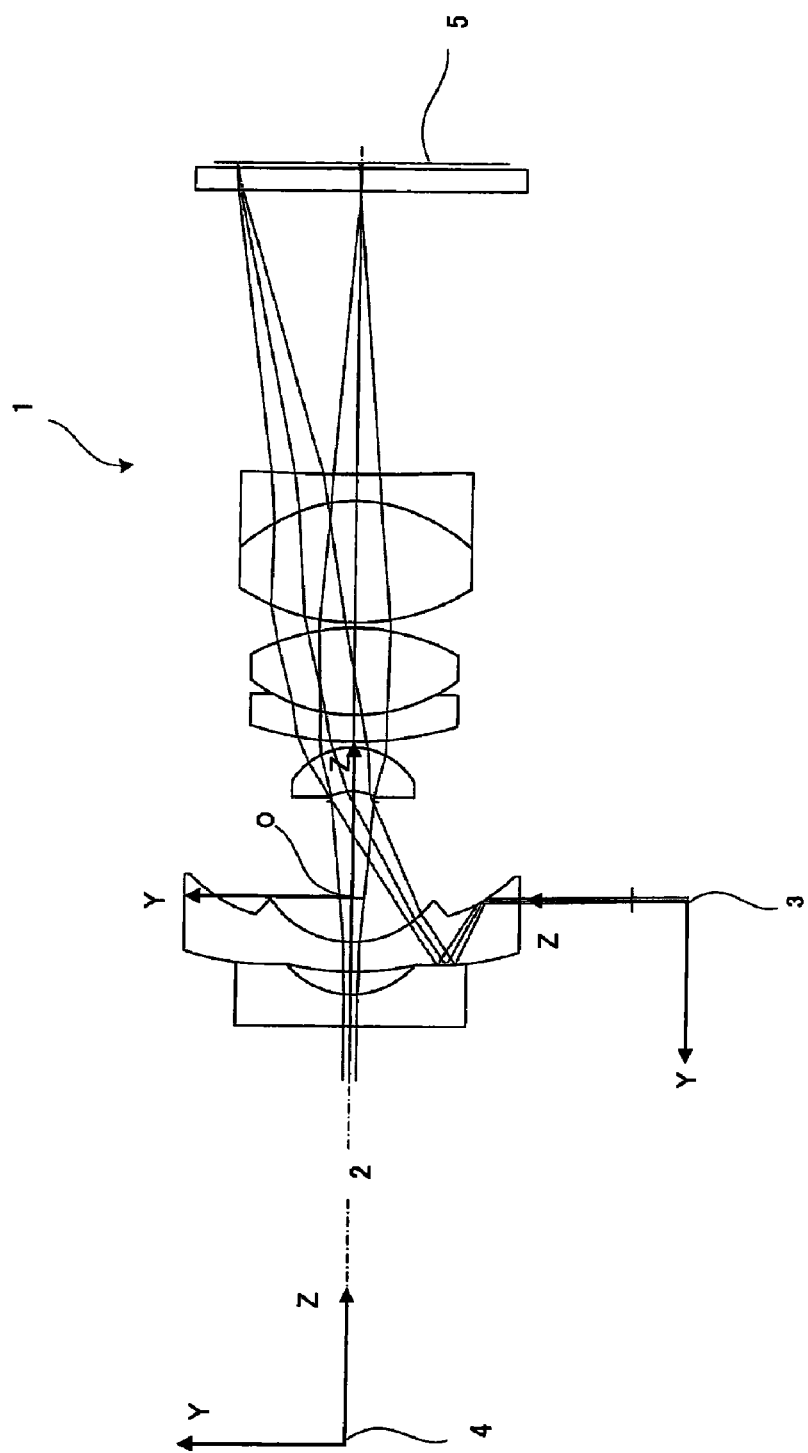
FIG. 1 is a schematic illustration of the coordinate system of an embodiment of optical system according to the present invention.

As coordinate system in forward ray tracing, for instance, the point of intersection of a prolonged line of the central principal ray of light proceeding from the side view object surface 3 toward the first surface and the central axis 2 is taken as origin O of eccentric optical surface and the direction orthogonal to the central axis 2 and of moving toward the side opposite to the side view object surface 3 as viewed from the central axis 2 is taken as a Y-axis positive direction as illustrated in FIG. 1, whereas the surface plane of the sheet of FIG. 1 is taken as a Y-Z plane. Then, the direction of moving toward the image plane 5 in FIG. 1 is taken as a Z-axis positive direction and the axis that constitutes a right hand orthogonal coordinate system with the Y-axis and the Z-axis is taken as an X-axis positive direction. Incidentally, a numerical value 4 indicates a direct view object surface.

As for the eccentric surface, the eccentricity from the origin O of the above optical system 1 that is used for defining the coordinate system that by turn defines the surface (as expressed by X, Y and Z respectively in the X-axis direction, the Y-axis direction and the Z-axis direction) and the angles of inclination of the planes extending respectively through the X-axis, the Y-axis and the Z-axis in the coordinate system that is defined by using the origin O of the optical system 1 ($\alpha$, $\beta$ and $\gamma$ (°) respectively) are given. Note that $\alpha$ and $\beta$ are taken as positive respectively in the counterclockwise directions relative to the positive direction of the X-axis and that of the Y-axis and $\gamma$ is taken as positive in the clockwise direction relative to the position direction of the Z-axis. Also note that each of the planes is rotated around the central axis thereof by $\alpha$, $\beta$ and $\gamma$ in such a way that the coordinate system that defines the planes is rotated firstly counterclockwise by a around the X-axis of the coordinate system that is defined by using the origin of the optical system and then the coordinate system obtained by rotating the initial coordinate system is rotated counterclockwise by $\beta$ around the Y-axis thereof. Then, finally, the coordinate system obtained by rotating the second coordinate system is rotated clockwise by $\gamma$ around the Z-axis thereof.

When a specific plane and the subsequent plane of the optical acting planes that the optical system of each of the examples includes form a coaxial optical system, the plane gap is given. Otherwise, the radius of curvature of each plane, the refractive index of the medium and the Abbe number are given according to the common practice.

All the terms relating to aspheric planes that are not described in the data on the constituent parameters that will be described hereinafter are equal to 0. The refractive index and the Abbe number relative to d-lines (wavelength: 587.56 nm) are given. The unit of length is mm. The eccentricity of each plane is expressed by the eccentricity from the reference plane as described above.

An aspheric plane is a rotationally symmetric defined by the formula depicted below.

$$Z = (Y^2/R)/[1+\{1-(1+k)Y^2/R^2\}^{1/2}] + aY^4 + bY^6 + cY^8 + dY^{10} + \qquad (a)$$

provided that Z is selected as an axis and Y denotes a direction perpendicular to the axis. In the above formula, R is the near-axis radius of curvature, k is the conic constant and a, b, c, d, . . . are respectively the aspheric surface coefficients of the fourth degree, the sixth degree, the eighth degree, the tenth degree and so on. The Z-axis of the above defining formula operates as the axis of a rotationally symmetric aspheric surface.

An extended rotary free curved surface is a rotationally symmetric surface given by the following definitions.

Figure 2:
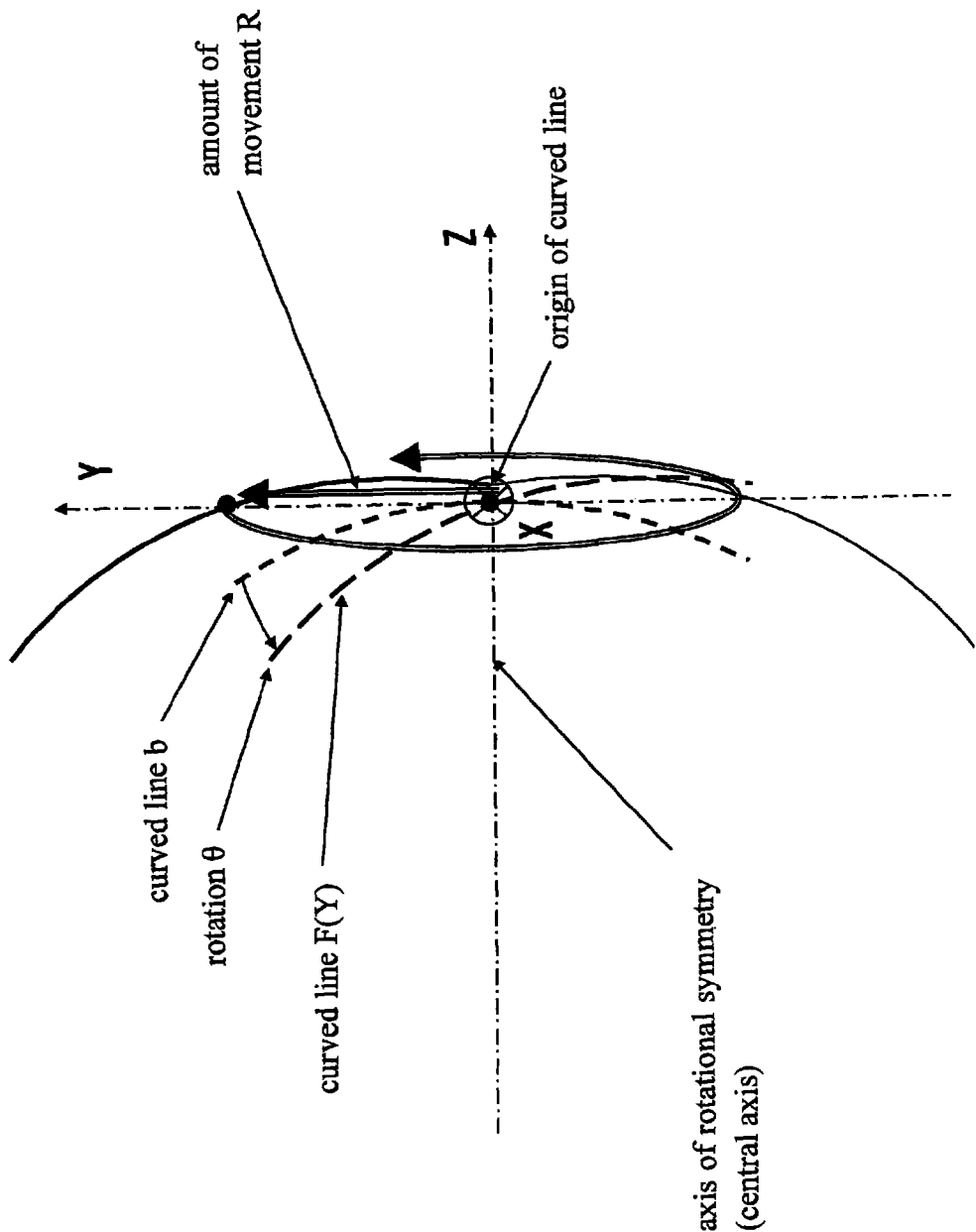
FIG. 2 is a schematic illustration of the principle of extended rotary free curved surfaces.

Firstly, a curved line (b) that passes through the origin on the Y-Z coordinate plane as illustrated in FIG. 2 is defined.

$$Z = (Y^2/RY)/\left[1+\{1-(C_1+1)Y^2/RY^2\}^{1/2}\right] + C_2Y + C_3Y^2 + C_4Y^3 + \qquad (b)$$
$$C_5Y^4 + C_6Y^5 + C_7Y^6 + \ldots + C_{21}Y^{20} + \ldots + C_{n+1}Y^n + \ldots$$

Then, curbed line F(Y) is defined by rotating the curbed line (b) by angle $\theta$(°), which is positive when it is rotated counterclockwise, facing in the positive direction of the X-axis. The curved line F(Y) also passes through the origin on the Y-Z coordinate plane.

The curved line F(Y) is translated in the direction of the positive direction of the Y-axis by distance R (in the negative direction of the Y-axis when it represents a negative value) and subsequently the translated curved line is rotated around the Z-axis to form a rotationally symmetric surface, which is an extended rotary free curved surface.

Then, as a result, the extended rotary free curved surface produces a free curved surface (free curved line) in the Y-Z plane and a circle of radius |R| in the X-Y plane.

From the above definition, the Z-axis operates as the axis of the extended rotary free curved surface (the axis of rotational symmetry).

In the above formula (b), RY is the radius of curvature of the sphere term in the Y-Z cross section, $C_1$ is the conic constant and $C_2, C_3, C_4, C_5, \ldots$ are respectively the aspheric coefficients of the first degree, the second degree, the third degree, the fourth degree and so on.

Note that a surface of circular cone whose central axis is parallel to the Y-axis is given as an extended rotary free curved surface with RY=∞, $C_1, C_2, C_3, C_4, C_5, \ldots =0$, θ=(the angle of inclination of the surface of circular cone) and R=(the radius of the bottom in the X-Z plane).

All the terms relating to aspheric planes that are not described in the data on the constituent parameters that will be described hereinafter are equal to 0. The refractive index and the Abbe number relative to d-lines (wavelength: 587.56 nm) are given. The unit of length is mm. The eccentricity of each plane is expressed by the eccentricity from the reference plane as described above.

Figure 4:
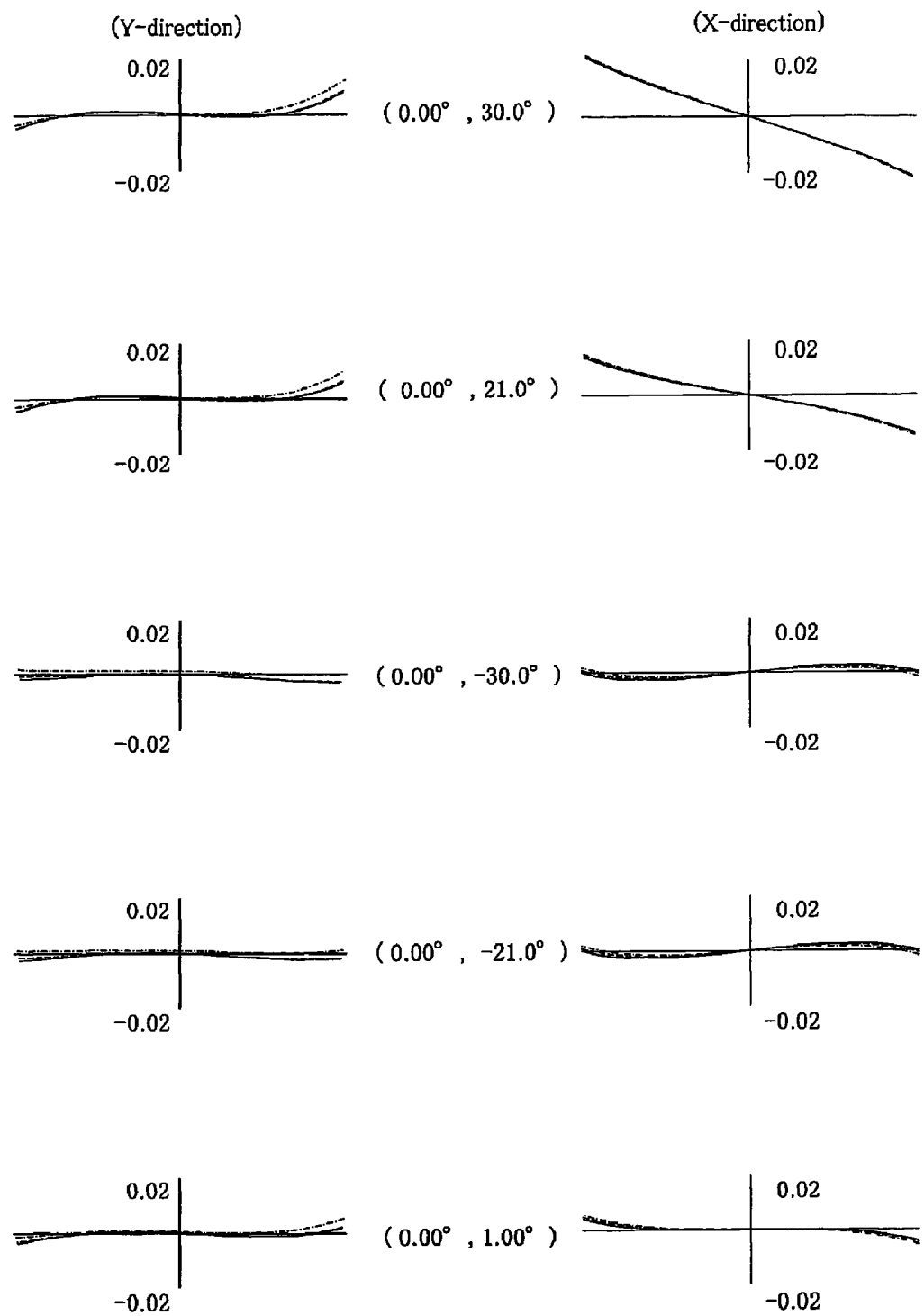
FIG. 4 is a schematic illustration of the transverse aberrations of the overall optical system of Example 1 on the side view optical path thereof.
Figure 5:
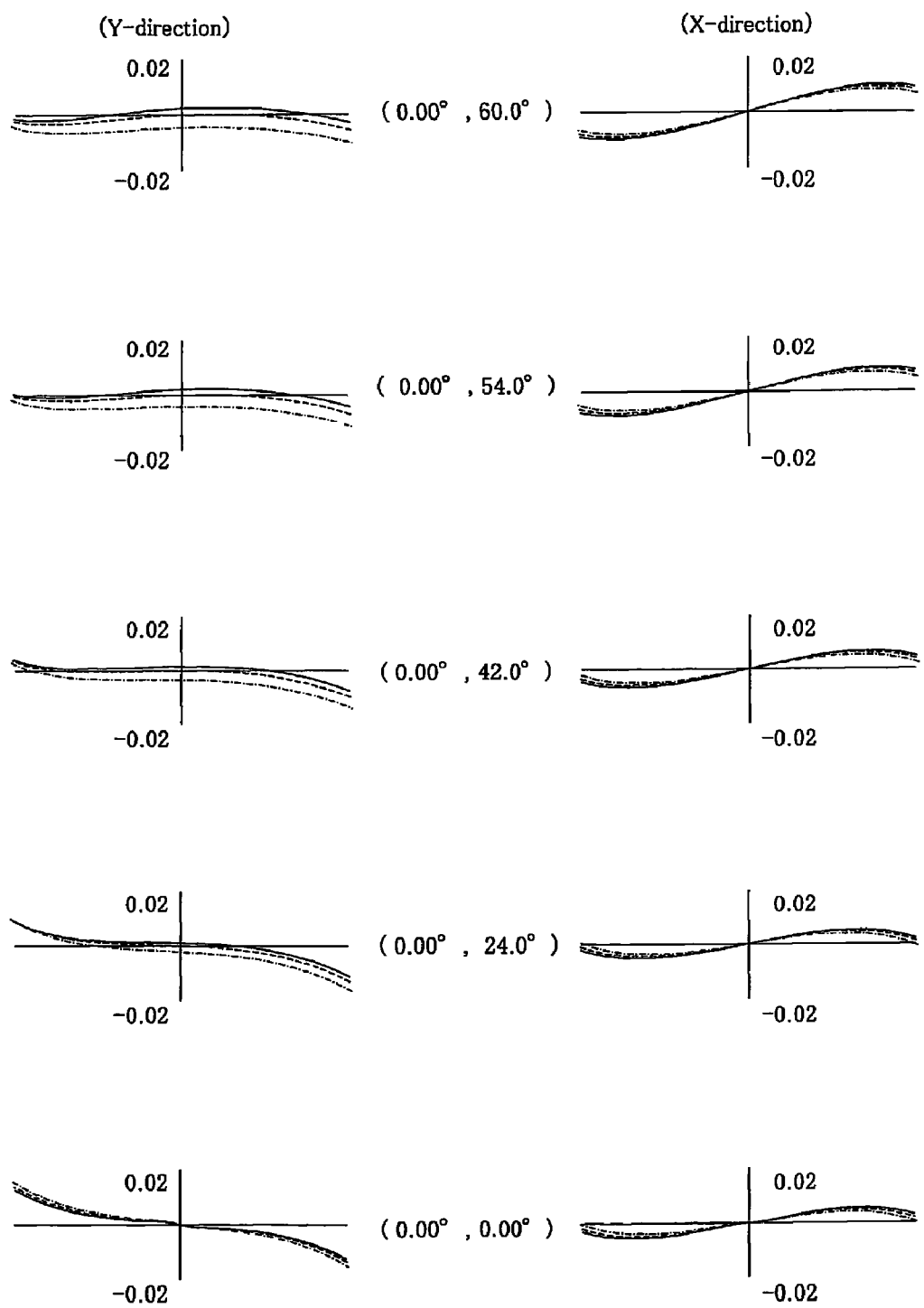
FIG. 5 is a schematic illustration of the transverse aberrations of the overall optical system of Example 1 on the direct view optical path thereof.

FIG. 3 is a schematic cross sectional view of the optical system 1 of Example 1 taken along the central axis 2 thereof. FIG. 4 is a schematic illustration of the transverse aberrations of the overall optical system of this example on the side view optical path thereof. FIG. 5 is a schematic illustration of the transverse aberrations of the overall optical system of this example on the direct view optical path thereof. In each of the views representing the transverse aberrations, each pair of angle values represented at the center indicates (the view angle in the horizontal direction, the view angle in the vertical direction). The transverse aberrations in the Y direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, none of the transmissive surfaces and the reflective surfaces that are rotationally symmetric relative to the central axis 2 of the optical system 1 and have a refractive index greater than 1 is not shared in the side view optical path. In other words, all the transmissive surfaces and all the reflective surfaces are different from each other.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group Gf includes a first group G1 and a second group G2, while the back group Gb includes a third group G3, a fourth group G4 and a fifth group G5.

The first group G1 is formed by a plano concave negative lens L1 with its concave side directed to the side of the image plane 5. The plano concave negative lens L1 has a direct view first transmissive surface 11 whose radius of curvature is infinity and a direct view second transmissive surface 12 arranged at the side of the image plane 5 relative to the direct view first transmissive surface 11.

The second group G2 is formed by a transparent medium L2 that is rotationally symmetric around the central axis 2 and has a refractive index greater than 1. It is an optical path synthesizing optical system for synthetically combining the side view optical path A and the direct view optical path B. The transparent medium L2 has a cylindrical side view first transmissive surface 21 that is arranged at the external side vis-a-vis the side view object surface so as to be parallel to the central axis 2, a side view first reflective surface 22 that is formed by a toric surface in the inside of the transparent medium L2 at the side of the central axis 2 relative to the side view first transmissive surface 21 and has negative power, a second reflective surface 23 that is formed by a toric surface in the inside of the transparent medium L2 at the side opposite to the image plane 5 as viewed from the side view first reflective surface 22 and has positive power and a side view second transmissive surface 24 that is formed by a spherical surface and arranged at the side of the image plane 5 relative to the side view second reflective surface 23 and has negative power as well as a direct view third transmissive surface 25 that is formed by a spherical surface and has positive power and a direct view fourth transmissive surface 26 that is formed by a spherical surface and arranged at the side of the image plane 5 relative to the direct view third transmissive surface 25 and has negative power. The side view second transmissive surface 24 and the direct view fourth transmissive surface 26 are the same surface.

The third group G3 is formed by a positive meniscus lens L3 with its convex surface directed to the image plane 5 and has a common first transmissive surface 31 and a common second transmissive surface 32 arranged at the side of the image plane 5 relative to the common first transmissive surface 31.

The fourth group G4 is formed by a cemented lens of a negative meniscus lens L4 with its concave surface directed to the image plane and a double convex positive lens L5 and has a common third transmissive surface 41, a cementing surface 45 arranged at the side of the image plane 5 relative to the common third transmissive surface 41 and a common fourth transmissive surface 51 arranged at the side of the image plane 5 relative to the cementing surface 45.

The fifth group G5 is formed by a cemented lens of a double convex positive lens L6 and a double concave negative lens L7 and has a common fifth transmissive surface 61, a cementing surface 67 arranged at the side of the image plane 5 relative to the common fifth transmissive surface 61 and a common sixth transmissive surface 71 arranged at the side of the image plane 5 relative to the cementing surface 67.

The optical system 1 forms a side view optical path A and a direct view optical path B. As for the side view optical path A, the flux of light entering it from the side view object surface at the side of the optical system 1 proceeds sequentially by way of the second group G2 of the front group Gf and the back group Gb and forms an annular image off the central axis 2 of the image plane 5 extending perpendicularly relative to the central axis 2. As for the direct view optical path B, the flux of light entering it from the direct view object surface near the central axis 2 of the optical system 1 proceeds sequentially by way of the front group Gf and the back group Gb and forms a circular image near the central axis 2 of the image plane 5 extending perpendicularly relative to the central axis 2.

The flux of light entering the optical system 1 from a lateral side of the optical system 1 to proceed along the side view optical path A goes into the transparent medium L2 of the second group G2 of the front group Gf by way of the side view first transmissive surface 21 and is reflected by the side view first reflective surface 22 at the side of the central axis 2 to the side opposite to the image plane 5 and then by the side view second reflective surface 23 to the side of the image plane 5 to form a substantially Z-shaped optical path before going out from the transparent medium L2 to the outside by way of the second transmissive surface 24.

Subsequently, the flux of light goes into the positive meniscus lens L3 of the third group G3 of the back group Gb at the opposite side relative to the central axis 2 by way of the aperture S arranged coaxially with the central axis 2 between the front group Gf and the back group Gb to operate as a stop and the common first transmissive surface 31 and then goes out from the common second transmissive surface 32. Thereafter, it goes into the cemented lens of the negative meniscus lens L4 and the double convex positive lens L5 of the fourth group G4 by way of the common third transmissive surface 41 and goes out from the common fourth transmissive surface 51 by way of the cementing surface 45 and then goes into the common fifth transmissive surface 61 in the cemented lens of the double convex positive lens L6 and the double concave negative lens L7 of the fifth group G5 by way of the common fifth transmissive surface 61 and goes out from the common sixth transmissive surface 71 by way of the cementing surface 67 to form an image at a predetermined radial position off the central axis 2 of the image plane 5.

The flux of light entering the optical system 1 to proceed along the direct view optical path B goes into the transparent medium L1 of the first group G1 of the front group Gf by way of the direct view first transmissive surface 11 and goes out from the transparent medium L1 by way of the direct view second transmissive surface 12 arranged at the side of the image plane 5 relative to the direct view first transmissive surface 11. Thereafter, it goes into the transparent medium L2 of the second group G2 by way of the direct view third transmissive surface 25 and goes out from the transparent medium L2 by way of the direct view fourth transmissive surface 26 arranged at the side of the image plane 5 relative to the direct view first transmissive surface 11.

Subsequently, the flux of light goes into the positive meniscus lens L3 of the third group G3 of the back group Gb by way of the aperture S arranged coaxially with the central axis 2 between the front group Gf and the back group Gb to operate as a stop and the common first transmissive surface 31 and then goes out from the common second transmissive surface 32. Thereafter, it goes into the cemented lens of the negative meniscus lens L4 and the double convex positive lens L5 of the fourth group G4 by way of the common third transmissive surface 41 and goes out from the common fourth transmissive surface 51 by way of the cementing surface 45 and then goes into the common fifth transmissive surface 61 in the cemented lens of the double convex positive lens L6 and the double concave negative lens L7 of the fifth group G5 and goes out from the common sixth transmissive surface 71 through the cementing surface 67 to form an image on the central axis 2 of the image plane 5.

The specifications of Example 1 are as follows.

| view angle (side view) | 60° to 120° |
|---|---|
| view angle (direct view) | 0° to 60° |

-continued

| incident pupil diameter | (side view) | ø0.10 mm |
|---|---|---|
| | (direct view) | ø0.42 mm |
| image size | (side view) | ø3.80 to ø4.96 |
| | (direct view) | ø2.88 |

Figure 6:
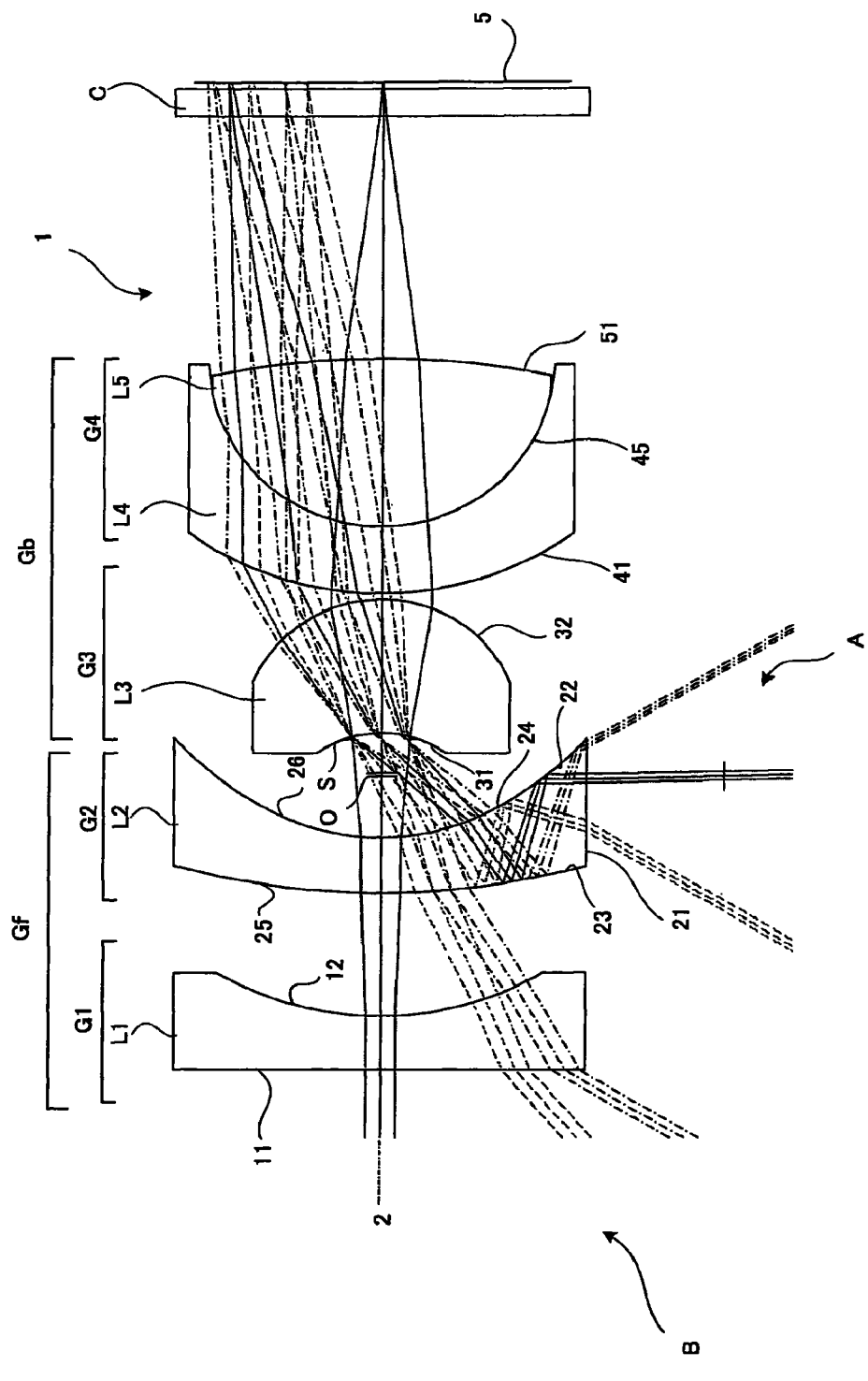
FIG. 6 is a schematic cross sectional view of the optical system of Example 2 of the present invention taken along the central axis thereof.
Figure 7:
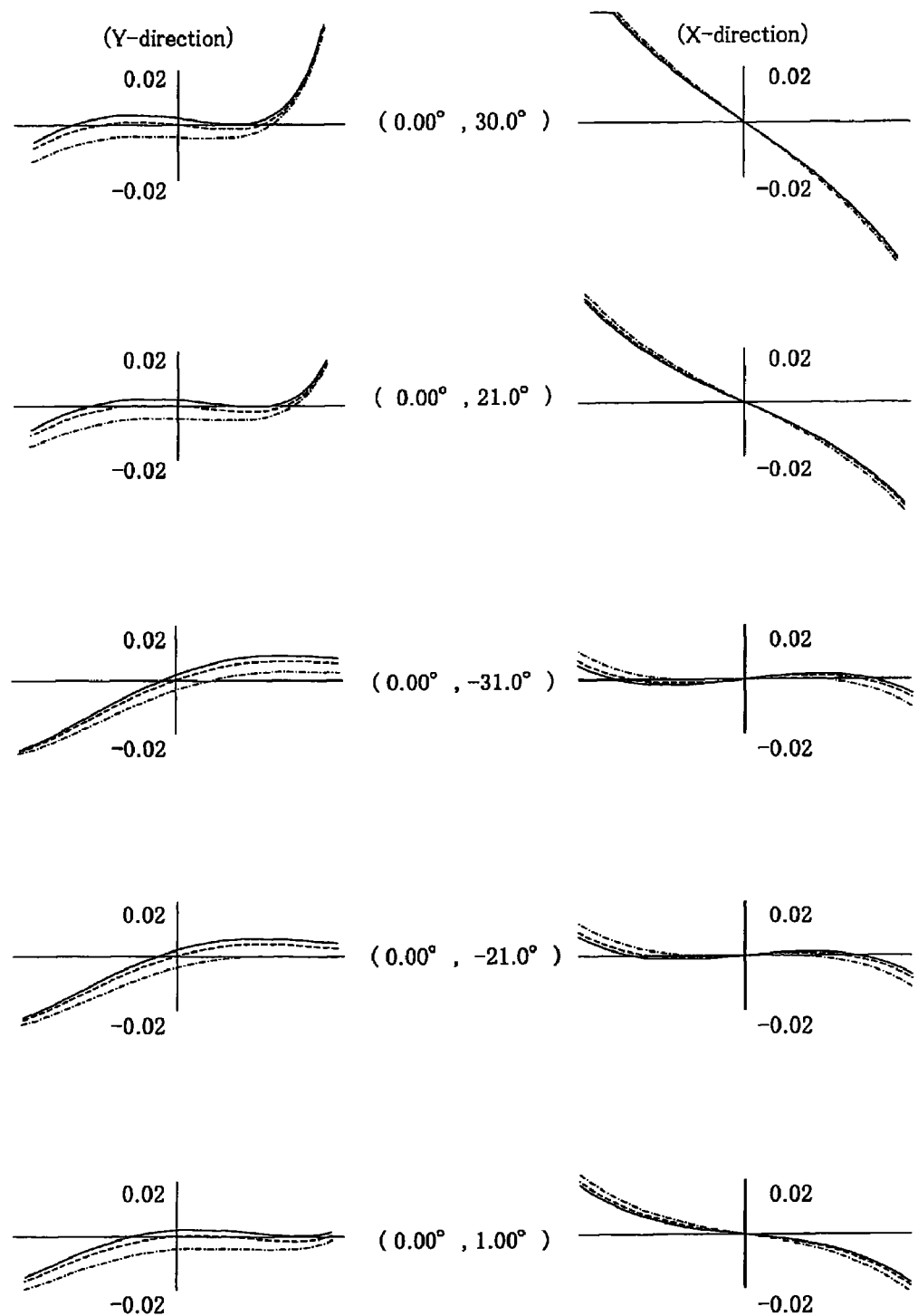
FIG. 7 is a schematic illustration of the transverse aberrations of the overall optical system of Example 2 on the side view optical path thereof.
Figure 8:
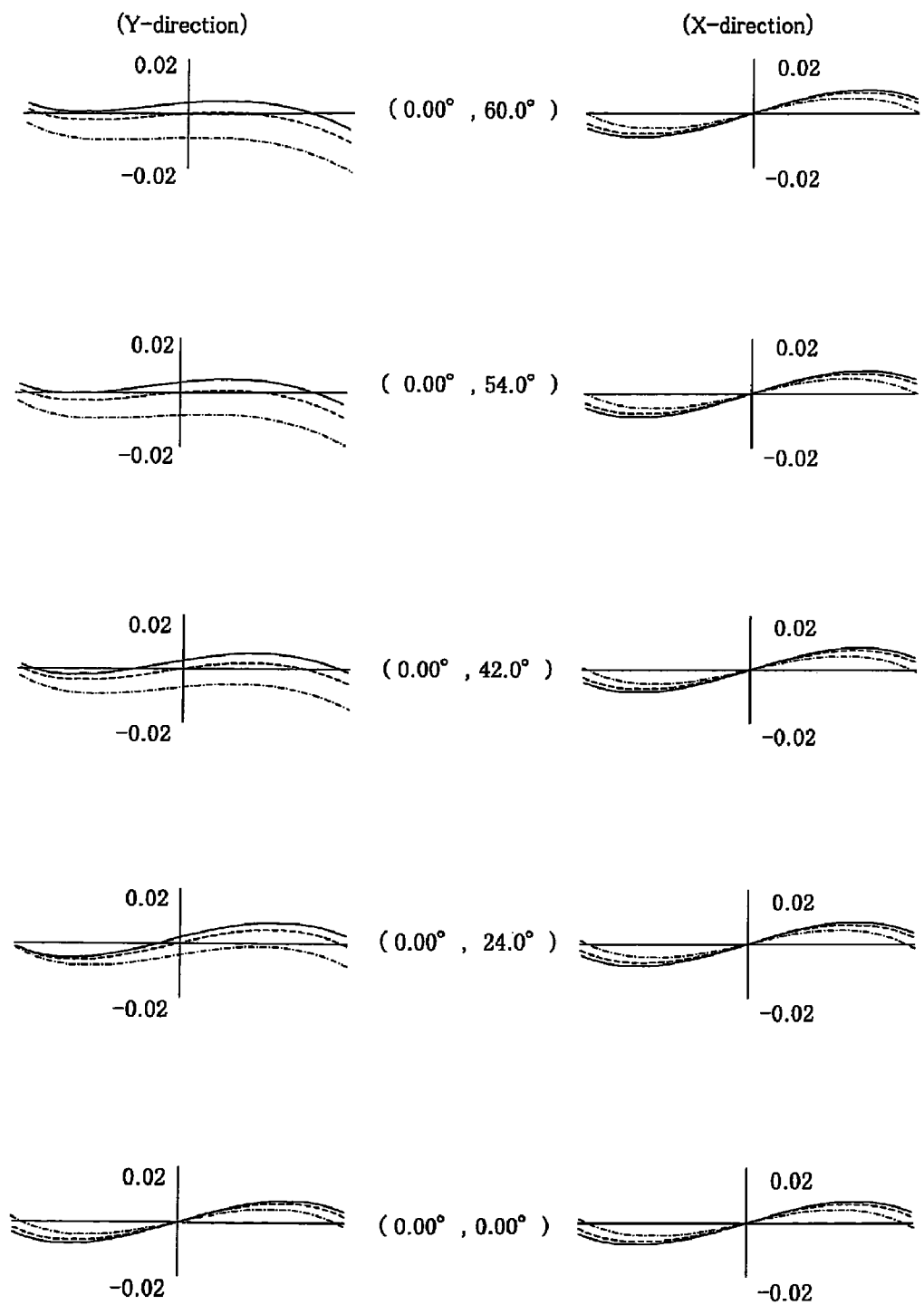
FIG. 8 is a schematic illustration of the transverse aberrations of the overall optical system of Example 2 on the direct view optical path thereof.

FIG. 6 is a schematic cross sectional view of the optical system 1 of Example 2 taken along the central axis 2 thereof. FIG. 7 is a schematic illustration of the transverse aberrations of the overall optical system of this example on the side view optical path thereof. FIG. 8 is a schematic illustration of the transverse aberrations of the overall optical system of this example on the direct view optical path thereof. In each of the views representing the transverse aberrations, each pair of angle values represented at the center indicates (the view angle in the horizontal direction, the view angle in the vertical direction). The transverse aberrations in the Y-direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, the side view first reflective surface 22 and the side view second transmissive surface 24 of the side view optical path A are formed at the same position with the same surface shape, while the side view second reflective surface 23 of the side view optical path A and the direct view third transmissive surface 25 of the direct view optical path B are formed at the same position with the same surface shape out of the transmissive surfaces and the reflective surfaces of the transparent medium that are concentric with the central axis 2 of the optical system 1 and rotationally symmetric and have a refractive index greater than 1.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group Gf includes a first group G1 and a second group G2, while the back group Gb includes a third group G3 and a fourth group G4.

The first group G1 is formed by a plano concave negative lens L1 with its concave side directed to the side of the image plane 5. The plano concave negative lens L1 has a direct view first transmissive surface 11 whose radius of curvature is infinity and a direct view second transmissive surface 12 arranged at the side of the image plane 5 relative to the direct view first transmissive surface 11.

The second group G2 is formed by a transparent medium L2 that is rotationally symmetric around the central axis 2 and has a refractive index greater than 1. It is an optical path synthesizing optical system for synthetically combining the side view optical path A and the direct view optical path B. The transparent medium L2 has a cylindrical side view first transmissive surface 21 that is arranged at the external side vis-a-vis the side view object surface so as to be parallel to the central axis 2, a side view first reflective surface 22 that is formed by an aspheric surface in the inside of the transparent medium L2 at the side of the central axis 2 relative to the side view first transmissive surface 21 and has negative power, a side view second reflective surface 23 that is formed by a spherical surface in the inside of the transparent medium L2 at the side opposite to the image plane 5 as viewed from the side view first reflective surface 22 and has positive power and a side view second transmissive surface 24 that is formed by an aspheric surface and arranged at the side of the image plane 5 relative to the side view second reflective surface 23 and has negative power as well as a direct view third transmissive surface 25 that is formed by a spherical surface and has negative power and a direct view fourth transmissive surface 26 that is formed by a spherical surface and arranged at the side of the image plane 5 relative to the direct view third transmissive surface 25 and has negative power. The side view first reflective surface 22 and the side view second transmissive surface 24 are the same surface, while the side view second reflective surface 23 and the direct view third transmissive surface 25 are the same surface.

The third group G3 is formed by a positive meniscus lens L3 with its convex surface directed to the image plane 5 and has a common first transmissive surface 31 and a common second transmissive surface 32 arranged at the side of the image plane 5 relative to the common first transmissive surface 31.

The fourth group G4 is formed by a cemented lens of a negative meniscus lens L4 with its concave surface directed to the image plane and a double convex positive lens L5 and has a common third transmissive surface 41, a cementing surface 45 arranged at the side of the image plane 5 relative to the common third transmissive surface 41 and a common fourth transmissive surface 51 arranged at the side of the image plane 5 relative to the cementing surface 45.

The optical system 1 forms a side view optical path A and a direct view optical path B. As for the side view optical path A, the flux of light entering it from the side view object surface at the side of the optical system 1 proceeds sequentially by way of the second group G2 of the front group Gf and the back group Gb and forms an annular image off the central axis 2 of the image plane 5 extending perpendicularly relative to the central axis 2. As for the direct view optical path B, the flux of light entering it from the direct view object surface near the central axis 2 of the optical system 1 proceeds sequentially by way of the front group Gf and the back group Gb and forms a circular image near the central axis 2 of the image plane 5 extending perpendicularly relative to the central axis 2.

The flux of light entering the optical system 1 from a lateral side of the optical system 1 to proceed along the side view optical path A goes into the transparent medium L2 of the second group G2 of the front group Gf by way of the side view first transmissive surface 21 and is reflected by the side view first reflective surface 22 at the side of the central axis 2 to the side opposite to the image plane 5 and then by the side view second reflective surface 23 to the side of the image plane 5 to form a substantially Z-shaped optical path before going out from the transparent medium L2 to the outside by way of the side view second transmissive surface 24.

Subsequently, the flux of light goes into the positive meniscus lens L3 of the third group G3 of the back group Gb at the opposite side relative to the central axis 2 by way of the aperture S arranged coaxially with the central axis 2 between the front group Gf and the back group Gb to operate as a stop and the common first transmissive surface 31 and then goes out from the common second transmissive surface 32. Thereafter, it goes into the negative meniscus lens L4 of the fourth group G4 by way of the common third transmissive surface 41 and goes out from the common fourth transmissive surface 51 of the double convex positive lens L5 by way of the cementing surface 45 to form an image at a predetermined radial position off the central axis 2 of the image plane 5.

The flux of light entering the optical system 1 to proceed along the direct view optical path B goes into the transparent medium L1 of the first group G1 of the front group Gf by way of the direct view first transmissive surface 11 and goes out from the transparent medium L1 by way of the direct view second transmissive surface 12 arranged at the side of the image plane 5 relative to the direct view first transmissive surface 11. Thereafter, it goes into the transparent medium L2 of the second group G2 by way of the direct view third transmissive surface 25 and goes out from the transparent medium L2 by way of the direct view fourth transmissive surface 26 arranged at the side of the image plane 5 relative to the direct view first transmissive surface 11.

Subsequently, the flux of light goes into the positive meniscus lens L3 of the third group G3 of the back group Gb by way of the aperture S arranged coaxially with the central axis 2 between the front group Gf and the back group Gb to operate as a stop and the common first transmissive surface 31 and then goes out from the common second transmissive surface 32. Thereafter, it goes into the negative meniscus lens L4 of the fourth group G4 by way of the common third transmissive surface 41 and goes out from the common fourth transmissive surface 51 of the double convex positive lens L5 by way of the cementing surface 45 to form an image on the central axis 2 of the image plane 5.

The specifications of Example 2 are as follows.

| | |
|---|---|
| view angle (side view) | 60° to 120° |
| view angle (direct view) | 0° to 60° |
| incident pupil diameter (side view) | ø0.13 mm |
| (direct view) | ø0.68 mm |
| image size (side view) | ø3.87 to ø4.90 |
| (direct view) | ø2.83 |

Figure 9:
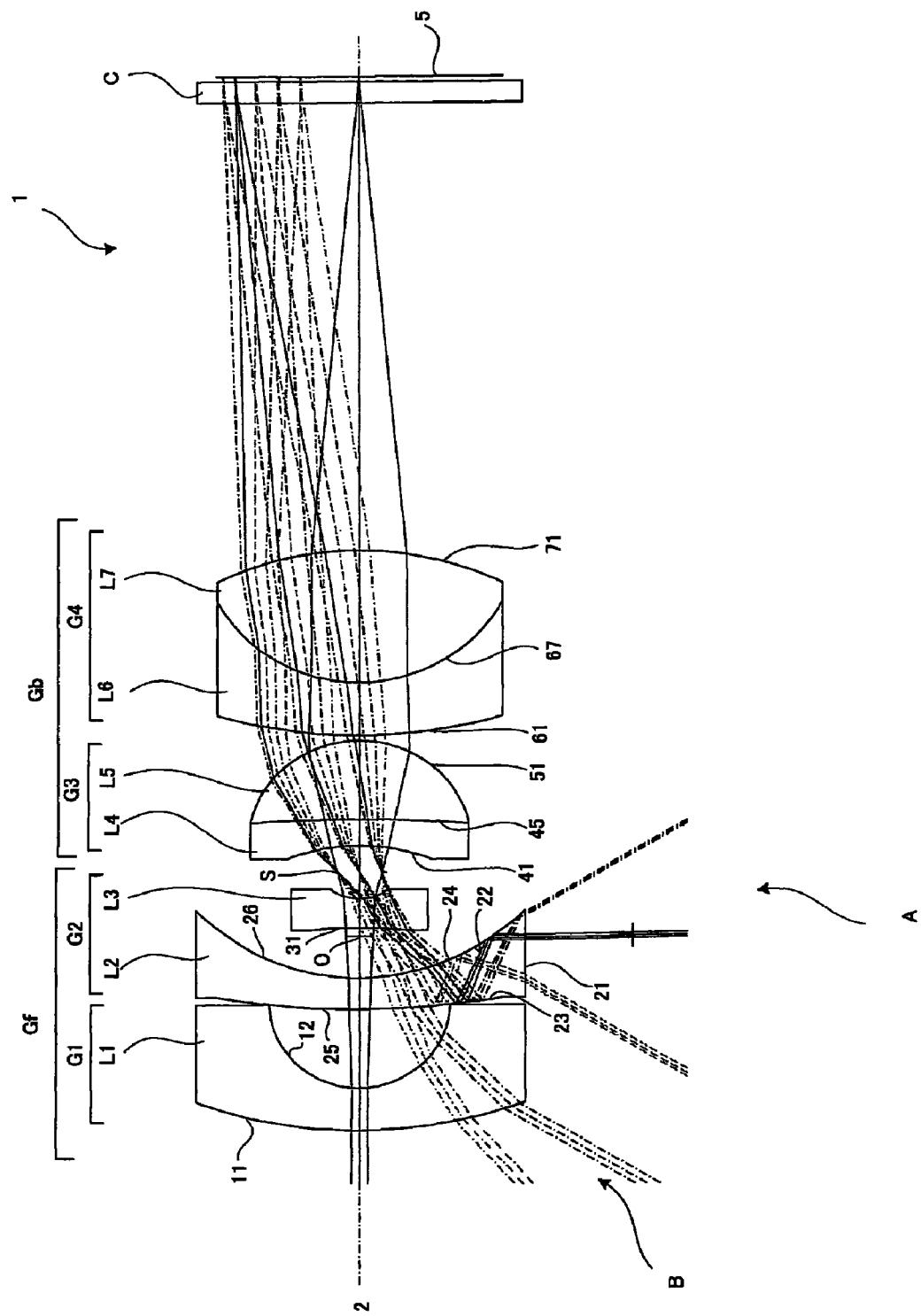
FIG. 9 is a schematic cross sectional view of the optical system of Example 3 of the present invention taken along the central axis thereof.
Figure 10:
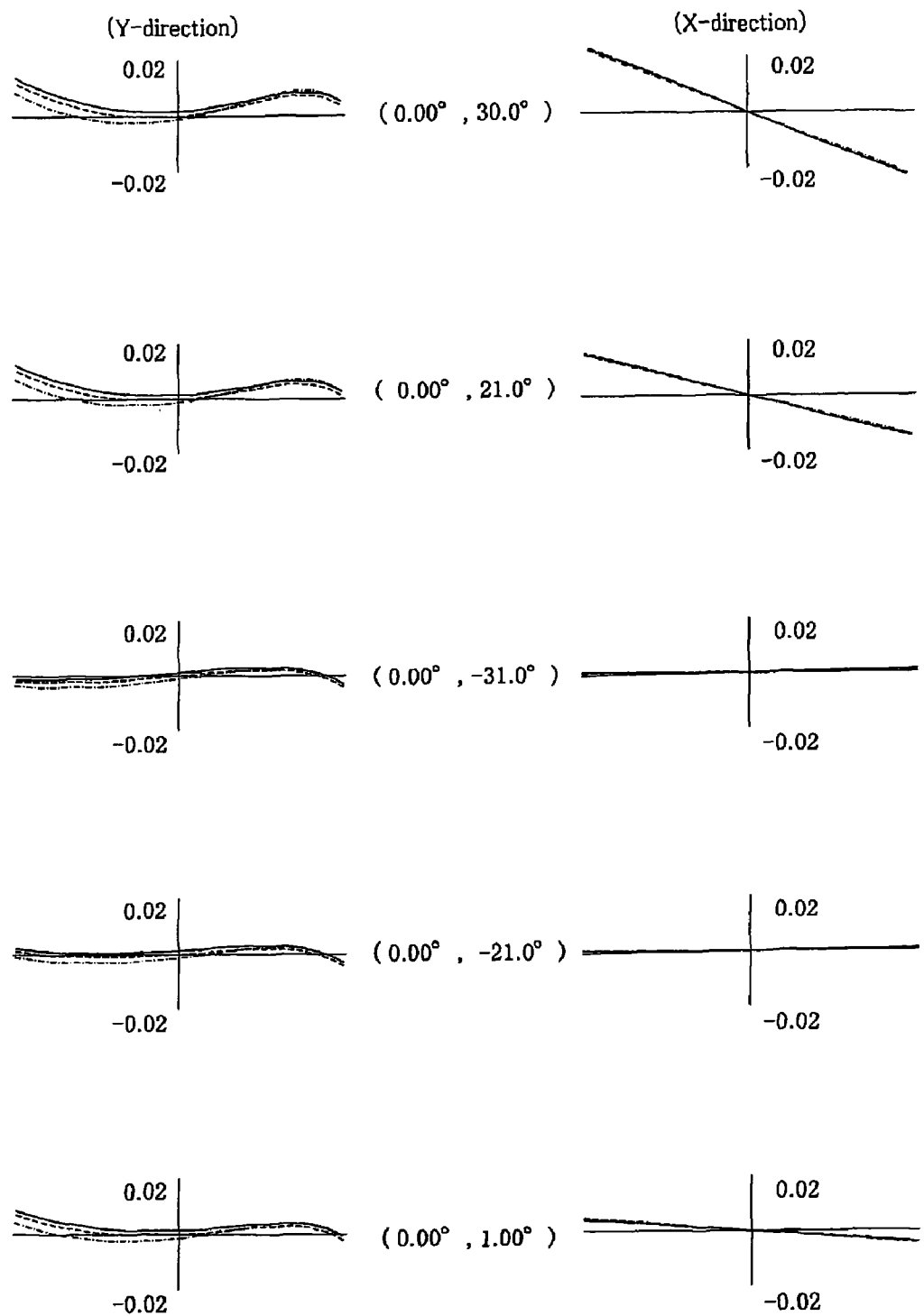
FIG. 10 is a schematic illustration of the transverse aberrations of the overall optical system of Example 3 on the side view optical path thereof.
Figure 11:
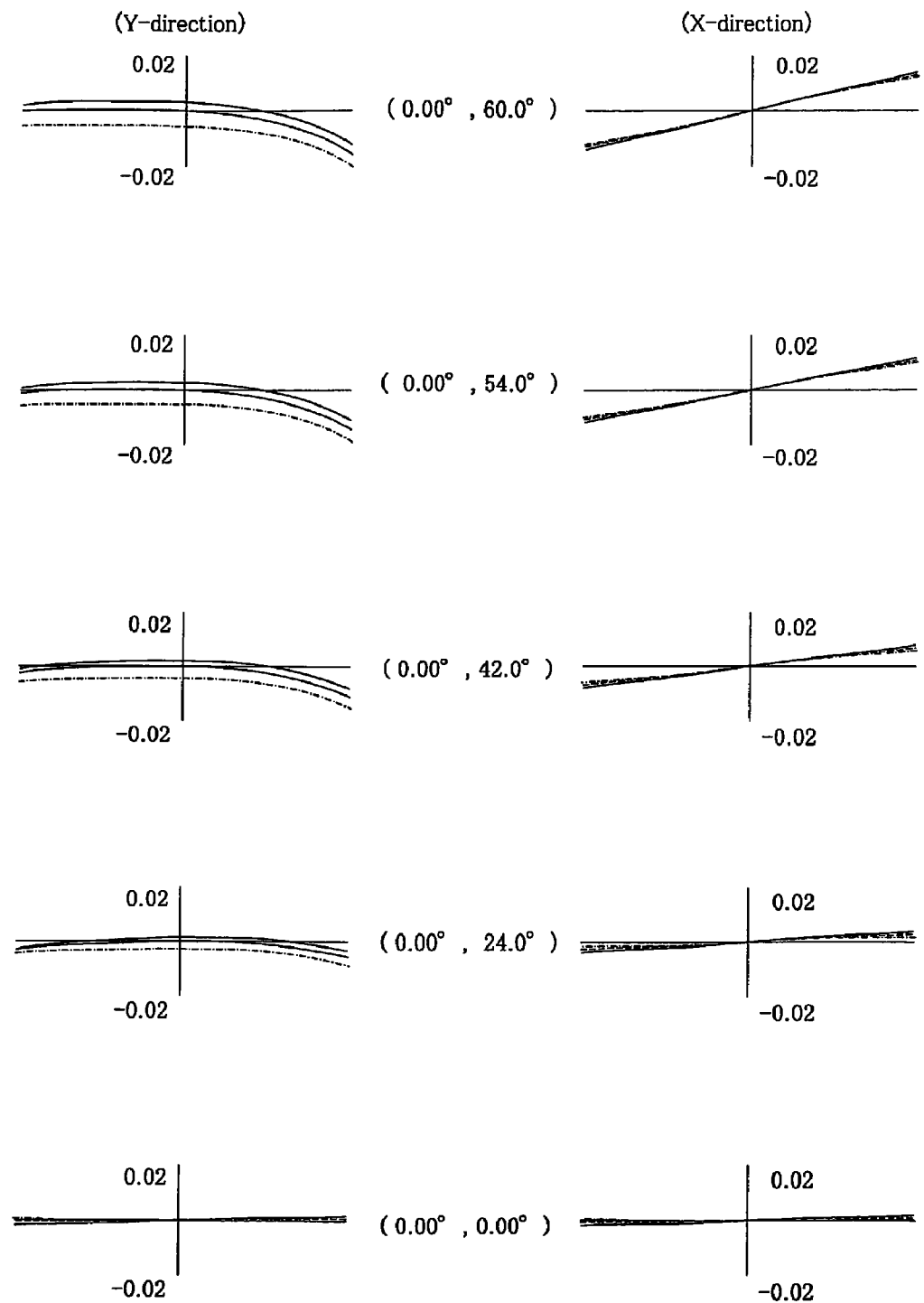
FIG. 11 is a schematic illustration of the transverse aberrations of the overall optical system of Example 3 on the direct view optical path thereof.

FIG. 9 is a schematic cross sectional view of the optical system 1 of Example 3 taken along the central axis 2 thereof. FIG. 10 is a schematic illustration of the transverse aberrations of the overall optical system of this example on the side view optical path thereof. FIG. 11 is a schematic illustration of the transverse aberrations of the overall optical system of this example on the direct view optical path thereof. In each of the views representing the transverse aberrations, each pair of angle values represented at the center indicates (the view angle in the horizontal direction, the view angle in the vertical direction). The transverse aberrations in the Y direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, the side view first reflective surface 22 and the side view second transmissive surface 24 of the side view optical path A and the direct view fourth transmissive surface 26 of the direct view optical path B are formed at the same position with the same surface shape, while the side view second reflective surface 23 of the side view optical path A and the direct view third transmissive surface 25 of the direct view optical path B are formed at the same position with the same surface shape out of the transmissive surfaces and the reflective surfaces of the transparent medium that are concentric with the central axis 2 of the optical system 1 and rotationally symmetric and show a refractive index greater than 1.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group Gf includes a first group G1 and a second group G2, while the back group Gb includes a third group G3 and a fourth group G4.

The first group G1 is formed by a negative meniscus lens L1 with its concave surface directed to the side of the image plane. The negative meniscus lens L1 has a direct view first transmissive surface 11 and a direct view second transmissive surface 12 arranged at the side of the image plane 5 relative to the direct view first transmissive surface 11.

The second group G2 is formed by a transparent medium L2 that is rotationally symmetric around the central axis 2 and has a refractive index greater than 1 and a double concave negative lens L3. It is an optical path synthesizing optical system for synthetically combining the side view optical path A and the direct view optical path B.

The transparent medium L2 has a cylindrical side view first transmissive surface 21 that is arranged at the external side vis-a-vis the side view object surface so as to be parallel to the central axis 2, a side view first reflective surface 22 that is formed by an aspheric surface in the inside of the transparent medium L2 at the side of the central axis 2 relative to the side view first transmissive surface 21 and has negative power, a side view second reflective surface 23 that is formed by a spherical surface in the inside of the transparent medium L2 at the side opposite to the image plane 5 as viewed from the side view first reflective surface 22 and has positive power and a side view second transmissive surface 24 that is formed by an aspheric surface and arranged at the side of the image plane 5 relative to the side view second reflective surface 23 and has negative power as well as a direct view third transmissive surface 25 that is formed by a spherical surface and has negative power and a direct view fourth transmissive surface 26 that is formed by a spherical surface and arranged at the side of the image plane 5 relative to the direct view third transmissive surface 25 and has negative power. The side view first reflective surface 22 and the side view second transmissive surface 24 are the same surface.

The double concave negative lens L3 is formed by spherical surfaces and has a side view third transmissive surface 31 having negative power, a side view fourth transmissive surface 32 having negative power, a direct view fifth transmissive surface 33 having negative power and a direct view sixth transmissive surface 34 having negative power. The side view third transmissive surface 31 and the direct view fifth transmissive surface 33 are the same surface, while the side view fourth transmissive surface 32 and the direct view sixth transmissive surface 34 are the same surface.

The third group G3 is formed by a cemented lens of a negative meniscus lens L4 with its convex surface directed to the image plane 5 and a positive meniscus lens L5 with its convex surface directed to the image plane 5 and has a common first transmissive surface 41, a cementing surface 45 arranged at the side of the image plane 5 relative to the common first transmissive surface 41 and a common second transmissive surface 51 arranged at the side of the image plane 5 relative to the cementing surface 45.

The fourth group G4 is formed by a cemented lens of a negative meniscus lens L6 with its concave surface directed to the image plane and a double convex positive lens L7 and has a common third transmissive surface 61, a cementing surface 67 arranged at the side of the image plane 5 relative to the common third transmissive surface 61 and a common fourth transmissive surface 71 arranged at the side of the image plane 5 relative to the cementing surface 67.

The optical system 1 forms a side view optical path A and a direct view optical path B. As for the side view optical path A, the flux of light entering it from the side view object surface at the side of the optical system 1 proceeds sequentially by way of the second group G2 of the front group Gf and the back group Gb and forms an annular image off the central axis 2 of the image plane 5 extending perpendicularly relative to the central axis 2. As for the direct view optical path B, the flux of light entering it from the direct view object surface near the central axis 2 of the optical system 1 proceeds sequentially by way of the front group Gf and the back group Gb and forms a circular image near the central axis 2 of the image plane 5 extending perpendicularly relative to the central axis 2.

The flux of light entering the optical system 1 from a lateral side of the optical system 1 to proceed along the side view optical path A goes into the transparent medium L2 of the second group G2 of the front group Gf by way of the side view first transmissive surface 21 and is reflected by the side view first reflective surface 22 at the side of the central axis 2 to the side opposite to the image plane 5 and then by the side view second reflective surface 23 to the side of the image plane 5 to form a substantially Z-shaped optical path before going out from the transparent medium L2 to the outside by way of the side view second transmissive surface 24. Then, it goes into the transparent medium L3 from the side view third transmissive surface 31 and goes out from the transparent medium L3 by way of the side view fourth transmissive surface 32.

Subsequently, the flux of light goes into the cemented lens of the negative meniscus lens L4 and the positive meniscus lens L5 of the third group G3 of the back group Gb at the opposite side relative to the central axis 2 by way of the aperture S arranged coaxially with the central axis 2 between the front group Gf and the back group Gb 2 to operate as a stop and the common first transmissive surface 41 and then goes out from the common second transmissive surface 51 by way of the cementing surface 45. Thereafter, it goes into the cemented lens of the negative meniscus lens L6 and the double convex positive lens L7 of the fourth group G4 byway of the common third transmissive surface 61 and goes out from the common fourth transmissive surface 71 by way of the cementing surface 67 to form an image at a predetermined radial position off the central axis 2 of the image plane 5.

The flux of light entering the optical system 1 to proceed along the direct view optical path B goes into the transparent medium L1 of the first group G1 of the front group Gf by way of the direct view first transmissive surface 11 and goes out from the transparent medium L1 by way of the direct view second transmissive surface 12 arranged at the side of the image plane 5 relative to the direct view first transmissive surface 11. Thereafter, it goes into the transparent medium L2 of the second group G2 by way of the direct view third transmissive surface 25 and goes out from the transparent medium L2 by way of the direct view fourth transmissive surface 26 arranged at the side of the image plane 5 relative to the direct view third transmissive surface 25. Then, it goes into the transparent medium L3 by way of the direct view fifth transmissive surface 33 and goes out from the transparent medium L3 by way of the direct view sixth transmissive surface 34 arranged at the side of the image plane 5 relative to the direct view fifth transmissive surface 33.

Subsequently, the flux of light goes into the cemented lens of the negative meniscus lens L4 and the positive meniscus lens L5 of the third group G3 of the back group Gb by way of the aperture S arranged coaxially with the central axis 2 between the front group Gf and the back group Gb to operate as a stop and the common first transmissive surface 41 and then goes out from the common second transmissive surface 51 by way of the cementing surface 45. Thereafter, it goes into the cemented lens of the negative meniscus lens L6 and the double convex positive lens L7 of the fourth group G4 by way of the common third transmissive surface 61 and goes out from the common fourth transmissive surface 71 by way of the cementing surface 67 to form an image on the central axis 2 of the image plane 5.

The specifications of Example 3 are as follows.

| | |
|---|---|
| view angle (side view) | 60° to 120° |
| view angle (direct view) | 0° to 60° |
| incident pupil diameter (side view) | ⌀0.09 mm |
| (direct view) | ⌀0.49 mm |
| image size (side view) | ⌀3.78 to ⌀4.94 |
| (direct view) | ⌀2.96 |

Figure 12:
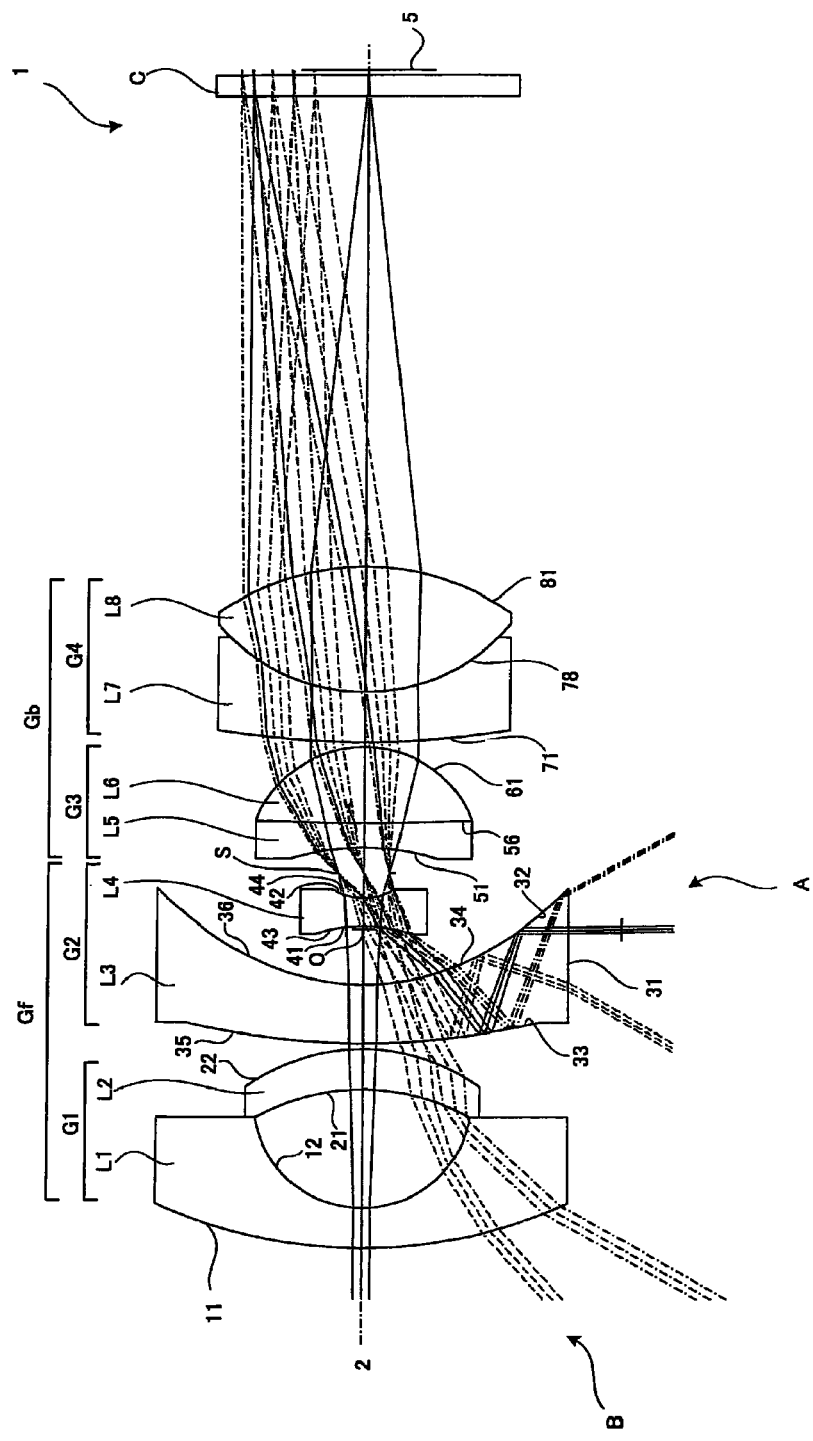
FIG. 12 is a schematic cross sectional view of the optical system of Example 4 of the present invention taken along the central axis thereof.
Figure 13:
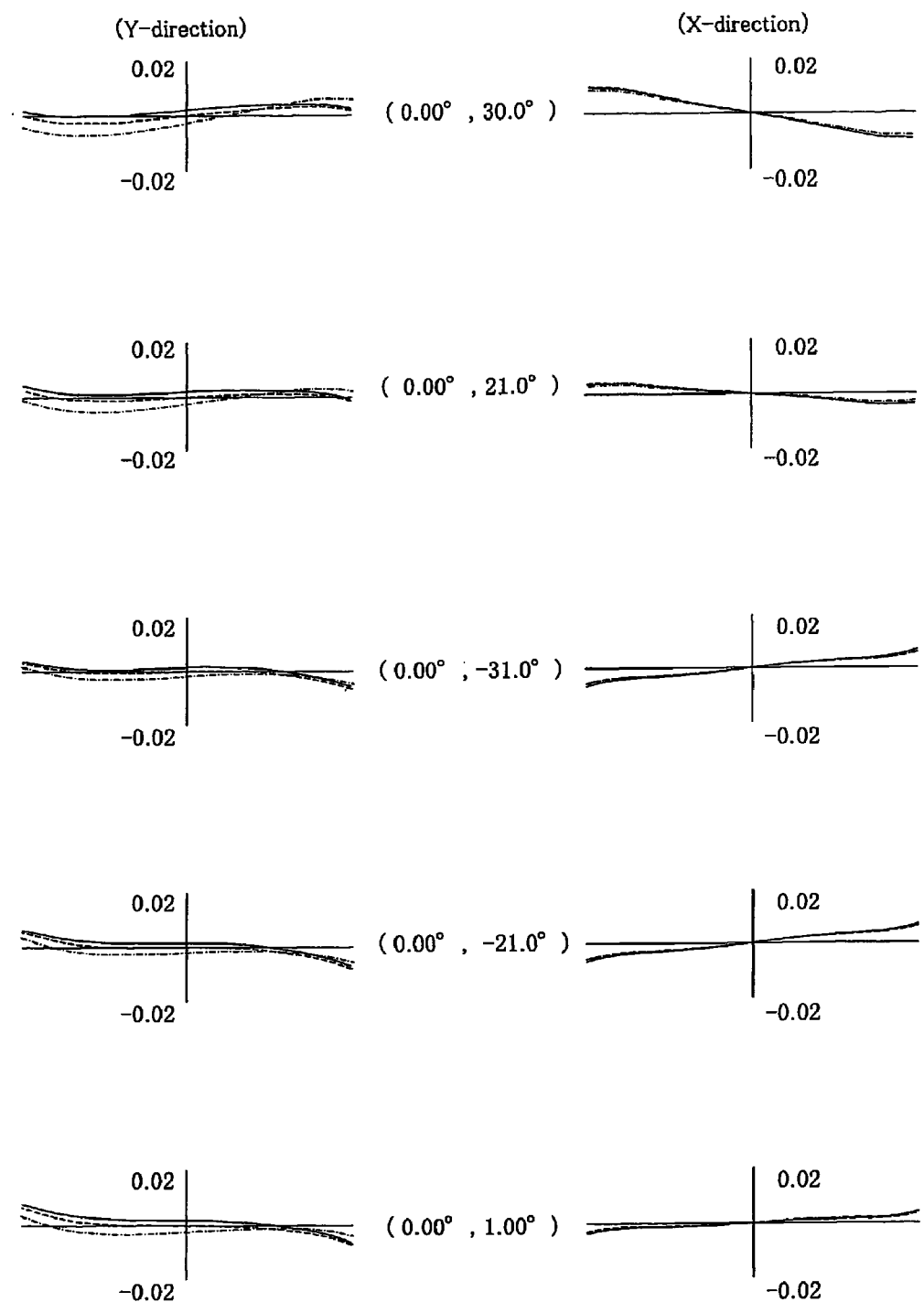
FIG. 13 is a schematic illustration of the transverse aberrations of the overall optical system of Example 4 on the side view optical path thereof.
Figure 14:
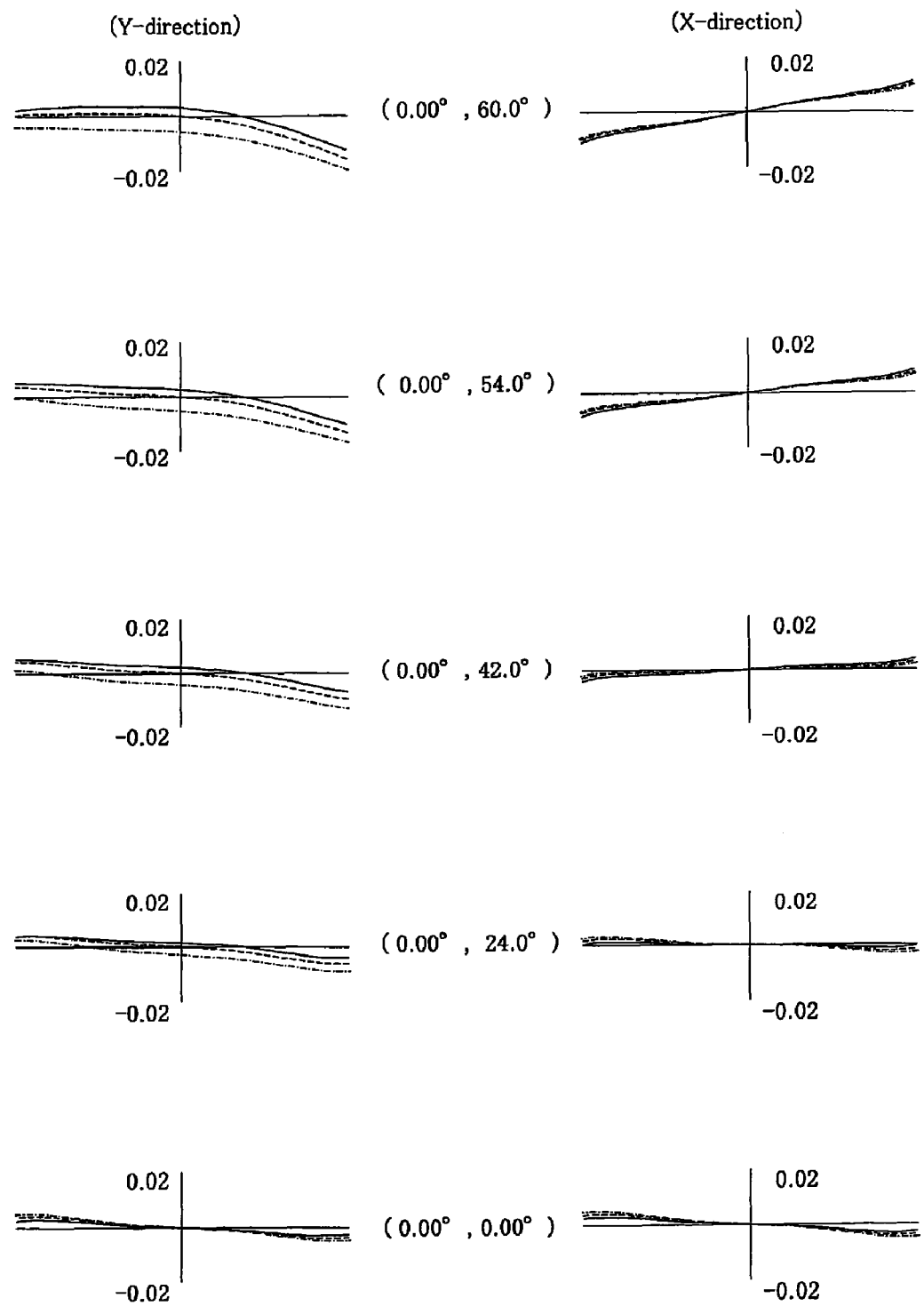
FIG. 14 is a schematic illustration of the transverse aberrations of the overall optical system of Example 4 on the direct view optical path thereof.

FIG. 12 is a schematic cross sectional view of the optical system 1 of Example 4 taken along the central axis 2 thereof. FIG. 13 is a schematic illustration of the transverse aberrations of the overall optical system of this example on the side view optical path thereof. FIG. 14 is a schematic illustration of the transverse aberrations of the overall optical system of this example on the direct view optical path thereof. In each of the views representing the transverse aberrations, each pair of angle values represented at the center indicates (the view angle in the horizontal direction, the view angle in the vertical direction). The transverse aberrations in the Y direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, the side view first reflective surface 32 and the side view second transmissive surface 34 of the side view optical path A and the direct view fourth transmissive surface 36 of the direct view optical path B are formed at the same position with the same surface shape, while the side view second reflective surface 33 of the side view optical path A and the direct view third transmissive surface 35 of the direct view optical path B are formed at the same position with the same surface shape out of the transmissive surfaces and the reflective surfaces of the transparent medium that are concentric with the central axis 2 of the optical system 1 and rotationally symmetric and have a refractive index greater than 1.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group Gf includes a first group G1 and a second group G2, while the back group Gb includes a third group G3 and a fourth group G4.

The first group G1 is formed by a negative meniscus lens L1 with its concave surface directed to the side of the image plane and a negative meniscus lens L2 with its convex surface directed to the side of the image plane 5. The negative meniscus lens L1 has a direct view first transmissive surface 11 and a direct view second transmissive surface 12 arranged at the side of the image plane 5 relative to the direct view first transmissive surface 11. The negative meniscus lens L2 has a direct view third transmissive surface 21 and a direct view fourth transmissive surface 22 arranged at the side of the image plane 5 relative to the direct view third transmissive surface 21.

The second group G2 is formed by a transparent medium L3 that is rotationally symmetric around the central axis 2 and has a refractive index greater than 1 and a double concave lens L4. It is an optical path synthesizing optical system for synthetically combining the side view optical path A and the direct view optical path B.

The transparent medium L3 has a cylindrical side view first transmissive surface 31 that is arranged at the external side vis-a-vis the side view object surface so as to be parallel to the central axis 2, a side view first reflective surface 32 that is formed by an aspheric surface in the inside of the transparent medium L3 at the side of the central axis 2 relative to the side view first transmissive surface 31 and has negative power, a side view second reflective surface 33 that is formed by a spherical surface in the inside of the transparent medium L3 at the side opposite to the image plane 5 as viewed from the side view first reflective surface 32 and has positive power and a side view second transmissive surface 34 that is formed by an aspheric surface and arranged at the side of the image plane 5 relative to the side view second reflective surface 33 and has negative power as well as a direct view fifth transmissive surface 35 that is formed by a spherical surface and has positive power and a direct view sixth transmissive surface 36 that is formed by a spherical surface, in the side view optical path A, and has negative power. The side view first reflective surface 32, the side view second transmissive surface 34 and the direct view sixth transmissive surface 36 are the same surface, while the side view second reflective surface 33 and the direct view fifth transmissive surface are the same surface.

The double concave negative lens IA is formed by spherical surfaces and has a side view third transmissive surface 41 having negative power, a side view fourth transmissive surface 42 having negative power, a direct view fifth transmissive surface 43 having negative power and a direct view sixth transmissive surface 44 having negative power. The side view third transmissive surface 41 and the direct view fifth transmissive surface 43 are the same surface, while the side view fourth transmissive surface 42 and the direct view sixth transmissive surface 44 are the same surface.

The third group G3 is formed by a cemented lens of a double concave negative lens L5 and a double convex positive lens L6 and has a common first transmissive surface 51, a cementing surface 56 arranged at the side of the image plane 5 relative to the common first transmissive surface 51 and a common second transmissive surface 61 arranged at the side of the image plane 5 relative to the cementing surface 56.

The fourth group G4 is formed by a cemented lens of a negative meniscus lens L7 with its concave surface directed to the image plane and a double convex positive lens L8 and has a common third transmissive surface 71, a cementing surface 78 arranged at the side of the image plane 5 relative to the common third transmissive surface 71 and a common fourth transmissive surface 81 arranged at the side of the image plane 5 relative to the cementing surface 78.

The optical system 1 forms a side view optical path A and a direct view optical path B. As for the side view optical path A, the flux of light entering it from the side view object surface at the side of the optical system 1 proceeds sequentially by way of the second group G2 of the front group Gf and the back group Gb and forms an annular image off the central axis 2 of the image plane 5 extending perpendicularly relative to the central axis 2. As for the direct view optical path B, the flux of light entering it from the direct view object surface near the central axis 2 of the optical system 1 proceeds sequentially by way of the front group Gf and the back group Gb and forms a circular image near the central axis 2 of the image plane 5 extending perpendicularly relative to the central axis 2.

The flux of light entering the optical system 1 from a lateral side of the optical system 1 to proceed along the side view optical path A goes into the transparent medium L3 of the second group G2 of the front group Gf by way of the side view first transmissive surface 31 and is reflected by the side view first reflective surface 32 at the side of the central axis 2 to the side opposite to the image plane 5 and then by the side view second reflective surface 33 to the side of the image plane 5 to form a substantially Z-shaped optical path before going out from the transparent medium L3 to the outside by way of the side view second transmissive surface 34. Then, it goes into the transparent medium L4 from the side view third transmissive surface 41 and goes out from the transparent medium L4 by way of the side view fourth transmissive surface 42.

Subsequently, the flux of light goes into the cemented lens of the double concave negative lens L5 and the double convex positive lens L6 of the third group G3 of the back group Gb at the opposite side relative to the central axis 2 by way of the aperture S arranged coaxially with the central axis 2 between the front group Gf and the back group Gb to operate as a stop and the common first transmissive surface 51 and then goes out from the common second transmissive surface 61 by way of the cementing surface 56. Thereafter, it goes into the cemented lens of the negative meniscus lens L7 and the double convex positive lens L8 of the fourth group G4 by way of the common third transmissive surface 71 and goes out from the common fourth transmissive surface 81 by way of the cementing surface 78 to form an image at a predetermined radial position off the central axis 2 of the image plane 5.

The flux of light entering the optical system 1 to proceed along the direct view optical path B goes into the transparent medium L1 of the first group G1 of the front group Gf by way of the direct view first transmissive surface 11 and goes out from the transparent medium L1 by way of the direct view second transmissive surface 12 arranged at the side of the image plane 5 relative to the direct view first transmissive surface 11. Thereafter, it goes into the transparent medium L2 of the second group G2 by way of the direct view third transmissive surface 21 and goes out from the transparent medium L2 by way of the direct view fourth transmissive surface 22 arranged at the side of the image plane 5 relative to the direct view first transmissive surface 11. Then, it goes into the transparent medium L3 by way of the direct view fifth transmissive surface 35 and goes out from the transparent medium L3 by way of the direct view sixth transmissive surface 36 arranged at the side of the image plane 5 relative to the direct view fifth transmissive surface 35. Thereafter, it goes into the transparent medium L4 by way of the direct view seventh transmissive surface 43 and goes out from the transparent medium L4 by way of the direct view eighth transmissive surface 44 arranged at the side of the image plane 5 relative to the direct view seventh transmissive surface 43.

Subsequently, the flux of light goes into the cemented lens of the double concave negative lens L5 and the double convex positive lens L6 of the third group G3 of the back group Gb by way of the aperture S arranged coaxially with the central axis 2 between the front group Gf and the back group Gb 2 to operate as a stop and the common first transmissive surface 51 and then goes out from the common second transmissive surface 61 by way of the cementing surface 56. Thereafter, it goes into the cemented lens of the negative meniscus lens L7 and the double convex positive lens L8 of the fourth group G4 by way of the common third transmissive surface 71 and goes out from the common fourth transmissive surface 81 by way of the cementing surface 78 to form an image on the central axis 2 of the image plane 5.

The specifications of Example 4 are as follows.

| | | |
|---|---|---|
| view angle (side view) | | 60° to 120° |
| view angle (direct view) | | 0° to 60° |
| incident pupil diameter | (side view) | ⌀0.11 mm |
| | (direct view) | ⌀0.46 mm |
| image size | (side view) | ⌀3.77 to ⌀4.94 |
| | (direct view) | ⌀2.97 |

Figure 15:
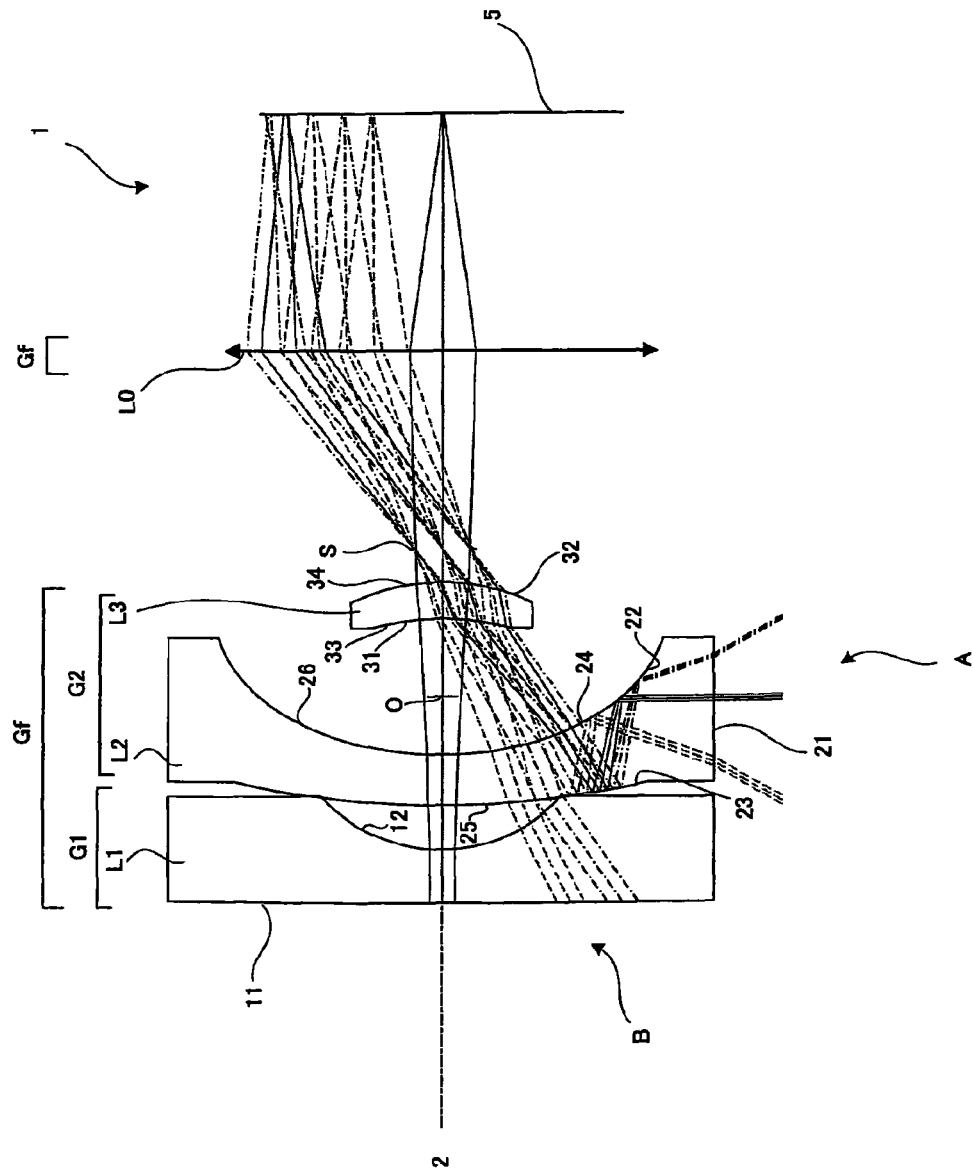
FIG. 15 is a schematic cross sectional view of the optical system of Example 5 of the present invention taken along the central axis thereof.
Figure 16:
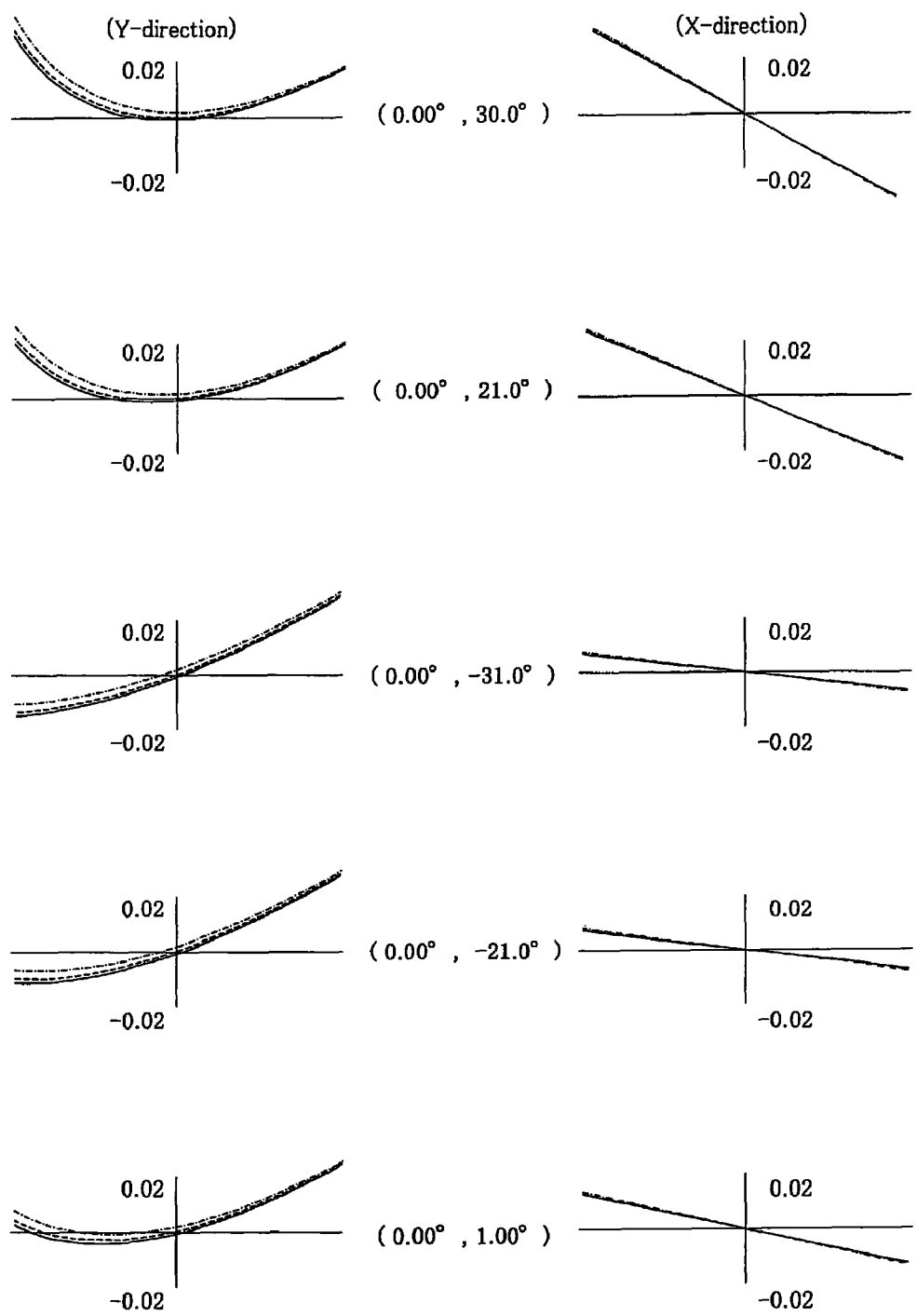
FIG. 16 is a schematic illustration of the transverse aberrations of the overall optical system of Example 5 on the side view optical path thereof.
Figure 17:
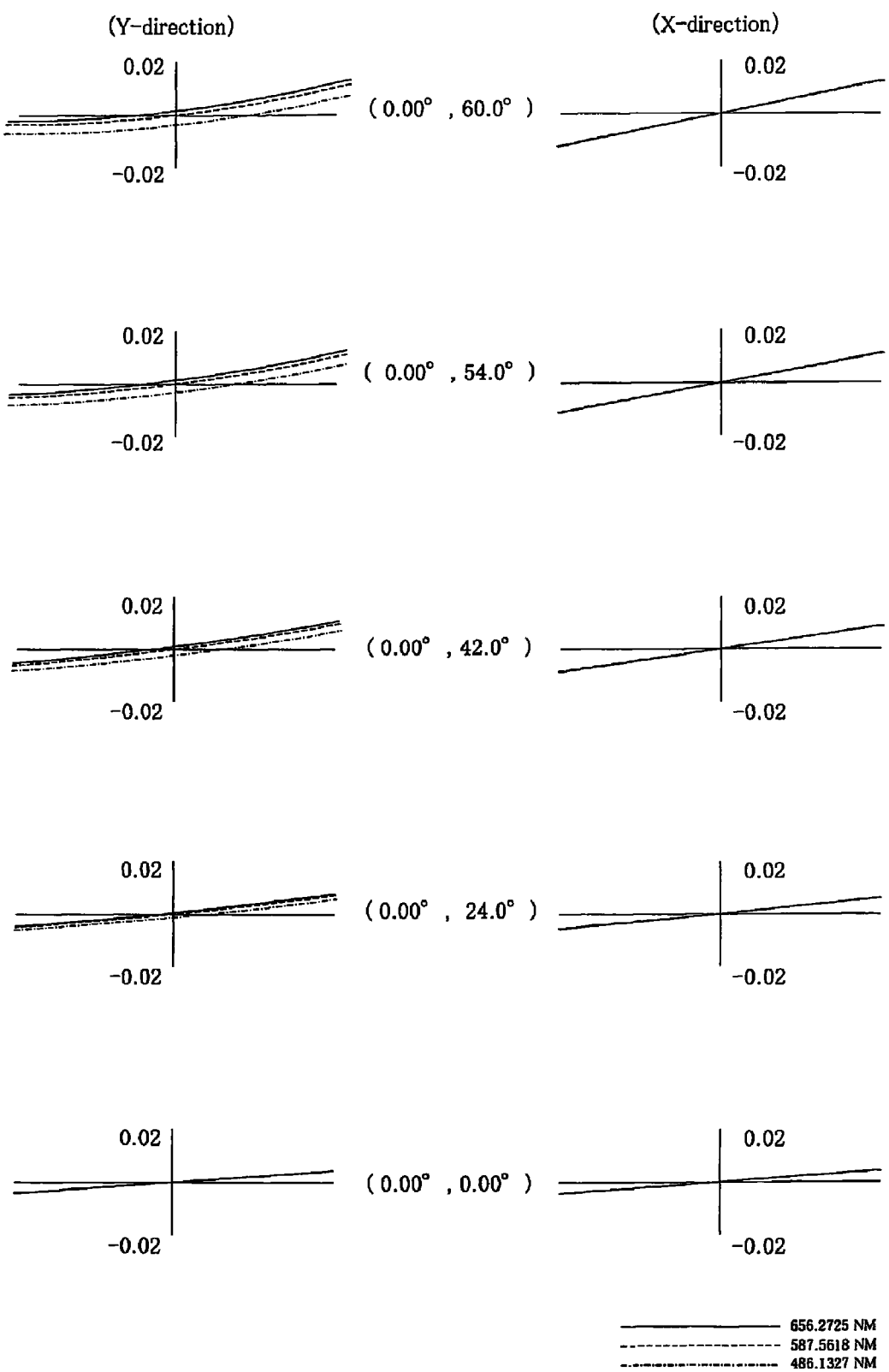
FIG. 17 is a schematic illustration of the transverse aberrations of the overall optical system of Example 5 on the direct view optical path thereof.

FIG. 15 is a schematic cross sectional view of the optical system 1 of Example 5 taken along the central axis 2 thereof. FIG. 16 is a schematic illustration of the transverse aberrations of the overall optical system of this example on the side view optical path thereof. FIG. 17 is a schematic illustration of the transverse aberrations of the overall optical system of this example on the direct view optical path thereof. In each of the views representing the transverse aberrations, each pair of angle values represented at the center indicates (the view angle in the horizontal direction, the view angle in the vertical direction). The transverse aberrations in the Y direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, the side view first reflective surface 22 and the side view second transmissive surface 24 of the side view optical path A and the direct view fourth transmissive surface 26 of the direct view optical path B are formed at the same position with the same surface shape, while the side view second reflective surface 23 of the side view optical path A and the direct view third transmissive surface 25 of the direct view optical path B are formed at the same position with the same surface shape out of the transmissive surfaces and the reflective surfaces of the transparent medium that are concentric with the central axis 2 of the optical system 1 and rotationally symmetric and have a refractive index greater than 1 to form an attachment optical system to be fitted to the front end of an existing optical system. In the drawings, the arrows indicate an ideal lens.

The optical system 1 includes a front group Gf that is rotationally symmetric relative to the central axis 2, a back group Gb that is formed by the ideal lens and an aperture S arranged between the front group Gf and the back group Gb so as to be coaxial with the central axis 2. The front group Gf includes a first group G1 and a second group G2, while the back group Gb includes the ideal lens L0.

The first group G1 is formed by a negative meniscus lens L1 with its convex surface directed to the side of the object plane and has a direct view first transmissive surface 11 and a direct view second transmissive surface 12 having negative power and arranged at the side of the image plane 5 relative to the direct view first transmissive surface 11.

The second group G2 is formed by a transparent medium L2 that is rotationally symmetric around the central axis 2 and has a refractive index greater than 1 and a negative meniscus lens L3 with its convex surface directed to the image plane 5.

It is an optical path synthesizing optical system for synthetically combining the side view optical path A and the direct view optical path B.

The transparent medium L2 has a cylindrical side view first transmissive surface 21 that is arranged at the external side vis-a-vis the side view object surface so as to be parallel to the central axis 2, a side view first reflective surface 22 that is formed by an aspheric surface in the inside of the transparent medium L2 at the side of the central axis 2 relative to the side view first transmissive surface 21 and has negative power, a second reflective surface 23 that is formed by an aspheric surface in the inside of the transparent medium L2 at the side opposite to the image plane 5 as viewed from the side view first reflective surface 22 and has positive power and a side view second transmissive surface 24 that is formed by an aspheric surface and arranged at the side of the image plane 5 relative to the side view second reflective surface 23 and has negative power as well as a direct view third transmissive surface 25 that is formed by an aspheric surface and has negative power and a direct view fourth transmissive surface 26 that is formed by an aspheric surface and arranged at the side of the image plane 5 relative to the direct view third transmissive surface 25 and has negative power. The side view first reflective surface 22, the side view second transmissive surface 24 and the direct view fourth transmissive surface 26 are the same surface, while the side view second reflective surface 23 and the direct view third transmissive surface 25 are the same surface.

The negative meniscus lens L3 has a side view third transmissive surface 31, a side view fourth transmissive surface 32, a direct view fifth transmissive surface 33 and a direct view sixth transmissive surface 34. The side view third transmissive surface 31 and the direct view fifth transmissive surface 33 are the same surface, while the side view fourth transmissive surface 32 and the direct view sixth transmissive surface 34 are the same surface.

The back group Gb is formed by the ideal lens L0.

The optical system 1 forms a side view optical path A and a direct view optical path B. As for the side view optical path A, the flux of light entering it from the side view object surface at the side of the optical system 1 proceeds sequentially by way of the second group G2 of the front group Gf and the back group Gb and forms an annular image off the central axis 2 of the image plane 5 extending perpendicularly relative to the central axis 2. As for the direct view optical path B, the flux of light entering it from the direct view object surface near the central axis 2 of the optical system 1 proceeds sequentially by way of the front group Gf and the back group Gb and forms a circular image near the central axis 2 of the image plane 5 extending perpendicularly relative to the central axis 2.

The flux of light entering the optical system 1 from a lateral side of the optical system 1 to proceed along the side view optical path A goes into the transparent medium L2 of the second group G2 of the front group Gf by way of the side view first transmissive surface 21 and is reflected by the side view first reflective surface 22 at the side of the central axis 2 to the side opposite to the image plane 5 and then by the side view second reflective surface 23 to the side of the image plane 5 to form a substantially Z-shaped optical path before going out from the transparent medium L2 to the outside by way of the side view second transmissive surface 24. Then, it goes into the transparent medium L3 by way of the side view third transmissive surface 31 and goes out from the transparent medium L3 by way of the side view fourth transmissive surface 32.

Subsequently, the flux of light proceeds by way of the aperture S arranged coaxially with the central axis 2 between the front group Gf and the back group Gb to operate as a stop and the ideal lens L0 of the back group Gb to form an image at a predetermined radial position off the central axis 2 of the image plane 5.

The flux of light entering the optical system 1 to proceed along the direct view optical path B goes into the transparent medium L1 of the first group G1 of the front group Gf by way of the direct view first transmissive surface 11 and goes out from the transparent medium L1 by way of the direct view second transmissive surface 12 arranged at the side of the image plane 5 relative to the direct view first transmissive surface 11. Thereafter, it goes into the transparent medium L2 of the second group G2 by way of the direct view third transmissive surface 25 and goes out from the transparent medium L2 by way of the direct view fourth transmissive surface 26 arranged at the side of the image plane 5 relative to the direct view first transmissive surface 11. Then, it goes into the transparent medium L3 by way of the direct view fifth transmissive surface 33 and goes out from the transparent medium L3 by way of the direct view sixth transmissive surface 34 arranged at the side of the image plane 5 relative to the direct view fifth transmissive surface 33.

Subsequently, the flux of light proceeds by way of the aperture S arranged coaxially with the central axis 2 between the front group Gf and the back group Gb 2 to operate as a stop and the ideal lens L0 of the back group Gb to form an image on the central axis 2 of the image plane 5.

The specifications of Example 5 are as follows.

| | |
|---|---|
| view angle (side view) | 60° to 120° |
| view angle (direct view) | 0° to 60° |
| incident pupil diameter (side view) | ø0.08 mm |
| (direct view) | ø0.37 mm |
| image size (side view) | ø3.74 to ø4.99 |
| (direct view) | ø2.86 |

Some of the parameters of the above-described Examples 1 through 5 are listed below. In the table represented below, "ASS" denotes an aspheric surface and "ERFS" denotes an extended rotary free curved surface, while "Re" denotes a reflective surface.

Example 1

| Side view optical path | | | | | |
|---|---|---|---|---|---|
| Surface number | Radius of curvature | Plane gap | Eccentricity | Refractive index | Abbe number |
| Object surface | ∞ | ∞ | eccentricity (1) | | |
| 1 | ERFS [1] | | eccentricity (2) | 1.8348 | 42.7 |
| 2 | ERFS [2] (RE) | | eccentricity (3) | 1.8348 | 42.7 |
| 3 | ERFS [3] (RE) | | eccentricity (4) | 1.8348 | 42.7 |
| 4 | ERFS [4] | | eccentricity (5) | | |
| 5 | ∞ (Stop) | 0.20 | eccentricity (6) | | |
| 6 | −0.89 | 0.80 | | 1.7440 | 44.8 |
| 7 | −1.26 | 0.10 | | | |
| 8 | 6.06 | 0.50 | | 1.7502 | 33.2 |
| 9 | 3.02 | 1.60 | | 1.5174 | 67.3 |
| 10 | −3.73 | 0.10 | | | |
| 11 | 3.78 | 2.20 | | 1.4875 | 70.4 |

-continued

| | | | | | |
|---|---|---|---|---|---|
| 12 | −2.99 | 0.50 | | 1.7508 | 32.4 |
| 13 | 56.93 | 5.13 | | | |
| 14 | ∞ | 0.40 | | 1.5163 | 64.1 |
| 15 | ∞ | 0.10 | | | |
| Image surface | ∞ | | | | |

ERFS [1]

| | |
|---|---|
| RY | ∞ |
| θ | 90.00 |
| R | −3.00 |

ERFS [2]

| | |
|---|---|
| RY | 2.56 |
| θ | 31.22 |
| R | −2.33 |

ERFS [3]

| | |
|---|---|
| RY | 4.88 |
| θ | 2.88 |
| R | −1.71 |

ERFS [4]

| | |
|---|---|
| RY | 1.75 |
| θ | 40.71 |
| R | −1.14 | eccentricity (1)

| | | | | | | | |
|---|---|---|---|---|---|---|---|
| X | 0.00 | Y | 0.00 | Z | 0.00 | | |
| α | 90.00 | β | 0.00 | γ | 0.00 | | | eccentricity (2)

| | | | | | | | |
|---|---|---|---|---|---|---|---|
| X | 0.00 | Y | 0.00 | Z | −0.03 | | |
| α | 0.00 | β | 0.00 | γ | 0.00 | | | eccentricity (3)

| | | | | | | | |
|---|---|---|---|---|---|---|---|
| X | 0.00 | Y | 0.00 | Z | −0.04 | | |
| α | 0.00 | β | 0.00 | γ | 0.00 | | | eccentricity (4)

| | | | | | | | |
|---|---|---|---|---|---|---|---|
| X | 0.00 | Y | 0.00 | Z | −1.22 | | |
| α | 0.00 | β | 0.00 | γ | 0.00 | | | eccentricity (5)

| | | | | | | | |
|---|---|---|---|---|---|---|---|
| X | 0.00 | Y | 0.00 | Z | −0.38 | | |
| α | 0.00 | β | 0.00 | γ | 0.00 | | | eccentricity (6)

| | | | | | | | |
|---|---|---|---|---|---|---|---|
| X | 0.00 | Y | 0.00 | Z | 1.77 | | |
| α | 0.00 | β | 0.00 | γ | 0.00 | | |

Direct view optical path

| Surface number | Radius of curvature | Plane gap | Eccentricity | Refractive index | Abbe number |
|---|---|---|---|---|---|
| object surface | ∞ | ∞ | | | |
| 1 | ∞ | 0.60 | | 1.5163 | 64.1 |
| 2 | 1.50 | 1.76 | | | |
| 3 | ERFS [5] | | eccentricity (7) | 1.8348 | 42.7 |
| 4 | ERFS [4] | | eccentricity (5) | | |
| 5 | ∞ (Stop) | 0.20 | eccentricity (6) | | |
| 6 | −0.89 | 0.80 | | 1.7440 | 44.8 |
| 7 | −1.26 | 0.10 | | | |
| 8 | 6.06 | 0.50 | | 1.7502 | 33.2 |
| 9 | 3.02 | 1.60 | | 1.5174 | 67.3 |
| 10 | −3.73 | 0.10 | | | |
| 11 | 3.78 | 2.20 | | 1.4875 | 70.4 |
| 12 | −2.99 | 0.50 | | 1.7508 | 32.4 |
| 13 | 56.93 | 5.13 | | | |
| 14 | ∞ | 0.40 | | 1.5163 | 64.1 |
| 15 | ∞ | 0.10 | | | |
| Image surface | ∞ | | | | |

ERFS [5]

| | |
|---|---|
| RY | 5.00 |
| θ | 5.04 |
| R | −0.44 |

ERFS [4]

| | |
|---|---|
| RY | 1.75 |
| θ | 40.71 |
| R | −1.14 | eccentricity (7)

| | | | | | | | |
|---|---|---|---|---|---|---|---|
| X | 0.00 | Y | 0.00 | Z | −1.33 | | |
| α | 0.00 | β | 0.00 | γ | 0.00 | | | eccentricity (5)

| | | | | | | | |
|---|---|---|---|---|---|---|---|
| X | 0.00 | Y | 0.00 | Z | −0.38 | | |
| α | 0.00 | β | 0.00 | γ | 0.00 | | | eccentricity (6)

| | | | | | | | |
|---|---|---|---|---|---|---|---|
| X | 0.00 | Y | 0.00 | Z | 1.77 | | |
| α | 0.00 | β | 0.00 | γ | 0.00 | | |

Example 2

Side view optical path

| Surface number | Radius of curvature | Plane gap | Eccentricity | Refractive index | Abbe number |
|---|---|---|---|---|---|
| Object surface | ∞ | ∞ | eccentricity (1) | | |
| 1 | ERFS [1] | | eccentricity (2) | 1.8348 | 42.7 |
| 2 | ASS [1] (RE) | | eccentricity (3) | 1.8348 | 42.7 |
| 3 | 11.26 (RE) | | eccentricity (4) | 1.8348 | 42.7 |
| 4 | ASS [1] | | eccentricity (3) | | |
| 5 | ∞ (Stop) | 0.10 | eccentricity (5) | | |
| 6 | −1.59 | 2.00 | | 1.7292 | 54.7 |
| 7 | −2.02 | 0.10 | | | |
| 8 | 4.80 | 1.00 | | 1.8467 | 23.8 |
| 9 | 2.52 | 2.50 | | 1.7440 | 44.8 |
| 10 | −12.02 | 3.62 | | | |
| 11 | ∞ | 0.40 | | 1.5163 | 64.1 |
| 12 | ∞ | 0.10 | | | |
| Image surface | ∞ | | | | |

ERFS [1]

| | |
|---|---|
| RY | ∞ |
| θ | 90.00 |
| R | −3.00 |

ASS [1]

| | |
|---|---|
| R | 3.25 |
| k | −7.5002e−1 | eccentricity (1)

| | | | | | | | |
|---|---|---|---|---|---|---|---|
| X | 0.00 | Y | 0.00 | Z | 0.00 | | |
| α | 90.00 | β | 0.00 | γ | 0.00 | | | eccentricity (2)

| | | | | | | | |
|---|---|---|---|---|---|---|---|
| X | 0.00 | Y | 0.00 | Z | −0.03 | | |
| α | 0.00 | β | 0.00 | γ | 0.00 | | | eccentricity (3)

| | | | | | | | |
|---|---|---|---|---|---|---|---|
| X | 0.00 | Y | 0.00 | Z | −0.91 | | |
| α | 0.00 | β | 0.00 | γ | 0.00 | | |

| eccentricity (4) | | | | | |
|---|---|---|---|---|---|
| X | 0.00 | Y | 0.00 | Z | −1.73 |
| α | 0.00 | β | 0.00 | γ | 0.00 |
| eccentricity (5) | | | | | |
| X | 0.00 | Y | 0.00 | Z | 0.55 |
| α | 0.00 | β | 0.00 | γ | 0.00 |

Direct view optical path

| Surface number | Radius of curvature | Plane gap | Eccentricity | Refractive index | Abbe number |
|---|---|---|---|---|---|
| Object surface | ∞ | ∞ | | | |
| 1 | ∞ | 0.80 | | 1.7292 | 54.7 |
| 2 | 4.61 | 3.57 | | | |
| 3 | 11.26 | | eccentricity (4) | 1.8348 | 42.7 |
| 4 | 3.25 | | eccentricity (3) | | |
| 5 | ∞ (Stop) | 0.10 | eccentricity (5) | | |
| 6 | −1.59 | 2.00 | | 1.7292 | 54.7 |
| 7 | −2.02 | 0.10 | | | |
| 8 | 4.80 | 1.00 | | 1.8467 | 23.8 |
| 9 | 2.52 | 2.50 | | 1.7440 | 44.8 |
| 10 | −12.02 | 3.62 | | | |
| 11 | ∞ | 0.40 | | 1.5163 | 64.1 |
| 12 | ∞ | 0.10 | | | |
| Image surface | ∞ | | | | |

| eccentricity (4) | | | | | |
|---|---|---|---|---|---|
| X | 0.00 | Y | 0.00 | Z | −1.73 |
| α | 0.00 | β | 0.00 | γ | 0.00 |
| eccentricity (3) | | | | | |
| X | 0.00 | Y | 0.00 | Z | −0.91 |
| α | 0.00 | β | 0.00 | γ | 0.00 |
| eccentricity (5) | | | | | |
| X | 0.00 | Y | 0.00 | Z | 0.55 |
| α | 0.00 | β | 0.00 | γ | 0.00 |

Example 3

Side view optical path

| Surface number | Radius of curvature | Plane gap | Eccentricity | Refractive index | Abbe number |
|---|---|---|---|---|---|
| Object surface | ∞ | ∞ | eccentricity (1) | | |
| 1 | ERFS [1] | | eccentricity (2) | 1.5163 | 64.1 |
| 2 | ASS [1] (RE) | | eccentricity (3) | 1.5163 | 64.1 |
| 3 | 15.47 (RE) | | eccentricity (4) | 1.5163 | 64.1 |
| 4 | ASS [1] | | eccentricity (3) | | |
| 5 | −8.96 | 0.55 | eccentricity (5) | 1.4875 | 70.4 |
| 6 | 0.88 | 0.50 | | | |
| 7 | ∞ (Stop) | 0.50 | | | |
| 8 | −3.52 | 0.50 | | 1.7552 | 27.6 |
| 9 | −25.30 | 1.50 | | 1.7440 | 44.8 |
| 10 | −2.04 | 0.10 | | | |
| 11 | 9.45 | 1.00 | | 1.8467 | 23.8 |
| 12 | 2.95 | 2.50 | | 1.6204 | 60.3 |
| 13 | −5.81 | 8.41 | | | |
| 14 | ∞ | 0.40 | | 1.5163 | 64.1 |
| 15 | ∞ | 0.10 | | | |
| Image surface | ∞ | | | | |

| ERFS [1] | |
|---|---|
| RY | ∞ |
| θ | 90.00 |
| R | −3.00 |

| ASS [1] | |
|---|---|
| R | 4.01 |
| k | −3.0163e−1 |

| eccentricity (1) | | | | | |
|---|---|---|---|---|---|
| X | 0.00 | Y | −5.00 | Z | 0.00 |
| α | 90.00 | β | 0.00 | γ | 0.00 |
| eccentricity (2) | | | | | |
| X | 0.00 | Y | 0.00 | Z | −0.03 |
| α | 0.00 | β | 0.00 | γ | 0.00 |
| eccentricity (3) | | | | | |
| X | 0.00 | Y | 0.00 | Z | −0.78 |
| α | 0.00 | β | 0.00 | γ | 0.00 |
| eccentricity (4) | | | | | |
| X | 0.00 | Y | 0.00 | Z | −1.37 |
| α | 0.00 | β | 0.00 | γ | 0.00 |
| eccentricity (5) | | | | | |
| X | 0.00 | Y | 0.00 | Z | 0.16 |
| α | 0.00 | β | 0.00 | γ | 0.00 |

Direct view optical path

| Surface number | Radius of curvature | Plane gap | Eccentricity | Refractive index | Abbe number |
|---|---|---|---|---|---|
| Object surface | ∞ | ∞ | | | |
| 1 | 8.69 | 0.80 | | 1.5163 | 64.1 |
| 2 | 1.65 | 2.86 | | | |
| 3 | 15.47 | | eccentricity (4) | 1.8348 | 42.7 |
| 4 | 4.01 | | eccentricity (3) | | |
| 5 | −8.96 | 0.55 | eccentricity (5) | 1.4875 | 70.4 |
| 6 | 0.88 | 0.50 | | | |
| 7 | ∞ (Stop) | 0.50 | | | |
| 8 | −3.52 | 0.50 | | 1.7552 | 27.6 |
| 9 | −25.30 | 1.50 | | 1.7440 | 44.8 |
| 10 | −2.04 | 0.10 | | | |
| 11 | 9.45 | 1.00 | | 1.8467 | 23.8 |
| 12 | 2.95 | 2.50 | | 1.6204 | 60.3 |
| 13 | −5.81 | 8.41 | | | |
| 14 | ∞ | 0.40 | | 1.5163 | 64.1 |
| 15 | ∞ | 0.10 | | | |
| Image surface | ∞ | | | | |

| eccentricity (4) | | | | | |
|---|---|---|---|---|---|
| X | 0.00 | Y | 0.00 | Z | −1.37 |
| α | 0.00 | β | 0.00 | γ | 0.00 |
| eccentricity (3) | | | | | |
| X | 0.00 | Y | 0.00 | Z | −0.78 |
| α | 0.00 | β | 0.00 | γ | 0.00 |
| eccentricity (5) | | | | | |
| X | 0.00 | Y | 0.00 | Z | 0.16 |
| α | 0.00 | β | 0.00 | γ | 0.00 |

Example 4

Side view optical path

| Surface number | Radius of curvature | Plane gap | Eccentricity | Refractive index | Abbe number |
|---|---|---|---|---|---|
| Object surface | ∞ | ∞ | eccentricity (1) | | |
| 1 | ERFS [1] | | eccentricity (2) | 1.5163 | 64.1 |
| 2 | ASS [1] (RE) | | eccentricity (3) | 1.5163 | 64.1 |
| 3 | 14.19 (RE) | | eccentricity (4) | 1.5163 | 64.1 |
| 4 | ASS [1] | | eccentricity (3) | | |
| 5 | −3.01 | 0.55 | eccentricity (5) | 1.4875 | 70.4 |
| 6 | 1.10 | 0.50 | | | |
| 7 | ∞ (Stop) | 0.50 | | | |
| 8 | −4.75 | 0.50 | | 1.7209 | 29.1 |
| 9 | 43.27 | 1.50 | | 1.7440 | 44.8 |
| 10 | −2.26 | 0.10 | | | |
| 11 | 16.57 | 1.00 | | 1.8467 | 23.8 |
| 12 | 3.66 | 2.50 | | 1.6204 | 60.3 |
| 13 | −4.87 | 9.25 | | | |
| 14 | ∞ | 0.40 | | 1.5163 | 64.1 |
| 15 | ∞ | 0.10 | | | |
| Image surface | ∞ | | | | |

ERFS [1]

| | |
|---|---|
| RY | ∞ |
| θ | 90.00 |
| R | −4.00 |

ASS [1]

| | |
|---|---|
| R | 4.40 |
| k | −7.3106E−1 | eccentricity (1)

| | | | | | | | |
|---|---|---|---|---|---|---|---|
| X | 0.00 | Y | 0.00 | Z | 0.00 | | |
| α | 90.00 | β | 0.00 | γ | 0.00 | | | eccentricity (2)

| | | | | | | | |
|---|---|---|---|---|---|---|---|
| X | 0.00 | Y | 0.00 | Z | −0.02 | | |
| α | 0.00 | β | 0.00 | γ | 0.00 | | | eccentricity (3)

| | | | | | | | |
|---|---|---|---|---|---|---|---|
| X | 0.00 | Y | 0.00 | Z | −1.12 | | |
| α | 0.00 | β | 0.00 | γ | 0.00 | | | eccentricity (4)

| | | | | | | | |
|---|---|---|---|---|---|---|---|
| X | 0.00 | Y | 0.00 | Z | −2.28 | | |
| α | 0.00 | β | 0.00 | γ | 0.00 | | | eccentricity (5)

| | | | | | | | |
|---|---|---|---|---|---|---|---|
| X | 0.00 | Y | 0.00 | Z | 0.06 | | |
| α | 0.00 | β | 0.00 | γ | 0.00 | | |

Direct view optical path

| Surface number | Radius of curvature | Plane gap | Eccentricity | Refractive index | Abbe number |
|---|---|---|---|---|---|
| Object surface | ∞ | ∞ | | | |
| 1 | 9.42 | 0.80 | | 1.5163 | 64.1 |
| 2 | 2.13 | 2.35 | | | |
| 3 | −4.29 | 0.80 | | 1.5163 | 64.1 |
| 4 | −3.86 | 2.38 | | | |
| 5 | 14.19 | 0.00 | eccentricity (5) | 1.8348 | 42.7 |
| 6 | ASS [1] | 0.00 | eccentricity (4) | | |
| 7 | −3.01 | 0.55 | eccentricity (6) | 1.4875 | 70.4 |
| 8 | 1.10 | 0.50 | | | |
| 9 | ∞ (Stop) | 0.50 | | | |
| 10 | −4.75 | 0.50 | | 1.7209 | 29.1 |
| 11 | 43.27 | 1.50 | | 1.7440 | 44.8 |
| 12 | −2.26 | 0.10 | | | |
| 13 | 16.57 | 1.00 | | 1.8467 | 23.8 |
| 14 | 3.66 | 2.50 | | 1.6204 | 60.3 |
| 15 | −4.87 | 9.25 | | | |
| 16 | ∞ | 0.40 | | 1.5163 | 64.1 |
| 17 | ∞ | 0.10 | | | |
| Image surface | ∞ | | | | |

ASS [1]

| | |
|---|---|
| R | 4.40 |
| k | −7.3106e−1 | eccentricity [4]

| | | | | | | | |
|---|---|---|---|---|---|---|---|
| X | 0.00 | Y | 0.00 | Z | −2.28 | | |
| α | 0.00 | β | 0.00 | γ | 0.00 | | | eccentricity [3]

| | | | | | | | |
|---|---|---|---|---|---|---|---|
| X | 0.00 | Y | 0.00 | Z | −1.12 | | |
| α | 0.00 | β | 0.00 | γ | 0.00 | | | eccentricity [5]

| | | | | | | | |
|---|---|---|---|---|---|---|---|
| X | 0.00 | Y | 0.00 | Z | 0.06 | | |
| α | 0.00 | β | 0.00 | γ | 0.00 | | |

Example 5

Side view optical path

| Surface number | Radius of curvature | Plane gap | Eccentricity | Refractive index | Abbe number |
|---|---|---|---|---|---|
| Object surface | ∞ | ∞ | eccentricity (1) | | |
| 1 | ERFS [1] | | eccentricity (2) | 1.5163 | 64.1 |
| 2 | ASS [1] (RE) | | eccentricity (3) | 1.5163 | 64.1 |
| 3 | ASS [2] (RE) | | eccentricity (4) | 1.5163 | 64.1 |
| 4 | ASS [1] | | eccentricity (3) | | |
| 5 | −3.66 | 0.55 | eccentricity (5) | 1.7440 | 44.8 |
| 6 | −2.96 | 0.50 | | | |
| 7 | ∞ (Stop) | 3.00 | | | |
| 8 | ideal lens | 3.58 | | | |
| Image surface | ∞ | | | | |

ERFS [1]

| | |
|---|---|
| RY | ∞ |
| θ | 90.00 |
| R | −4.00 |

ASS [1]

| | |
|---|---|
| R | 5.11 |
| k | 1.3753E+0 |

ASS [2]

| | |
|---|---|
| R | 13.09 |
| k | 0.0000 | eccentricity (1)

| | | | | | | | |
|---|---|---|---|---|---|---|---|
| X | 0.00 | Y | −5.00 | Z | 0.00 | | |
| α | 90.00 | β | 0.00 | γ | 0.00 | | | eccentricity (2)

| | | | | | | | |
|---|---|---|---|---|---|---|---|
| X | 0.00 | Y | −4.00 | Z | −0.04 | | |
| α | 90.00 | β | 0.00 | γ | 0.00 | | |

-continued eccentricity (3)

| X | 0.00 | Y | 0.00 | Z | −0.87 |
|---|------|---|------|---|-------|
| α | 0.00 | β | 0.00 | γ | 0.00  | eccentricity (4)

| X | 0.00 | Y | 0.00 | Z | −1.64 |
|---|------|---|------|---|-------|
| α | 0.00 | β | 0.00 | γ | 0.00  | eccentricity (5)

| X | 0.00 | Y | 0.00 | Z | 1.17 |
|---|------|---|------|---|------|
| α | 0.00 | β | 0.00 | γ | 0.00 |

Direct view optical path

| Surface number | Radius of curvature | Plane gap | Eccentricity | Refractive index | Abbe number |
|---|---|---|---|---|---|
| Object surface | ∞ | ∞ | | | |
| 1 | 205.85 | 0.80 | | 1.5163 | 64.1 |
| 2 | 2.32 | 2.30 | | | |
| 3 | ASS [2] (RE) | | eccentricity (4) | 1.5163 | 64.1 |
| 4 | ASS [1] | | eccentricity (3) | | |
| 5 | −3.66 | 0.55 | eccentricity (5) | 1.7440 | 44.8 |
| 6 | −2.96 | 0.50 | | | |
| 7 | ∞ (Stop) | 3.00 | | | |
| 8 | ideal lens | 3.58 | | | |
| Image surface | ∞ | | | | |

ASS [1]

| R | 5.11     |
|---|----------|
| k | 1.3753E+0 |

ASS [2]

| R | 13.09  |
|---|--------|
| k | 0.0000 | eccentricity (3)

| X | 0.00 | Y | 0.00 | Z | −0.87 |
|---|------|---|------|---|-------|
| α | 0.00 | β | 0.00 | γ | 0.00  | eccentricity (4)

| X | 0.00 | Y | 0.00 | Z | −1.64 |
|---|------|---|------|---|-------|
| α | 0.00 | β | 0.00 | γ | 0.00  | eccentricity (5)

| X | 0.00 | Y | 0.00 | Z | 1.17 |
|---|------|---|------|---|------|
| α | 0.00 | β | 0.00 | γ | 0.00 |

Examples 1 through 5 represent the following values for D, Dr and D/Dr, where D is the external dimension of the optical element Dr is the external dimension of the image of the reflective optical path.

|      | Example 1 | Example 2 | Example 3 | Example 4 | Example 5 |
|------|-----------|-----------|-----------|-----------|-----------|
| D    | 6.00      | 6.00      | 6.00      | 8.00      | 8.00      |
| Dr   | 4.96      | 4.90      | 4.94      | 4.94      | 4.99      |
| D/Dr | 1.21      | 1.22      | 1.21      | 1.62      | 1.60      |

Now, other examples of optical system according to the present invention will be described below.

Figure 19:
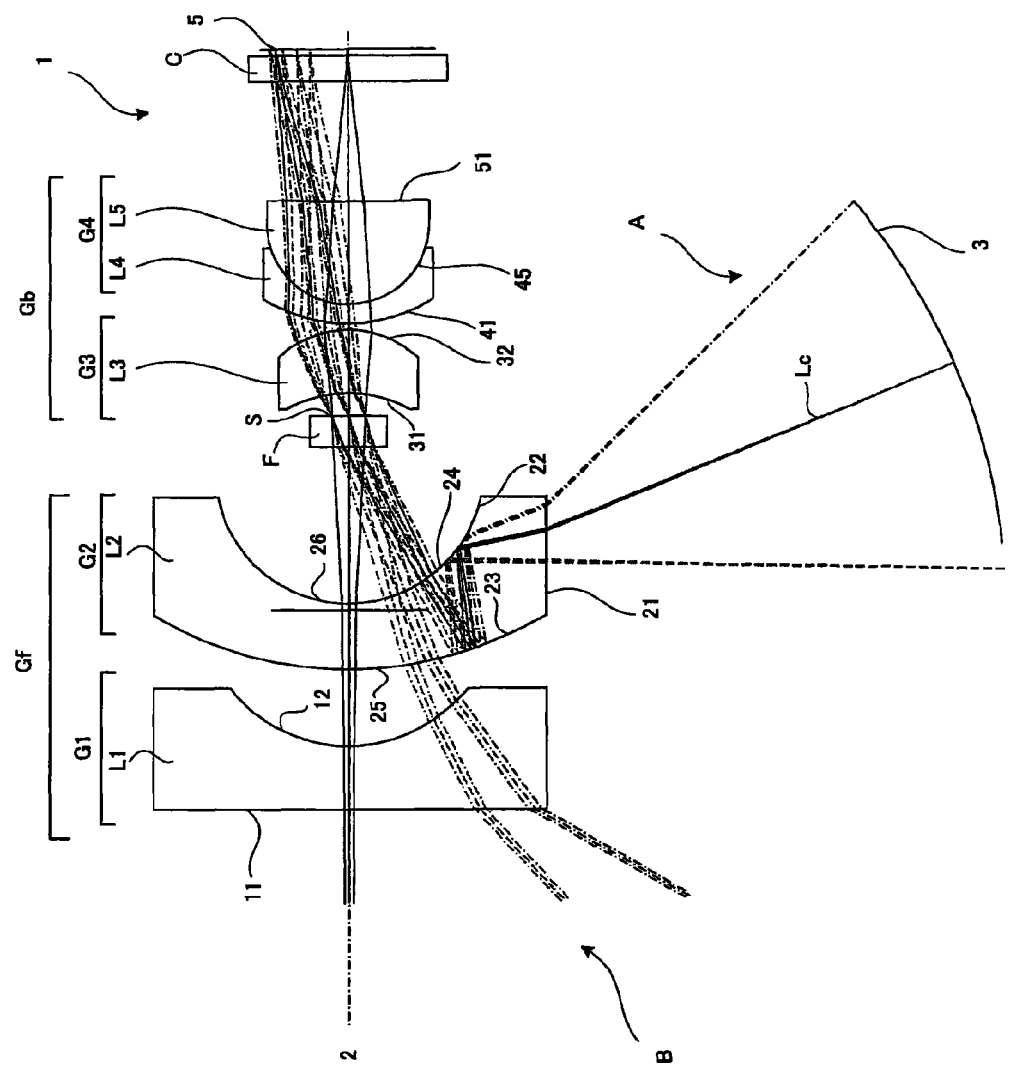
FIG. 19 is a schematic cross sectional view of the optical system of Example 6 of the present invention taken along the central axis thereof.

FIG. 19 is a schematic cross sectional view of the optical system 1 of Example 6 of the present invention, which will be described in greater detail hereinafter, taken along the central axis (axis of rotational symmetry) 2 thereof. Note that, while the optical system is described below in terms of image formation optical system, it is also applicable to a projection optical system by using the optical path reversely.

The optical system 1 of the present invention includes a front group Gf that is rotationally symmetric relative to central axis 2 and has negative power, an aperture S and a back group Gb having positive power and can form or project an image without forming an intermediate image on any optical path.

The optical system 1 of Example 6 includes a front group Gf that is rotationally symmetric relative to central axis 2 and a back group Gb that is also rotationally symmetric relative to the central axis 2. The front group Gf of the optical system is formed by a first group G1 having negative power and a second group G2 that is an optical path synthesizing optical system and the back group Gb if the optical system arranged at the back of the aperture S is formed by a third group G3 having positive power and a fourth group G4 that is a cemented lens having positive power.

In this example, the second group G2 of the front group Gf has a side view optical path A and a direct view optical path B and the third group G3 and the fourth group G4 of the back group Gb have an effect of forming the aerial image synthesized by the second group G2. It operates to form a circle for the image at the image center on the central axis 2 by means of the direct view optical path B and a different annular image of the side view optical path A at the outside of the circle.

The parallel flat plate arranged near the aperture S typically operates as a filter F. The parallel flat plate near the image plane 5 is typically a cover glass C for the imaging element.

The optical system becomes of the so-called retro-focus type when the front group Gf is made negative and the back group is made positive. Such an arrangement is effective particularly when a wide view angle needs to be secured for observation relative to the direct view optical path B for an object point on the central axis 2.

The front group Gf has an effect of synthetically combining the direct view optical path B for forming or projecting an image on the central axis 2 by a transmission effect and a side view optical path A for forming or projecting an omni-directional image in a direction substantially orthogonal to the central axis 2 by a reflection effect.

The front group Gf includes a transparent medium L2 that by turn has a first transmissive surface 21 arranged at the external side vis-a-vis the side view object surface 3, a first reflective surface 22 arranged at the side of the central axis 2 relative to the first transmissive surface 21, a second reflective surface 23 arranged at the side opposite to the image plane 5 relative to the first reflective surface 22, a second transmissive surface 24 arranged at the side of the image plane 5 relative to the second reflective surface 23, a third transmissive surface 25 and a fourth transmissive surface 26 arranged at the side of the image plane 5 relative to the third transmissive surface 25, the third transmissive surface 25 and the fourth transmissive surface 26 being arranged opposite to the direct view object surface.

The flux of light striking the transparent medium L2 enters the transparent medium L2 to proceed along the side view optical path A by way of the first transmissive surface 21 so as to be reflected to the side opposite to the image plane 5 by the first reflective surface 22 and then to the side of the image plane 5 by the second reflective surface 23 to form a substantially Z-shaped optical path before going out from the transparent medium L2 to the outside at the side of the image plane 5 by way of the second transparent surface 24 in the order of forward ray tracing and along the direct view optical path B by way of the third transmissive surface 25 before going out from the transparent medium L2 to the outside at side of the image plane 5 by way of the fourth transmissive surface 26.

If the ray of light passing through the center of the aperture S is referred to as a central principal ray of light Lc, the central principal ray of light Lc entering the first transmissive surface 21 is inclined to the side of the image plane 5 from the line orthogonal to the central axis 2. With this arrangement, it is possible to provide a wide view angle for observation at side of the image plane 5 relative to a direction orthogonal to the central axis 2.

Additionally, in the side view optical path A, both the first reflective surface 22 and the second reflective surface 23 are preferably formed by using a concave surface directed to the aperture S. With this arrangement, it is possible to arrange the first reflective surface 22 having negative power and the second reflective surface 23 having positive power in the above-mentioned order from the object side. Then, it is possible to provide a wide view angle for observation and, at the same time, suppress and minimize the comatic aberration.

Still additionally, if the center of the view angle of the meridional cross section of an omni-directional image is referred to as the central view angle and the ray of light passing through the center of the aperture S is referred to as a central principal ray of light Lc, it is important that the position at which the central principal ray of light Lc strikes the first reflective surface is located at the object side relative to the aperture S. This is an important requirement to be satisfied in order to make the external dimensions of the optical system 1 small and the external dimension of the first reflective surface 22 can be made small by arranging the first reflective surface at the object side relative to the aperture S. This is because the part for rigidly anchoring the optical parts of the back group Gb and the first reflective surface 22 interfere with each other when the first reflective surface 22 is arranged near the aperture S or at the image side relative to the aperture S and then the external dimension of the first reflective surface 22 has inevitably to be made large.

The first reflective surface 22 does not require any coating when it is made to have a total reflection effect. Then, the optical system can be prepared inexpensively.

The first reflective surface and the second reflective surface can be arranged as back surface mirrors when the first transmissive surface 21 is arrange at the opposite side of the image plane relative to the first reflective surface 22. Then, it is possible to suppress and minimize the eccentric aberration.

Preferably, the first reflective surface 22 and the second transmissive surface 24 or the first reflective surface 22 and the fourth transmissive surface 26 are formed at the same position with the same surface shape. Then, the same surface shape can be used for the two optical paths to make it possible to minimize the region where no image is formed between the circular image of the object point on the central axis 2 formed by the direct view optical path B and the annular image formed by the side view optical path A. Such an arrangement is advantageous from the viewpoint of effectively utilizing pixels.

Preferably, the third transmissive surface 25 of the direct view optical path B and the second reflective surface 23 of the side view optical path B (A?) are formed at the same position with the same surface shape. Then, the same surface shape can be used for the two optical paths to make it possible to facilitate the processing thereof.

Preferably, the optical path from the first reflective surface 22 to the second reflective surface 23 is in a direction divergent relative to the central axis 2 to make it possible to provide a wide view angle for observation at the side of the image plane 5 relative to the direction orthogonal to the central axis.

Preferably, at least one of the surfaces that the front group Gf has is formed by an extended rotary free curved surface formed by rotating a line segment of arbitrary shape having no plane of symmetry around the central axis 2. Then, the distortions at and near the view angle can be corrected as a result of having no plane of symmetry.

Preferably, at least one of the surfaces that the front group Gf has is formed by a line segment of arbitrary shape including one or more than one odd-number-th degree terms. Then, it is possible to provide a shape that is vertically asymmetric relative to the center of the view angle due to the odd-number-th degree terms to a great advantage of correcting aberrations.

Now, Examples 6 through 10 of optical system of visual display apparatus according to the present invention will be described below. The parameters of the optical systems of these examples will be described hereinafter.

Figure 18:
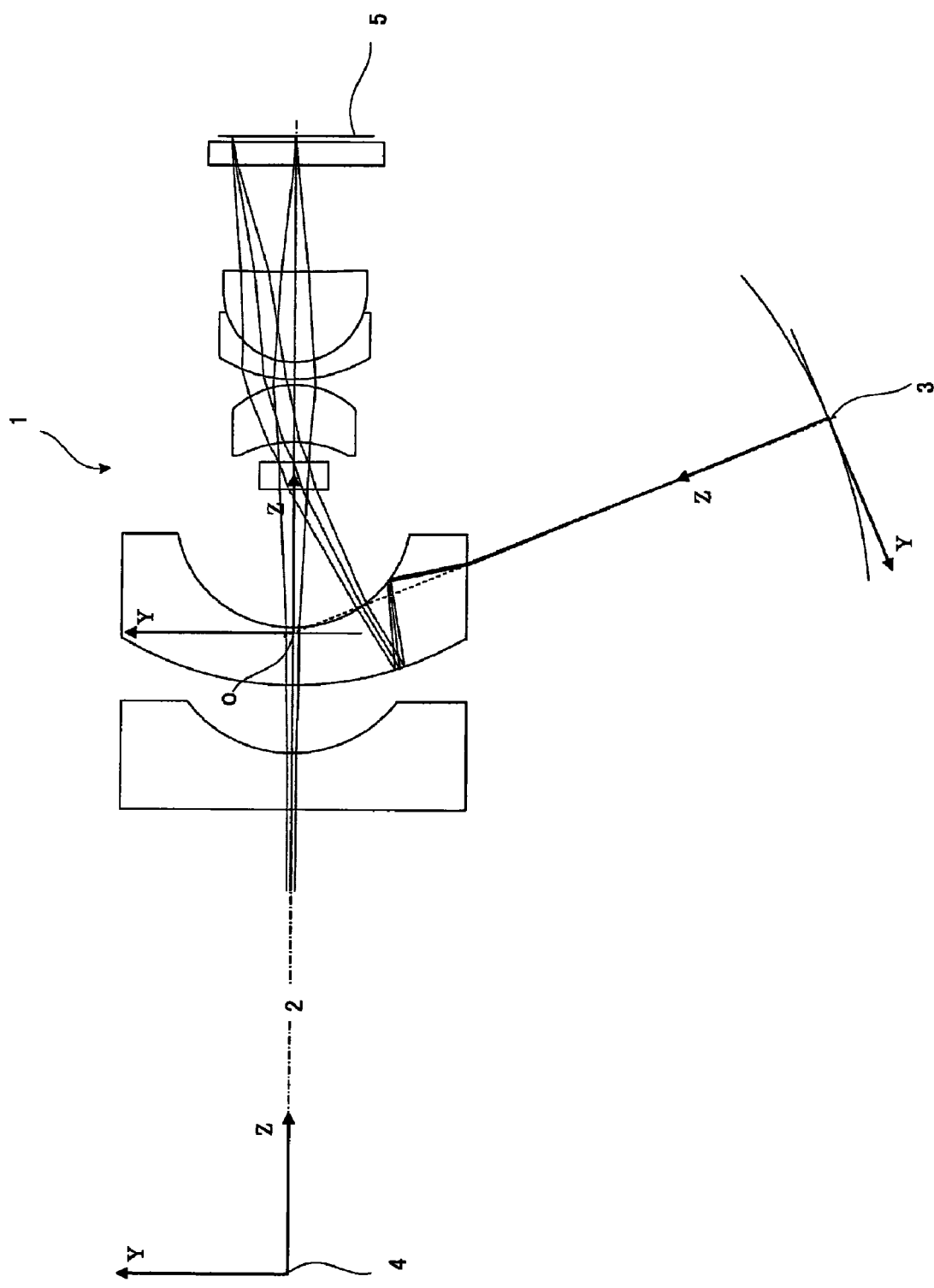
FIG. 18 is a schematic illustration of the coordinate system of another embodiment of optical system according to the present invention.

As coordinate system in forward ray tracing, for instance, the point of intersection of a prolonged line of the central principal ray of light proceeding from the side view object surface 3 toward the first surface and the central axis 2 is taken as origin O of eccentric optical surface and the direction orthogonal to the central axis 2 and of moving toward the side opposite to the side view object surface 3 as viewed from the central axis 2 is taken as a Y-axis positive direction as illustrated in FIG. 18, whereas the surface plane of the sheet of FIG. 18 is taken as a Y-Z plane. Then, the direction of moving toward the image plane 5 in FIG. 18 is taken as a Z-axis positive direction and the axis that constitutes a right hand orthogonal coordinate system with the Y-axis and the Z-axis is taken as an X-axis positive direction. Incidentally, a numerical value 4 indicates a direct view object surface.

As for the eccentric surface, the eccentricity from the origin O of the above optical system 1 that is used for defining the coordinate system that by turn defines the surface (as expressed by X, Y and Z respectively in the X-axis direction, the Y-axis direction and the Z-axis direction) and the angles of inclination of the planes extending respectively through the X-axis, the Y-axis and the Z-axis in the coordinate system that is defined by using the origin O of the optical system 1 ($\alpha$, $\beta$ and $\gamma$ (°) respectively) are given. Note that $\alpha$ and $\beta$ are taken as positive respectively in the counterclockwise directions relative to the positive direction of the X-axis and that of the Y-axis and $\gamma$ is taken as positive in the clockwise direction relative to the position direction of the Z-axis. Also note that each of the planes is rotated around the central axis thereof by $\alpha$, $\beta$ and $\gamma$ in such a way that the coordinate system that defines the planes is rotated firstly counterclockwise by $\alpha$ around the X-axis of the coordinate system that is defined by using the origin of the optical system and then the coordinate system obtained by rotating the initial coordinate system is rotated counterclockwise by $\beta$ around the Y-axis thereof. Then, finally, the coordinate system obtained by rotating the second coordinate system is rotated clockwise by $\gamma$ around the Z-axis thereof.

When a specific plane and the subsequent plane of the optical acting planes that the optical system of each of the examples includes form a coaxial optical system, the plane gap is given. Otherwise, the radius of curvature of each plane, the refractive index of the medium and the Abbe number are given according to the common practice.

All the terms relating to aspheric planes that are not described in the data on the constituent parameters that will be described hereinafter are equal to 0. The refractive index and the Abbe number relative to d-lines (wavelength: 587.56 nm) are given. The unit of length is mm. The eccentricity of each plane is expressed by the eccentricity from the reference plane as described above.

An aspheric plane is a rotationally symmetric defined by the formula represented below.

$$Z=(Y^2/R)/[1+\{1=(1+k)Y^2/R^2\}^{1/2}]+aY^4+bY^6+cY^8+dY^{10} \quad (a)$$

provided that Z is selected as an axis and Y denotes a direction perpendicular to the axis. In the above formula, R is the near-axis radius of curvature, k is the conic constant and a, b, c, d, . . . are respectively the aspheric surface coefficients of the fourth degree, the sixth degree, the eighth degree, the tenth degree and so on. The Z-axis of the above defining formula operates as the axis of a rotationally symmetric aspheric surface.

An extended rotary free curved surface is a rotationally symmetric surface given by the following definition.

Firstly, a curved line (b) that passes through the origin on the Y-Z coordinate plane as illustrated in FIG. 2 is defined.

$$Z = (Y^2/RY)/\left[1+\{1-(C_1+1)Y^2/RY^2\}^{1/2}\right] + C_2Y + C_3Y^2 + C_4Y^3 + \quad (b)$$
$$C_5Y^4 + C_6Y^5 + C_7Y^6 + \ldots + C_{21}Y^{20} + \ldots + C_{n+1}Y^n + \ldots$$

Then, curbed line F(Y) is defined by rotating the curbed line (b) by angle θ(°), which is positive when it is rotated counterclockwise, facing in the positive direction of the X-axis. The curved line F(Y) also passes through the origin on the Y-Z coordinate plane.

The curved line F(Y) is translated in the direction of the positive direction of the Y-axis by distance R (in the negative direction of the Y-axis when it represents a negative value) and subsequently the translated curved line is rotated around the Z-axis to form a rotationally symmetric surface, which is an extended rotary free curved surface.

Then, as a result, the extended rotary free curved surface produces a free curved surface (free curved line) in the Y-Z plane and a circle of radius |R| in the X-Y plane.

From the above definition, the Z-axis operates as the axis (the axis of rotational symmetry) of the extended rotary free curved surface.

In the above formula (b), RY is the radius of curvature of the sphere term in the Y-Z cross section, $C_1$ is the conic constant and $C_2, C_3, C_4, C_5, \ldots$ are respectively the aspheric coefficients of the first degree, the second degree, the third degree, the fourth degree and so on.

Note that a surface of circular cone whose central axis is parallel to the Y-axis is given as an extended rotary free curved surface with RY=∞, $C_1, C_2, C_3, C_4, C_5, \ldots$ =0, θ=(the angle of inclination of the surface of circular cone) and R=(the radius of the bottom in the X-Z plane).

All the terms relating to aspheric planes that are not described in the data on the constituent parameters that will be described hereinafter are equal to 0. The refractive index and the Abbe number relative to d-lines (wavelength: 587.56 nm) are given. The unit of length is mm. The eccentricity of each plane is expressed by the eccentricity from the reference plane as described above.

Figure 20:
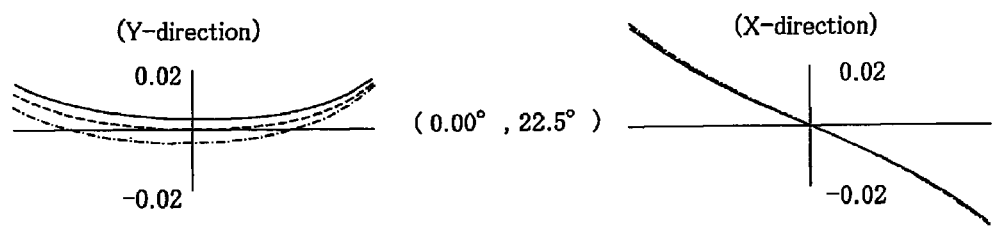
FIG. 20 is a schematic illustration of the transverse aberrations of the overall optical system of Example 6 on the side view optical path thereof.
Figure 20:
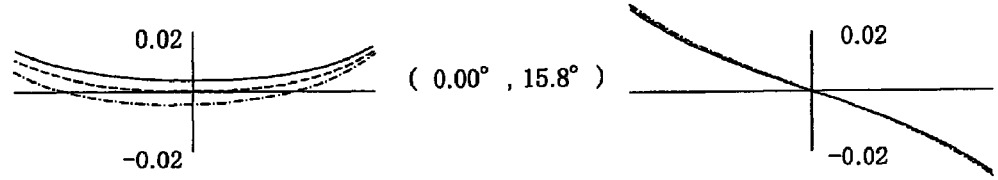
Figure 20:
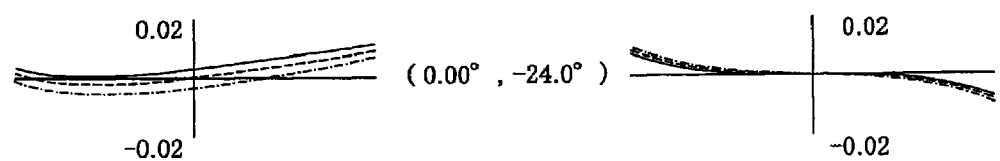
Figure 20:
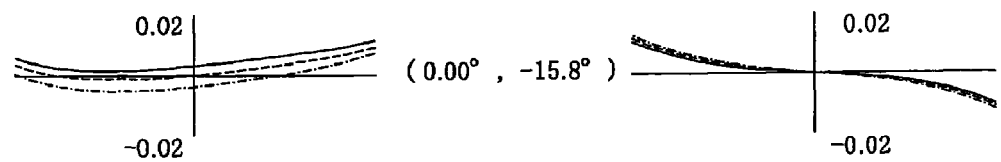
Figure 20:
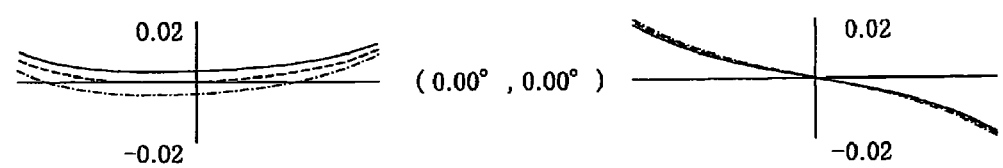
Figure 21:
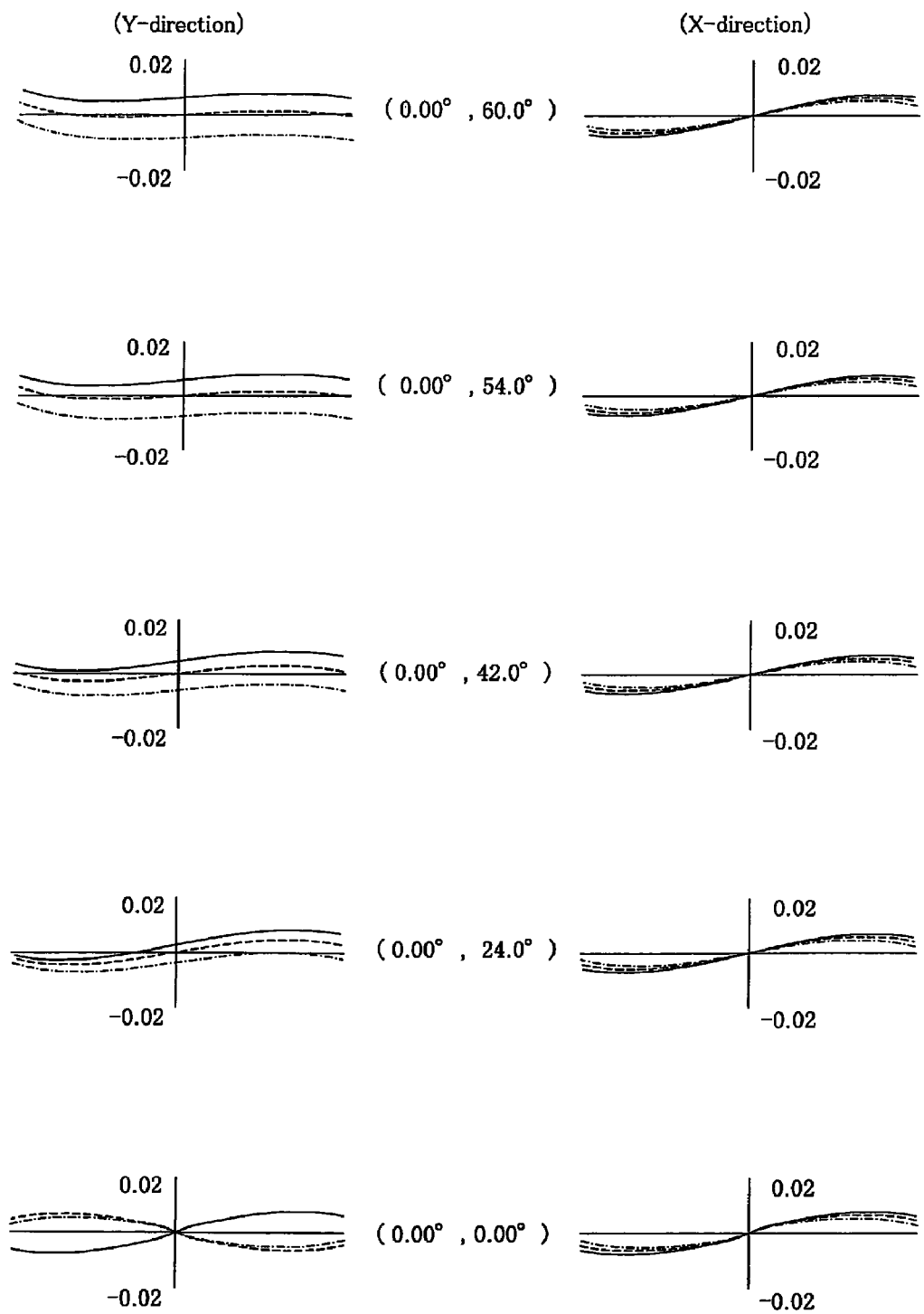
FIG. 21 is a schematic illustration of the transverse aberrations of the overall optical system of Example 6 on the direct view optical path thereof.

FIG. 19 is a schematic cross sectional view of the optical system 1 of Example 6 taken along the central axis 2 thereof. FIG. 20 is a schematic illustration of the transverse aberrations of the overall optical system of this example on the side view optical path A thereof. FIG. 21 is a schematic illustration of the transverse aberrations of the overall optical system of this example on the direct view optical path B thereof. In each of the views representing the transverse aberrations, each pair of angle values represented at the center includes (the view angle in the horizontal direction, the view angle in the vertical direction). The transverse aberrations in the Y direction (the meridional direction) and those in the X-direction (the sagittal direction) are also given. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, each of the transmissive surfaces and the reflective surfaces that are rotationally symmetric relative to the central axis 2 of the optical system 1 and have a refractive index greater than 1 is designed as an extended rotary free curved surface but as equivalent to a spherical surface when the extended rotary free curved surface is orthogonal to a rotationally symmetric surface and does not involve any term of higher degree.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group Gf includes a first group G1 and a second group G2, while the back group Gb includes a third group G3 and a fourth group G4.

The first group G1 is formed by a transparent medium L1 that is rotationally symmetric relative to the central axis 2 and represents a refractive index greater than 1. The transparent medium L1 has a direct view first transmissive surface 11 whose radius of curvature is infinity and a direct view second transmissive surface 12 that is arranged at the side of the image plane 5 relative to the direct view first transmissive surface 11 and formed by a spherical surface and has negative power.

The second group G2 is formed by a transparent medium L2 that is rotationally symmetric around the central axis 2 and has a refractive index greater than 1. It is an optical path synthesizing optical system for synthetically combining the side view optical path A and the direct view optical path B. The transparent medium L2 has a cylindrical side view first transmissive surface 21 that is arranged at the external side vis-a-vis the side view object surface 3 and parallel to the Z-axis so as to operate as a first transmissive surface, a side view first reflective surface 22 that is formed by a spherical surface in the inside of the transparent medium L2 at the side of the central axis 2 relative to the side view first transmissive surface 21 and has negative power so as to operate as a first reflective surface, a side view second reflective surface 23 that is formed by a spherical surface in the inside of the transparent medium L2 at the side opposite to the image plane 5 as viewed from the side view first reflective surface 22 and has positive power and a side view second transmissive surface 24 that is formed by a spherical surface and arranged at the side of the image plane 5 relative to the side view second reflective surface 23 operating as the second reflective surface and has negative power so as to operate as second transmissive surface as well as a direct view third transmissive surface 25 that is formed by a spherical surface and has positive power so as to operate as a third transmissive surface and a direct view fourth transmissive surface 26 that is formed by a spherical surface and arranged at the side of the image plane 5 relative to the direct view third transmissive surface 25 and has negative power so as to operate as a fourth transmissive surface. The side view second transmissive surface 24 and the direct view fourth transmissive surface 26 are the same surface.

The third group G3 is formed by a positive meniscus lens L3 with its convex surface directed to the image plane 5 and has a common first transmissive surface 31 and a common second transmissive surface 32 arranged at the side of the image plane 5 relative to the common first transmissive surface 31.

The fourth group G4 is formed by a cemented lens of a negative meniscus lens L4 with its concave surface directed to the image plane and a positive meniscus lens L5 with its concave surface directed to the image plane and has a common third transmissive surface 41, a cementing surface 45 arranged at the side of the image plane 5 relative to the common third transmissive surface 41 and a common fourth transmissive surface 51 arranged at the side of the image plane 5 relative to the cementing surface 45.

The optical system 1 forms a side view optical path A and a direct view optical path B. As for the side view optical path A, the flux of light entering it from the side view object surface 3 at the side of the optical system 1 proceeds sequentially by way of the second group G2 of the front group Gf and the back group Gb and forms an annular image off the central axis 2 of the image plane 5 extending perpendicularly relative to the central axis 2. As for the direct view optical path B, the flux of light entering it from the direct view object surface near the central axis 2 of the optical system 1 proceeds sequentially by way of the front group Gf and the back group Gb and forms a circular image near the central axis 2 of the image plane 5 extending perpendicularly relative to the central axis 2.

The flux of light entering the optical system 1 from a lateral side of the optical system 1 to proceed along the side view optical path A goes into the transparent medium L2 of the second group G2 of the front group Gf by way of the side view first transmissive surface 21 and is reflected by the side view first reflective surface 22 at the side of the central axis 2 to the side opposite to the image plane 5 and then by the side view second reflective surface 23 to the side of the image plane 5 to form a substantially Z-shaped optical path before going out from the transparent medium L2 to the outside by way of the side view second transmissive surface 24.

Subsequently, the flux of light goes into the positive meniscus lens L3 of the third group G3 of the back group Gb at the opposite side relative to the central axis 2 by way of the aperture S arranged coaxially with the central axis 2 between the front group Gf and the back group Gb to operate as a stop and the common first transmissive surface 31 and then goes out from the common second transmissive surface 32. Thereafter, it goes into the negative meniscus lens L4 of the fourth group G4 by way of the common third transmissive surface 41 and goes out from the common fourth transmissive surface 51 of the positive meniscus lens L5 by way of the cementing surface 45 to form an image at a predetermined radial position off the central axis 2 of the image plane 5.

The flux of light entering the optical system 1 to proceed along the direct view optical path B goes into the transparent medium L1 of the first group G1 of the front group Gf by way of the direct view first transmissive surface 11 and goes out from the transparent medium L1 by way of the direct view second transmissive surface 12 arranged at the side of the image plane 5 relative to the direct view first transmissive surface 11. Thereafter, it goes into the transparent medium L2 of the second group G2 by way of the direct view third transmissive surface 25 and goes out from the transparent medium L2 by way of the direct view fourth transmissive surface 26 arranged at the side of the image plane 5 relative to the direct view third transmissive surface 25.

Subsequently, the flux of light goes into the positive meniscus lens L3 of the third group G3 of the back group Gb by way of the aperture S arranged coaxially with the central axis 2 between the front group Gf and the back group Gb 2 to operate as a stop and the common first transmissive surface 31 and then goes out from the common second transmissive surface 32. Thereafter, it goes into the negative meniscus lens L4 of the fourth group G4 that is formed by a cemented lens by way of the common third transmissive surface 41 and goes out from the common fourth transmissive surface 51 of the positive meniscus lens L5 by way of the cementing surface 45 to form an image on the central axis 2 of the image plane 5.

The specifications of Example 6 are as follows.

| view angle (side view) | 89.5° to 135° |
|---|---|
| view angle (direct view) | 0° to 60° |
| stop diameter | ø0.5 mm |
| image size (side view) | ø2.00 to ø2.37 |
| (direct view) | ø1.56 |

Figure 22:
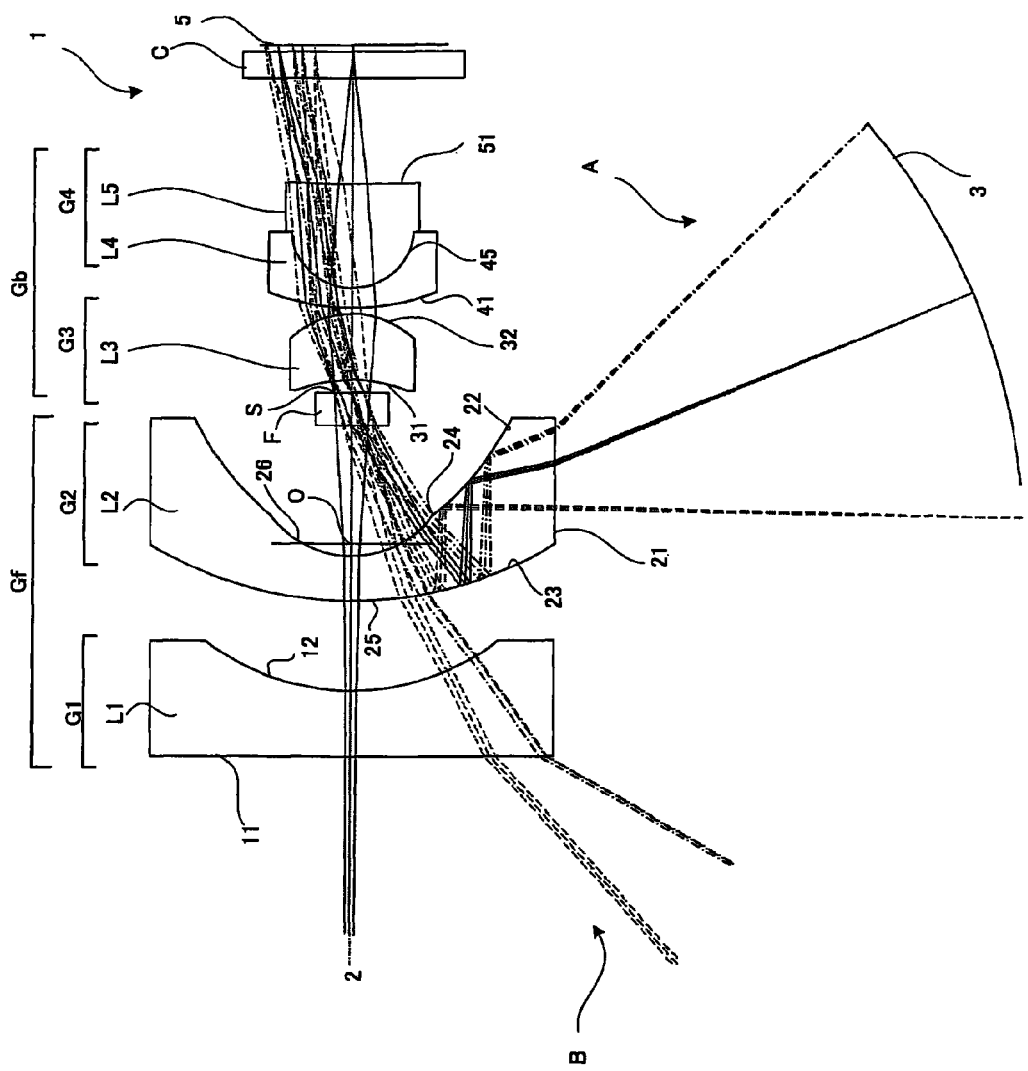
FIG. 22 is a schematic cross sectional view of the optical system of Example 7 of the present invention taken along the central axis thereof.
Figure 23:
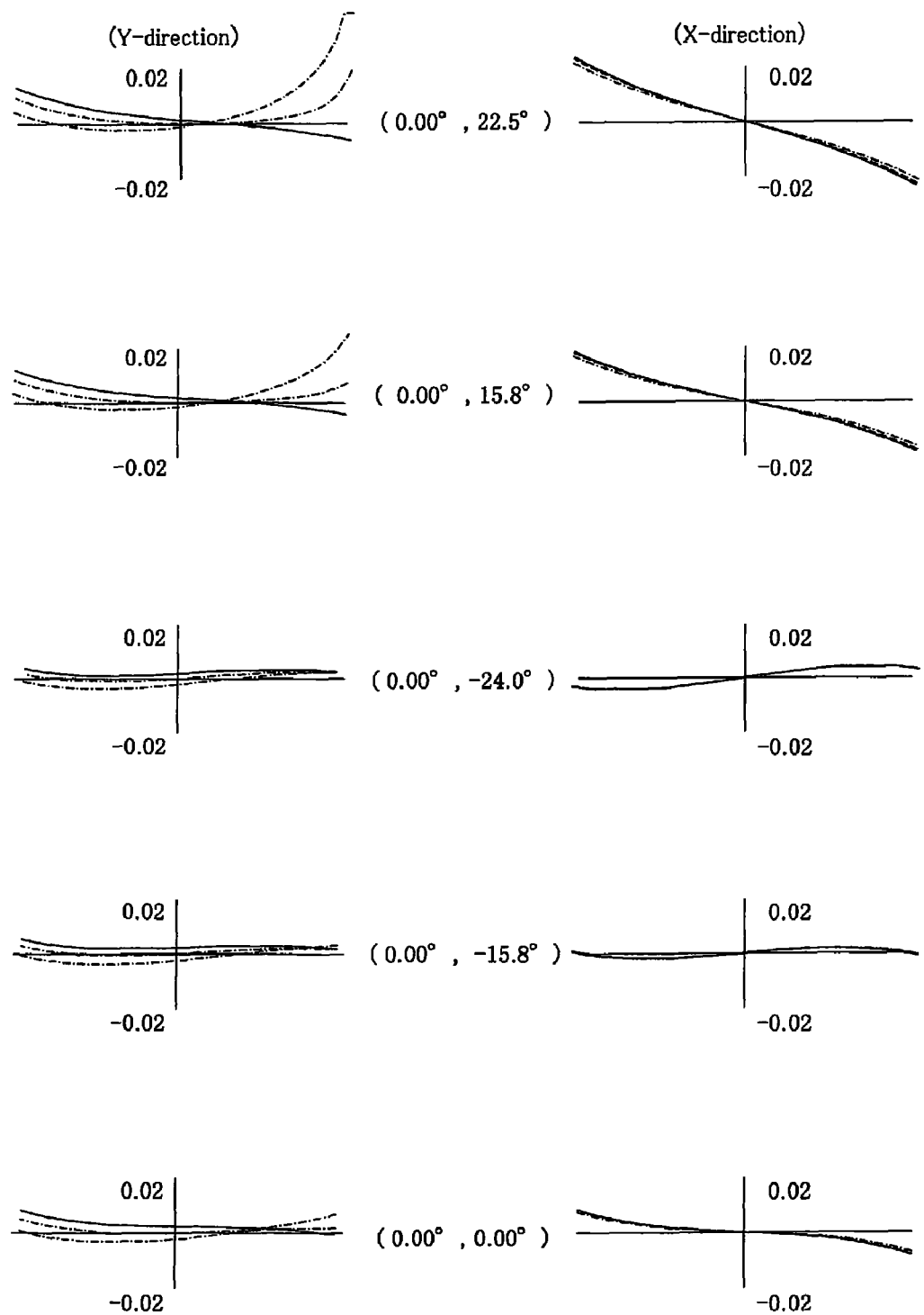
FIG. 23 is a schematic illustration of the transverse aberrations of the overall optical system of Example 7 on the side view optical path thereof.
Figure 24:
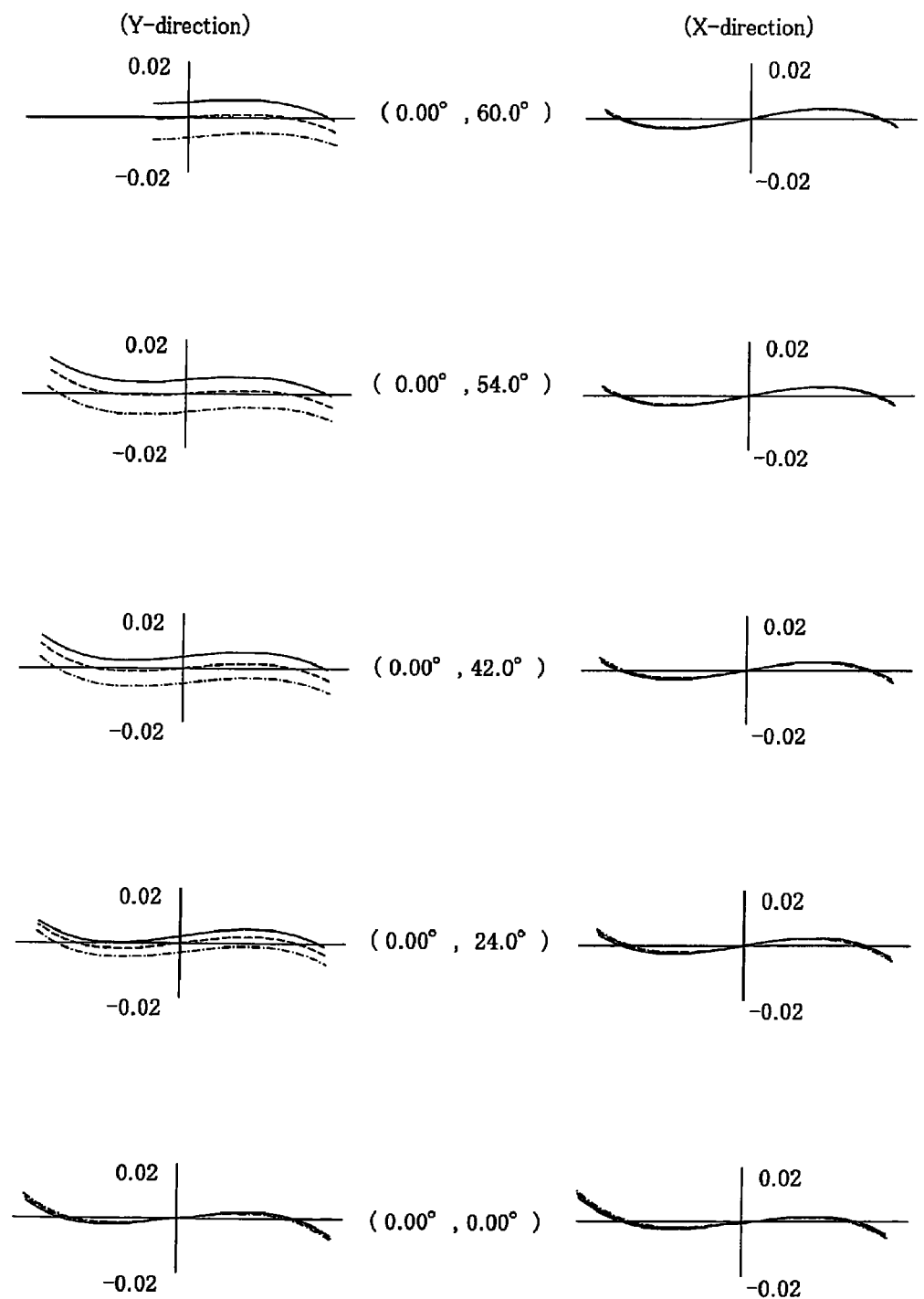
FIG. 24 is a schematic illustration of the transverse aberrations of the overall optical system of Example 7 on the direct view optical path thereof.

FIG. 22 is a schematic cross sectional view of the optical system 1 of Example 7 taken along the central axis 2 thereof. FIG. 23 is a schematic illustration of the transverse aberrations of the overall optical system of this example on the side view optical path thereof. FIG. 24 is a schematic illustration of the transverse aberrations of the overall optical system of this example on the direct view optical path thereof. In each of the views representing the transverse aberrations, each pair of angle values represented at the center indicates (the view angle in the horizontal direction, the view angle in the vertical direction). The transverse aberrations in the Y direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, each of the transmissive surfaces and the reflective surfaces that are rotationally symmetric relative to the central axis 2 of the optical system 1 and represent a refractive index greater than 1 is designed as extended rotary free curved surface but the side view first reflective surface 22 of the side view optical path A does not involve any term of higher degree. Additionally, the extended rotary free curved surface of the side view second reflective surface 23 of the side view optical path A is orthogonal to the plane of rotationally symmetry and does not involve any term of higher degree so that it is equivalent to a spherical surface.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group Gf includes a first group G1 and a second group G2, while the back group Gb includes a third group G3 and a fourth group G4.

The first group G1 is formed by a transparent medium L1 that is rotationally symmetric relative to the central axis 2 and has a refractive index greater than 1. The transparent medium L1 has a direct view first transmissive surface 11 whose radius of curvature is infinity and a direct view second transmissive surface 12 that is arranged at the side of, the image plane 5 relative to the direct view first transmissive surface 11 and formed by a spherical surface and has negative power.

The second group G2 is formed by a transparent medium L2 that is rotationally symmetric around the central axis 2 and has a refractive index greater than 1. It is an optical path synthesizing optical system for synthetically combining the side view optical path A and the direct view optical path B. The transparent medium L2 has a cylindrical side view first transmissive surface 21 that is arranged at the external side vis-a-vis the object surface 3 and parallel to the Z-axis so as to operate as a first transmissive surface, a side view first reflective surface 22 that is formed by an extended rotary free curved surface in the inside of the transparent medium L2 at the side of the central axis 2 relative to the side view first transmissive surface 21 and has negative power so as to operate as a first reflective surface, a side view second reflective surface 23 that is formed by a spherical surface in the inside of the transparent medium L2 at the side opposite to the image plane 5 as viewed from the side view first reflective surface 22 and has positive power so as to operate as a second reflective surface and a side view second transmissive surface 24 that is formed by a spherical surface and arranged at the side of the image plane 5 relative to the side view second reflective surface 23 and has negative power so as to operate as a second transmissive surface as well as a direct view third transmissive surface 25 that is formed by a spherical surface and has negative power and a direct view fourth transmissive surface 26 that is formed by a spherical surface and arranged at the side of the image plane 5 relative to the direct view third transmissive surface 25 and has negative power. The side view second transmissive surface 24 and the direct view fourth transmissive surface 26 are the same surface.

The third group G3 is formed by a positive meniscus lens L3 with its convex surface directed to the image plane 5 and has a common first transmissive surface 31 and a common second transmissive surface 32 arranged at the side of the image plane 5 relative to the common first transmissive surface 31.

The fourth group G4 is formed by a cemented lens of a negative meniscus lens L4 with its concave surface directed to the image plane and a positive meniscus lens L5 with its concave surface directed to the image plane and has a common third transmissive surface 41, a cementing surface 45 arranged at the side of the image plane 5 relative to the common third transmissive surface 41 and a common fourth transmissive surface 51 arranged at the side of the image plane 5 relative to the cementing surface 45.

The optical system 1 forms a side view optical path A and a direct view optical path B. As for the side view optical path A, the flux of light entering it from the side view object surface 3 at the side of the optical system 1 proceeds sequentially by way of the second group G2 of the front group Gf and the back group Gb and forms an annular image off the central axis 2 of the image plane 5 extending perpendicularly relative to the central axis 2. As for the direct view optical path B, the flux of light entering it from the direct view object surface near the central axis 2 of the optical system 1 proceeds sequentially by way of the front group Gf and the back group Gb and forms a circular image near the central axis 2 of the image plane 5 extending perpendicularly relative to the central axis 2.

The flux of light entering the optical system 1 from a lateral side of the optical system 1 to proceed along the side view optical path A goes into the transparent medium L2 of the second group G2 of the front group Gf by way of the side view first transmissive surface 21 and is reflected by the side view first reflective surface 22 at the side of the central axis 2 to the side opposite to the image plane 5 and then by the side view second reflective surface 23 to the side of the image plane 5 to form a substantially Z-shaped optical path before going out from the transparent medium L2 to the outside by way of the side view second transmissive surface 24.

Subsequently, the flux of light goes into the positive meniscus lens L3 of the third group G3 of the back group Gb at the opposite side relative to the central axis 2 by way of the aperture S arranged coaxially with the central axis 2 between the front group Gf and the back group Gb to operate as a stop and the common first transmissive surface 31 and then goes out from the common second transmissive surface 32. Thereafter, it goes into the negative meniscus lens L4 of the fourth group G4 by way of the common third transmissive surface 41 and goes out from the common fourth transmissive surface 51 of the positive meniscus lens L5 by way of the cementing surface 45 to form an image at a predetermined radial position off the central axis 2 of the image plane 5.

The flux of light entering the optical system 1 to proceed along the direct view optical path B goes into the transparent medium L1 of the first group G1 of the front group Gf byway of the direct view first transmissive surface 11 and goes out from the transparent medium L1 by way of the direct view second transmissive surface 12 arranged at the side of the image plane 5 relative to the direct view first transmissive surface 11. Thereafter, it goes into the transparent medium L2 of the second group G2 by way of the direct view third transmissive surface 25 and goes out from the transparent medium L2 by way of the direct view fourth transmissive surface 26 arranged at the side of the image plane 5 relative to the direct view first transmissive surface 11.

Subsequently, the flux of light goes into the positive meniscus lens L3 of the third group G3 of the back group Gb byway of the aperture S arranged coaxially with the central axis 2 between the front group Gf and the back group Gb to operate as a stop and the common first transmissive surface 31 and then goes out from the common second transmissive surface 32. Thereafter, it goes into the negative meniscus lens L4 of the fourth group G4 by way of the common third transmissive surface 41 and goes out from the common fourth transmissive surface 51 of the positive meniscus lens L5 by way of the cementing surface 45 to form an image on the central axis 2 of the image plane 5.

The specifications of Example 7 are as follows.

| | |
|---|---|
| view angle (side view) | 89.5° to 135° |
| view angle (direct view) | 0° to 60° |
| stop diameter | ø0.5 mm |
| image size (side view) | ø1.80 to ø2.57 |
| (direct view) | ø1.54 |

Figure 25:
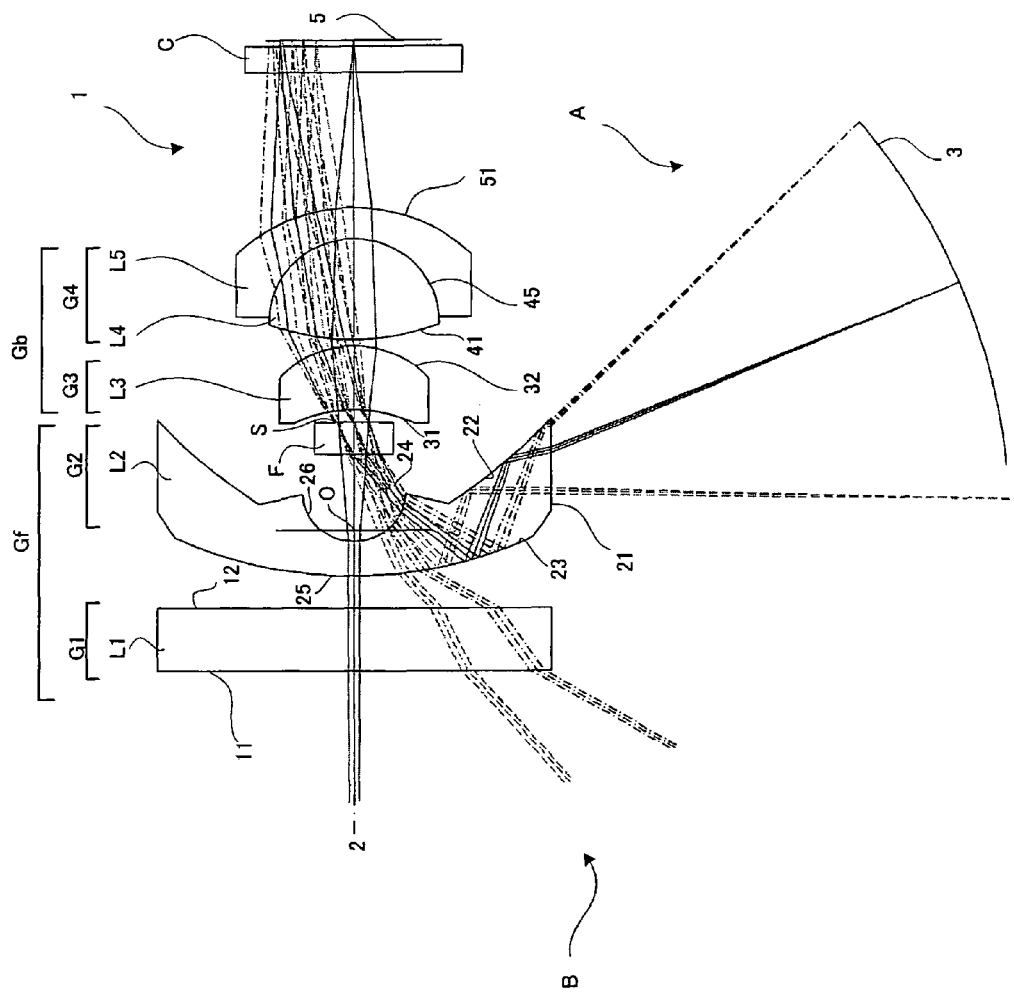
FIG. 25 is a schematic cross sectional view of the optical system of Example 8 of the present invention taken along the central axis thereof.
Figure 26:
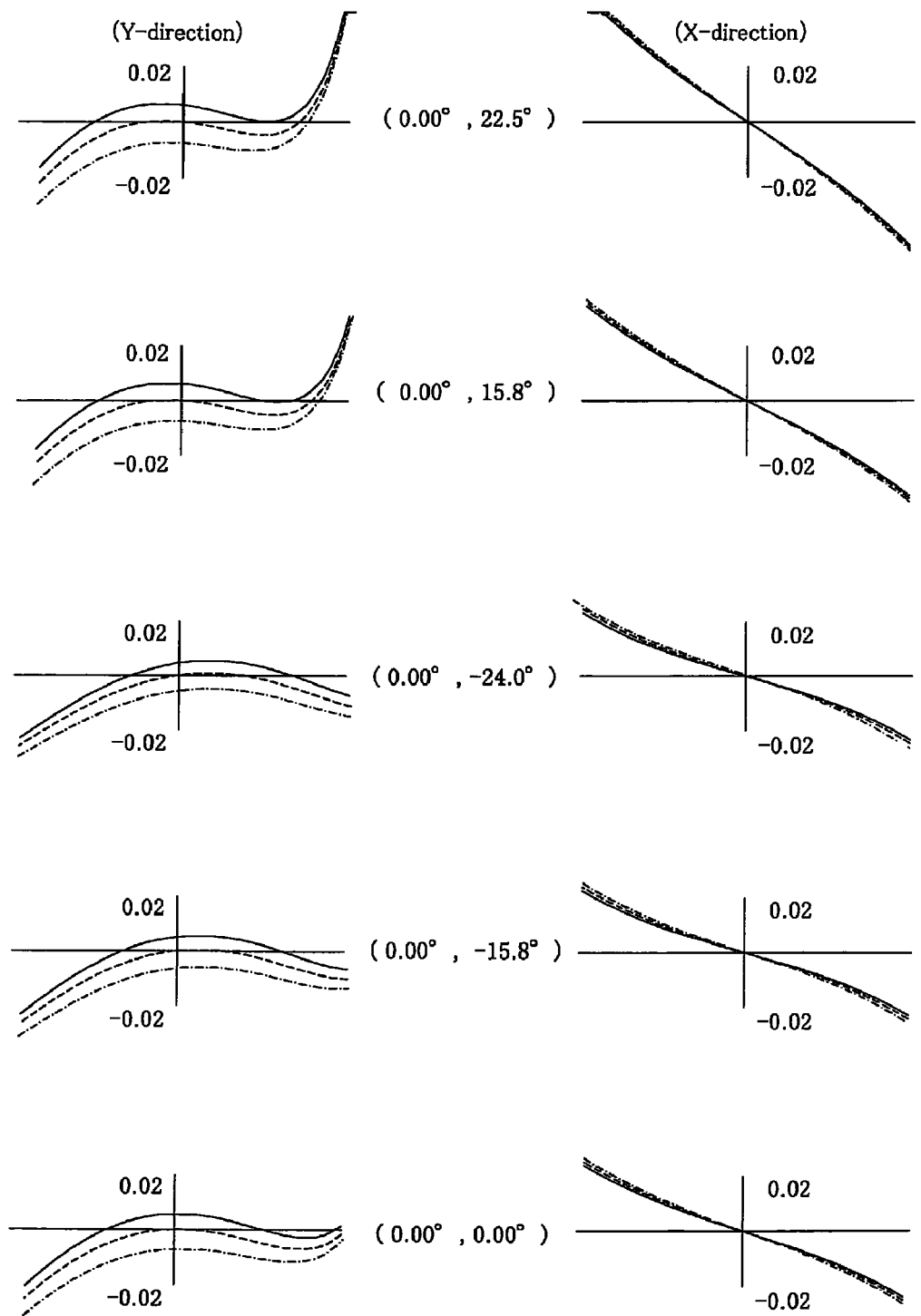
FIG. 26 is a schematic illustration of the transverse aberrations of the overall optical system of Example 8 on the side view optical path thereof.
Figure 27:
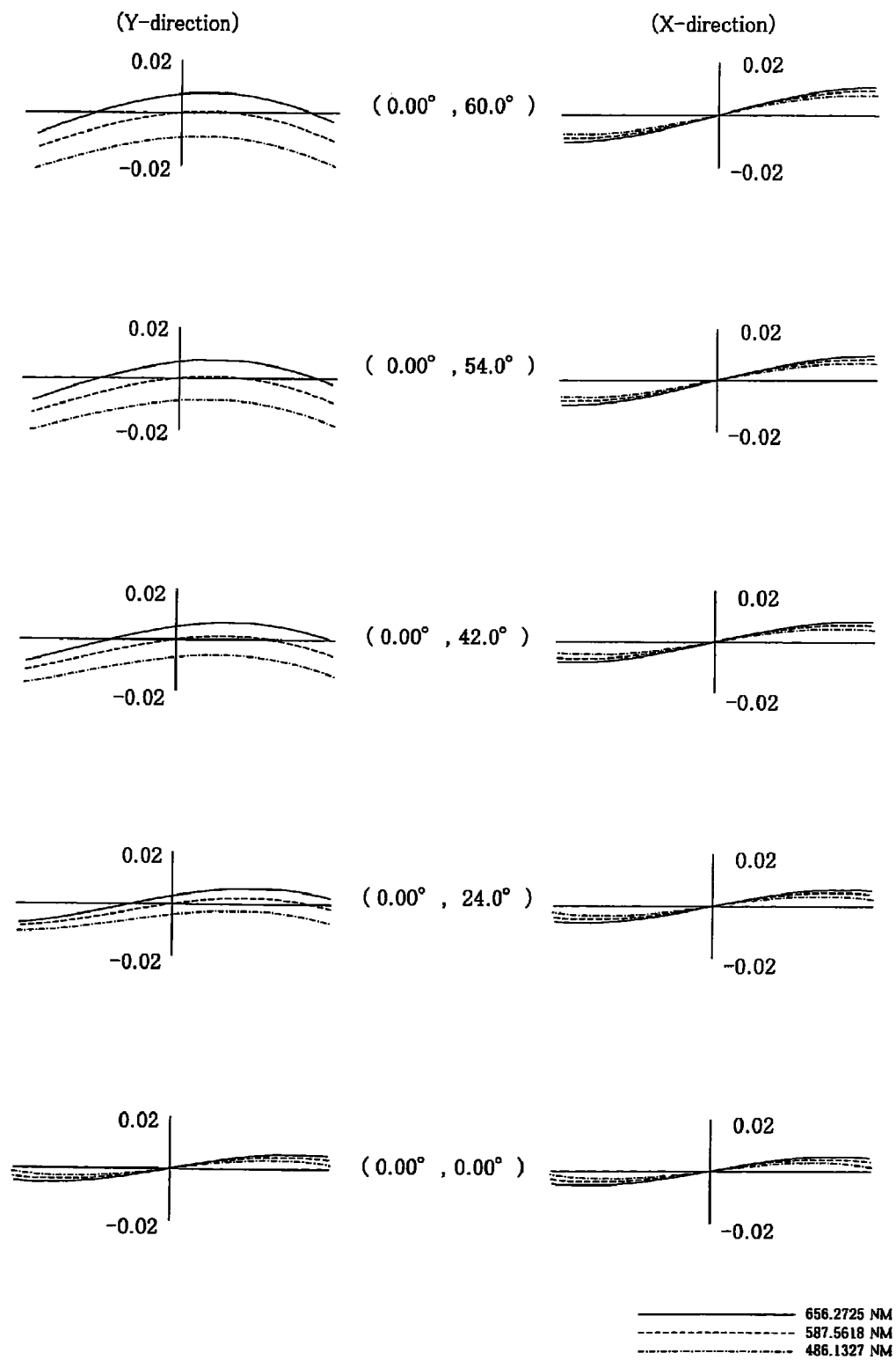
FIG. 27 is a schematic illustration of the transverse aberrations of the overall optical system of Example 8 on the direct view optical path thereof.

FIG. 25 is a schematic cross sectional view of the optical system 1 of Example 8 taken along the central axis 2 thereof. FIG. 26 is a schematic illustration of the transverse aberrations of the overall optical system of this example on the side view optical path thereof. FIG. 27 is a schematic illustration of the transverse aberrations of the overall optical system of this example on the direct view optical path thereof. In each of the views representing the transverse aberrations, each pair of angle values represented at the center indicates (the view angle in the horizontal direction, the view angle in the vertical direction). The transverse aberrations in the Y direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, the side view first reflective surface 22 of the side view optical path A out of the transmissive surfaces and the reflective surfaces that are rotationally symmetric relative to the central axis 2 of the optical system 1 and has a refractive index greater than 1 is designed as an extended rotary free curved surface. While each of the transmissive surfaces and the side view second reflective surface 23 of the side view optical path A is designed as an aspheric surface, it is equivalent to a spherical surface because it does not involve any term of aspheric surface.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group Gf includes a first group G1 and a second group G2, while the back group Gb includes a third group G3 and a fourth group G4.

The first group G1 is formed by a transparent medium L1 that is rotationally symmetric relative to the central axis 2 and has a refractive index greater than 1. The transparent medium L1 has a direct view first transmissive surface 11 whose radius of curvature is infinity and a direct view second transmissive surface 12 that is arranged at the side of the image plane 5 relative to the direct view first transmissive surface 11 whose radius of curvature is infinity.

The second group G2 is formed by a transparent medium L2 that is rotationally symmetric around the central axis 2 and has a refractive index greater than 1. It is an optical path synthesizing optical system for synthetically combining the side view optical path A and the direct view optical path B. The transparent medium L2 has a cylindrical side view first transmissive surface 21 that is arranged at the external side vis-a-vis the object surface 3 and parallel to the Z-axis so as to operate as a first transmissive surface, a side view first reflective surface 22 that is formed by an extended rotary free curved surface in the inside of the transparent medium L2 at the side of the central axis 2 relative to the side view first transmissive surface 21 and has negative power so as to operate as a first reflective surface, a side view second reflective surface 23 that is formed by a spherical surface in the inside of the transparent medium L2 at the side opposite to the image plane 5 as viewed from the side view first reflective surface 22 and has positive power so as to operate as a second reflective surface and a side view second transmissive surface 24 that is formed by a spherical surface and arranged at the side of the image plane 5 relative to the side view second reflective surface 23 and has negative power so as to operate as a second transmissive surface as well as a direct view third transmissive surface 25 that is formed by a spherical surface and has negative power and a direct view fourth transmissive surface 26 that is formed by a spherical surface and arranged at the side of the image plane 5 relative to the direct view third transmissive surface 25 and has negative power. The side view second transmissive surface 24 and the direct view fourth transmissive surface 26 are the same surface.

The third group G3 is formed by a positive meniscus lens L3 with its convex surface directed to the image plane 5 and has a common first transmissive surface 31 and a common second transmissive surface 32 arranged at the side of the image plane 5 relative to the common first transmissive surface 31.

The fourth group G4 is formed by a cemented lens of a negative meniscus lens L5 with its convex surface directed to the image plane 5 and a double convex positive lens L4 and has a common third transmissive surface 41, a cementing surface 45 arranged at the side of the image plane 5 relative to the common third transmissive surface 41 and a common fourth transmissive surface 51 arranged at the side of the image plane 5 relative to the cementing surface 45.

The optical system 1 forms a side view optical path A and a direct view optical path B. As for the side view optical path A, the flux of light entering it from the side view object surface 3 at the side of the optical system 1 proceeds sequentially by way of the second group G2 of the front group Gf and the back group Gb and forms an annular image off the central axis 2 of the image plane 5 extending perpendicularly relative to the central axis 2. As for the direct view optical path B, the flux of light entering it from the direct view object surface near the central axis 2 of the optical system 1 proceeds sequentially by way of the front group Gf and the back group Gb and forms a circular image near the central axis 2 of the image plane 5 extending perpendicularly relative to the central axis 2.

The flux of light entering the optical system 1 from a lateral side of the optical system 1 to proceed along the side view optical path A goes into the transparent medium L2 of the second group G2 of the front group Gf by way of the side view first transmissive surface 21 and is reflected by the side view first reflective surface 22 at the side of the central axis 2 to the side opposite to the image plane 5 and then by the side view second reflective surface 23 to the side of the image plane 5 to form a substantially Z-shaped optical path before going out from the transparent medium L2 to the outside by way of the side view second transmissive surface 24.

Subsequently, the flux of light goes into the positive meniscus lens L3 of the third group G3 of the back group Gb at the opposite side relative to the central axis 2 by way of the aperture S arranged coaxially with the central axis 2 between the front group Gf and the back group Gb to operate as a stop and the common first transmissive surface 31 and then goes out from the common second transmissive surface 32. Thereafter, it goes into the double convex positive lens L4 of the fourth group G4 by way of the common third transmissive surface 41 and goes out from the common fourth transmissive surface 51 of the negative meniscus lens L5 by way of the cementing surface 45 to form an image at a predetermined radial position off the central axis 2 of the image plane 5.

The flux of light entering the optical system 1 to proceed along the direct view optical path B goes into the transparent medium L1 of the first group G1 of the front group Gf by way of the direct view first transmissive surface 11 and goes out from the transparent medium L1 by way of the direct view second transmissive surface 12 arranged at the side of the image plane 5 relative to the direct view first transmissive surface 11. Thereafter, it goes into the transparent medium L2 of the second group G2 by way of the direct view third transmissive surface 25 and goes out from the transparent medium L2 by way of the direct view fourth transmissive surface 26 arranged at the side of the image plane 5 relative to the direct view first transmissive surface 11.

Subsequently, the flux of light goes into the positive meniscus lens L3 of the third group G3 of the back group Gb by way of the aperture S arranged coaxially with the central axis 2 between the front group Gf and the back group Gb to operate as a stop and the common first transmissive surface 31 and then goes out from the common second transmissive surface 32. Thereafter, it goes into the double convex positive lens L4 of the fourth group G4 by way of the common third transmissive surface 41 and goes out from the common fourth transmissive surface 51 of the negative meniscus lens L5 to the outside by way of the cementing surface 45 to form an image on the central axis 2 of the image plane 5.

The specifications of Example 8 are as follows.

| view angle (side view) | 89.5° to 135° |
| --- | --- |
| view angle (direct view) | 0° to 60° |
| stop diameter | ø0.5 mm |
| image size (side view) | ø1.87 to ø2.48 |
| (direct view) | ø1.57 |

Figure 28:
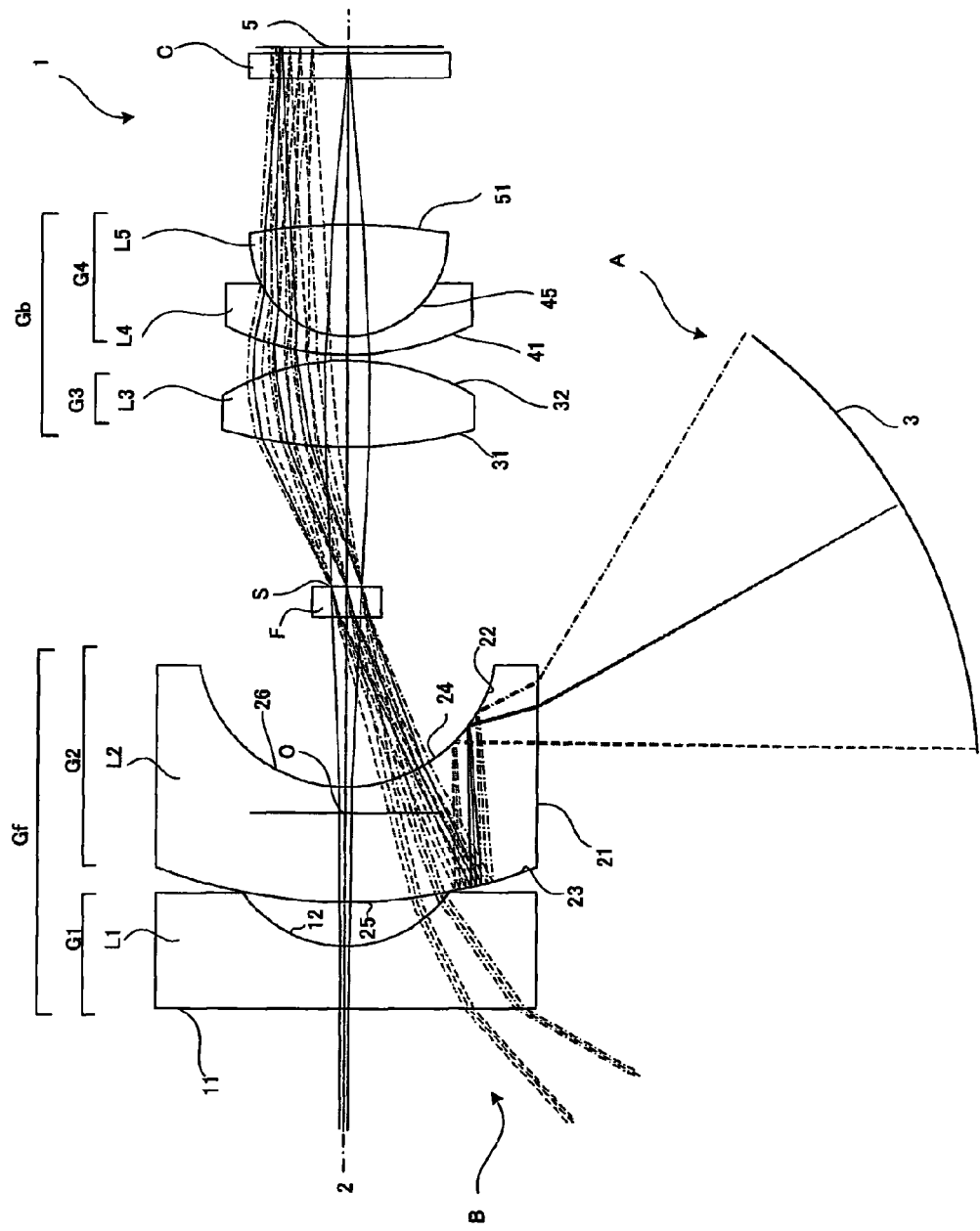
FIG. 28 is a schematic cross sectional view of the optical system of Example 9 of the present invention taken along the central axis thereof.
Figure 29:
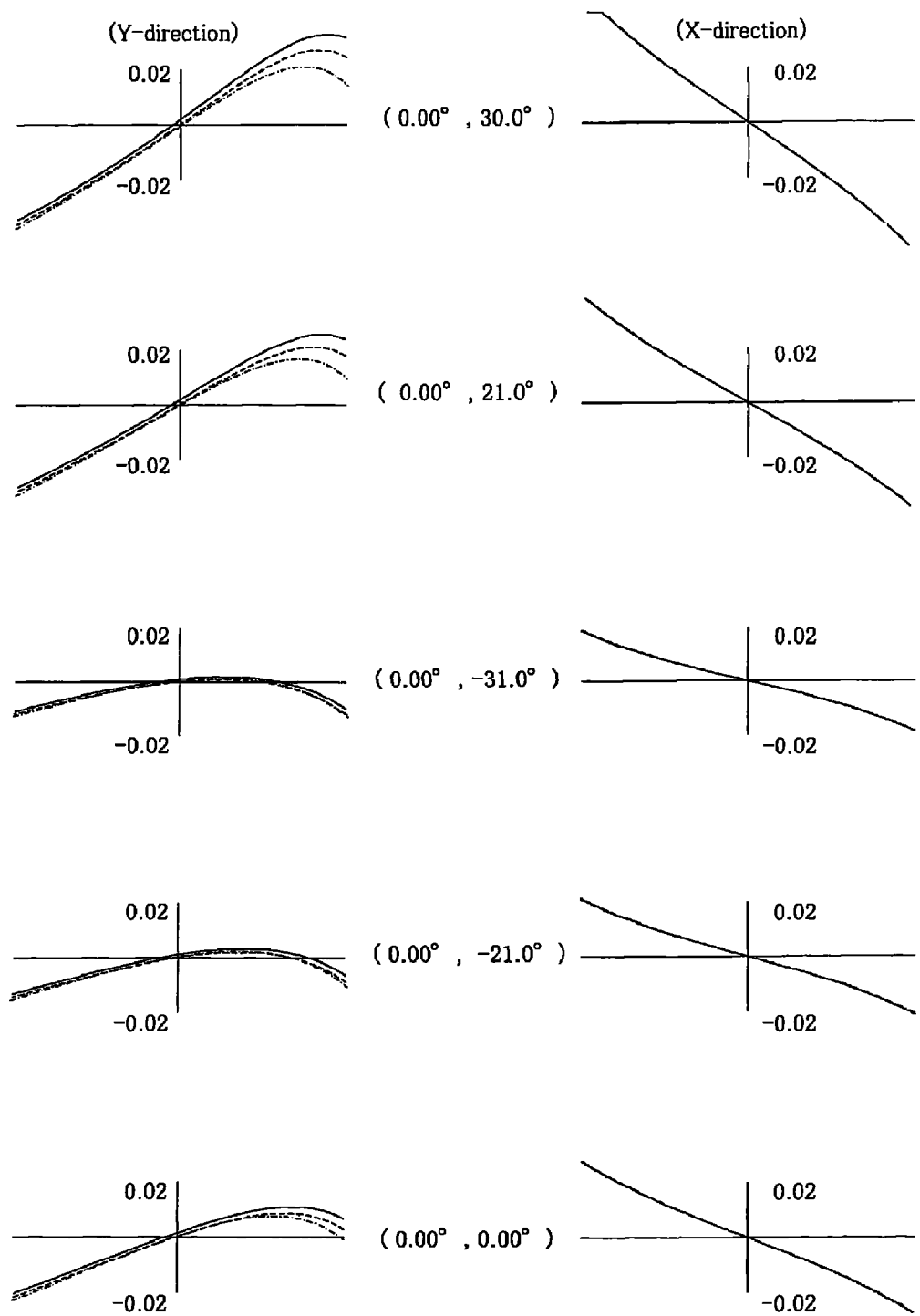
FIG. 29 is a schematic illustration of the transverse aberrations of the overall optical system of Example 9 on the side view optical path thereof.
Figure 30:
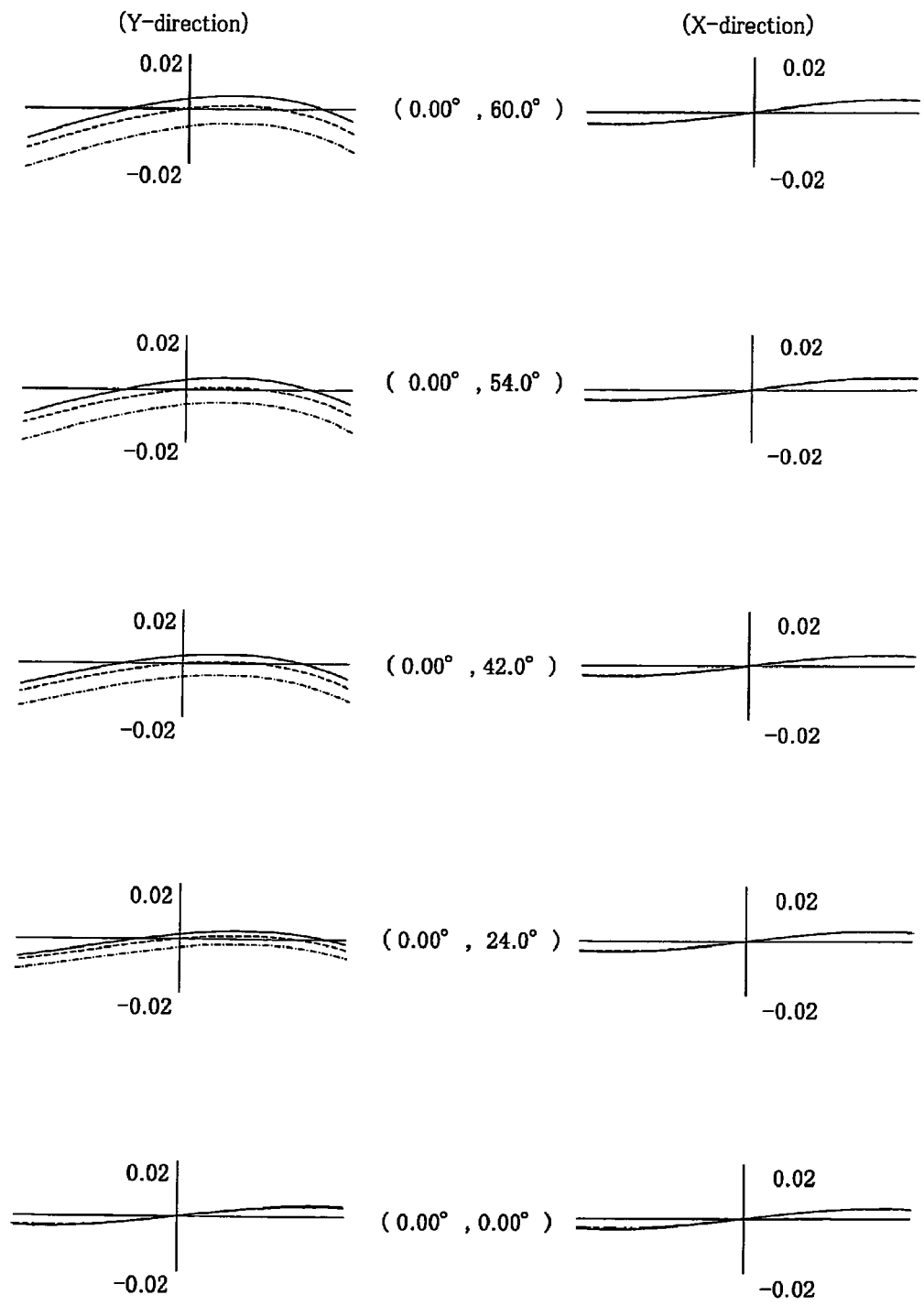
FIG. 30 is a schematic illustration of the transverse aberrations of the overall optical system of Example 9 on the direct view optical path thereof.

FIG. 28 is a schematic cross sectional view of the optical system 1 of Example 9 taken along the central axis 2 thereof. FIG. 29 is a schematic illustration of the transverse aberrations of the overall optical system of this example on the side view optical path thereof. FIG. 30 is a schematic illustration of the transverse aberrations of the overall optical system of this example on the direct view optical path thereof. In each of the views representing the transverse aberrations, each pair of angle values represented at the center indicates (the view angle in the horizontal direction, the view angle in the vertical direction). The transverse aberrations in the Y direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, each of the transmissive surfaces and the reflective surfaces of the transparent medium that is rotationally symmetric relative to the central axis 2 of the optical system 1 and has a refractive index greater than 1 is designed as a spherical surface.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group Gf includes a first group G1 and a second group G2, while the back group Gb includes a third group G3 and a fourth group G4.

The first group G1 is formed by a transparent medium L1 that is rotationally symmetric relative to the central axis 2 and has a refractive index greater than 1. The transparent medium L1 has a direct view first transmissive surface 11 whose radius of curvature is infinity and a direct view second transmissive surface 12 that is arranged at the side of the image plane 5 relative to the direct view first transmissive surface 11 and formed by a spherical surface and has negative power.

The second group G2 is formed by a transparent medium L2 that is rotationally symmetric around the central axis 2 and has a refractive index greater than 1. It is an optical path synthesizing optical system for synthetically combining the side view optical path A and the direct view optical path B. The transparent medium L2 has a cylindrical side view first transmissive surface 21 that is arranged at the external side vis-a-vis the object surface 3 and parallel to the Z-axis so as to operate as a first transmissive surface, a side view first reflective surface 22 that is formed by a spherical surface in the inside of the transparent medium L2 at the side of the central axis 2 relative to the side view first transmissive surface 21 and has negative power so as to operate as a first reflective surface, a side view second reflective surface 23 that is formed by a spherical surface in the inside of the transparent medium L2 at the side opposite to the image plane 5 as viewed from the side view first reflective surface 22 and has positive power so as to operate as a second reflective surface and a side view second transmissive surface 24 that is formed by a spherical surface and arranged at the side of the image plane 5 relative to the side view second reflective surface 23 and has negative power so as to operate as a second transmissive surface as well as a direct view third transmissive surface 25 that is formed by a spherical surface and has negative power so as to operate as a third transmissive surface and a direct view fourth transmissive surface 26 that is formed by a spherical surface and arranged at the side of the image plane 5 relative to the direct view third transmissive surface 25 and has negative power so as to operate as a fourth transmissive surface. The side view first reflective surface 22, the side view second transmissive surface 24 and the direct view fourth transmissive surface 26 are the same surface, while the side view second reflective surface 23 and the direct view third transmissive surface 25 are the same surface.

The third group G3 is formed by a double convex positive lens L3 and has a common first transmissive surface 31 and a common second transmissive surface 32 arranged at the side of the image plane 5 relative to the common first transmissive surface 31.

The fourth group G4 is formed by a cemented lens of a negative meniscus lens L4 with its concave surface directed to the image plane and a double convex positive lens L5 and has a common third transmissive surface 41, a cementing surface 42 arranged at the side of the image plane 5 relative to the common third transmissive surface 41 and a common fourth transmissive surface 51 arranged at the side of the image plane 5 relative to the cementing surface 45.

The optical system 1 forms a side view optical path A and a direct view optical path B. As for the side view optical path A, the flux of light entering it from the side view object surface 3 at the side of the optical system 1 proceeds sequentially by way of the second group G2 of the front group Gf and the back group Gb and forms an annular image off the central axis 2 of the image plane 5 extending perpendicularly relative to the central axis 2. As for the direct view optical path B, the flux of light entering it from the direct view object surface near the central axis 2 of the optical system 1 proceeds sequentially by way of the front group Gf and the back group Gb and forms a circular image near the central axis 2 of the image plane 5 extending perpendicularly relative to the central axis 2.

The flux of light entering the optical system 1 from a lateral side of the optical system 1 to proceed along the side view optical path A goes into the transparent medium L2 of the second group G2 of the front group Gf by way of the side view first transmissive surface 21 and is reflected by the side view first reflective surface 22 at the side of the central axis 2 to the side opposite to the image plane 5 and then by the side view second reflective surface 23 to the side of the image plane 5 to form a substantially Z-shaped optical path before going out from the transparent medium L2 to the outside by way of the second transmissive surface 24.

Subsequently, the flux of light goes into the double convex positive lens L3 of the third group G3 of the back group Gb at the opposite side relative to the central axis 2 by way of the aperture S arranged coaxially with the central axis 2 between the front group Gf and the back group Gb to operate as a stop and the common first transmissive surface 31 and then goes out from the common second transmissive surface 32. Thereafter, it goes into the negative meniscus lens L4 of the fourth group G4 by way of the common third transmissive surface 41 and goes out from the common fourth transmissive surface 51 of the double convex positive lens L5 by way of the cementing surface 45 to form an image at a predetermined radial position off the central axis 2 of the image plane 5.

The flux of light entering the optical system 1 to proceed along the direct view optical path B goes into the transparent medium L1 of the first group G1 of the front group Gf by way of the direct view first transmissive surface 11 and goes out from the transparent medium L1 by way of the direct view second transmissive surface 12 arranged at the side of the image plane 5 relative to the direct view first transmissive surface 11. Thereafter, it goes into the transparent medium L2 of the second group G2 by way of the direct view third transmissive surface 25 and goes out from the transparent medium L2 by way of the direct view fourth transmissive surface 26 arranged at the side of the image plane 5 relative to the direct view first transmissive surface 11.

Subsequently, the flux of light goes into the double convex positive lens L3 of the third group G3 of the back group Gb by way of the aperture S arranged coaxially with the central axis 2 between the front group Gf and the back group Gb to operate as a stop and the common first transmissive surface 31 and then goes out from the common second transmissive surface 32. Thereafter, it goes into the negative meniscus lens L4 of the fourth group G4 by way of the common third transmissive surface 41 and goes out from the common fourth transmissive surface 51 of the double convex positive lens L5 by way of the cementing surface 45 to form an image on the central axis 2 of the image plane 5.

The specifications of Example 9 are as follows.

| | |
|---|---|
| view angle (side view) | 89° to 150° |
| view angle (direct view) | 0° to 60° |
| stop diameter | ø0.5 mm |
| image size (side view) | ø1.90 to ø2.41 |
| (direct view) | ø1.57 |

Figure 31:
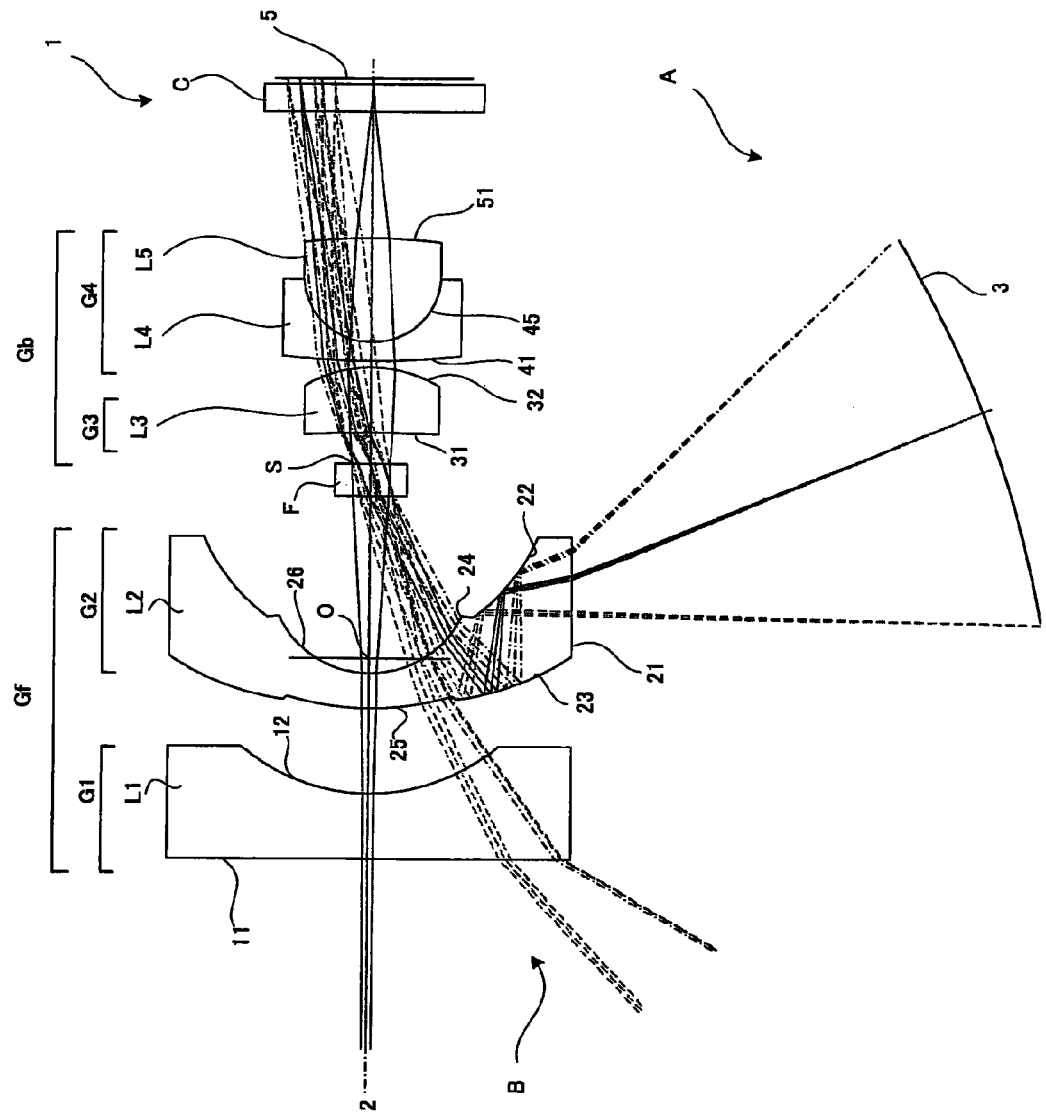
FIG. 31 is a schematic cross sectional view of the optical system of Example 10 of the present invention taken along the central axis thereof.
Figure 32:
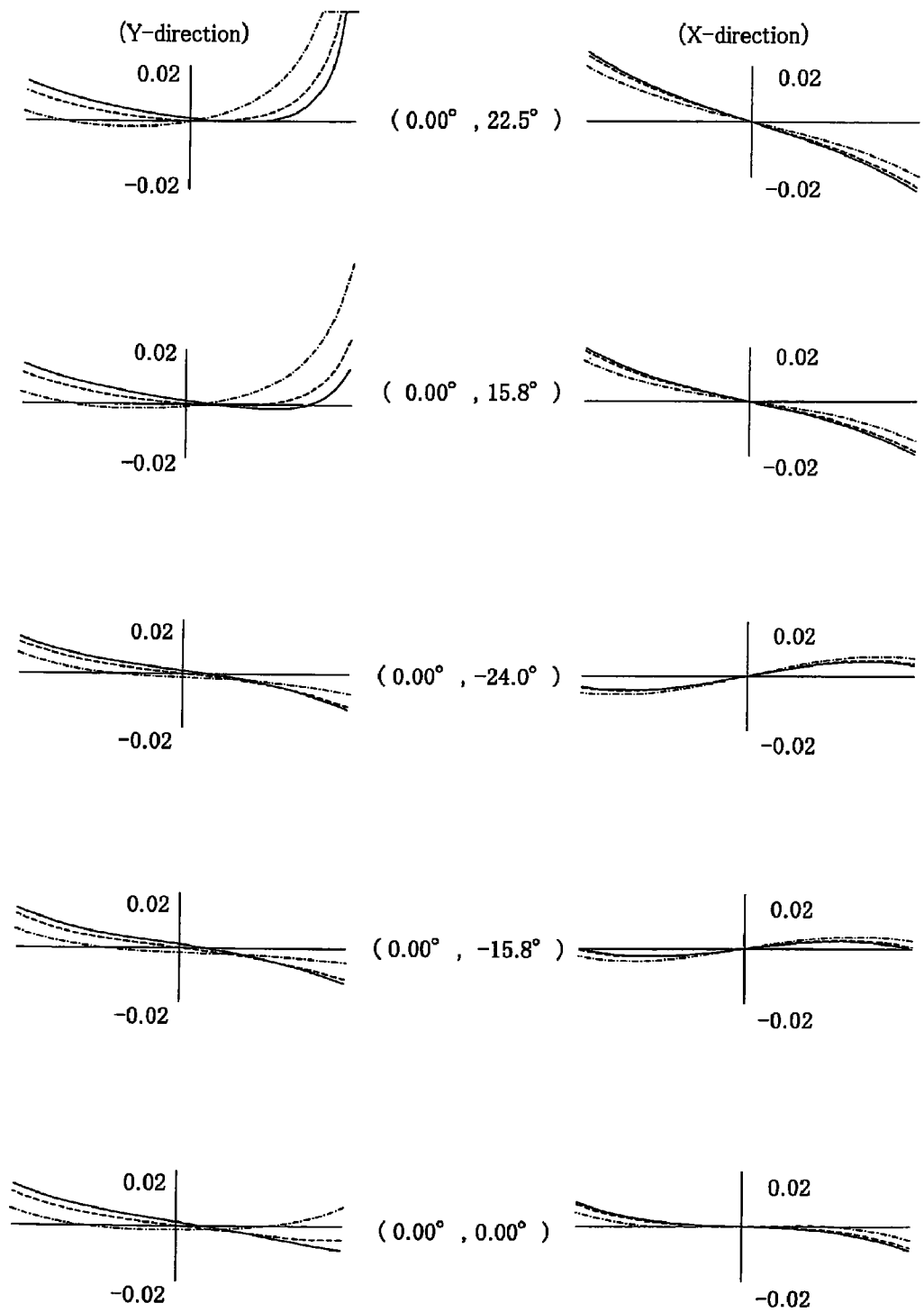
FIG. 32 is a schematic illustration of the transverse aberrations of the overall optical system of Example 10 on the side view optical path thereof.
Figure 33:
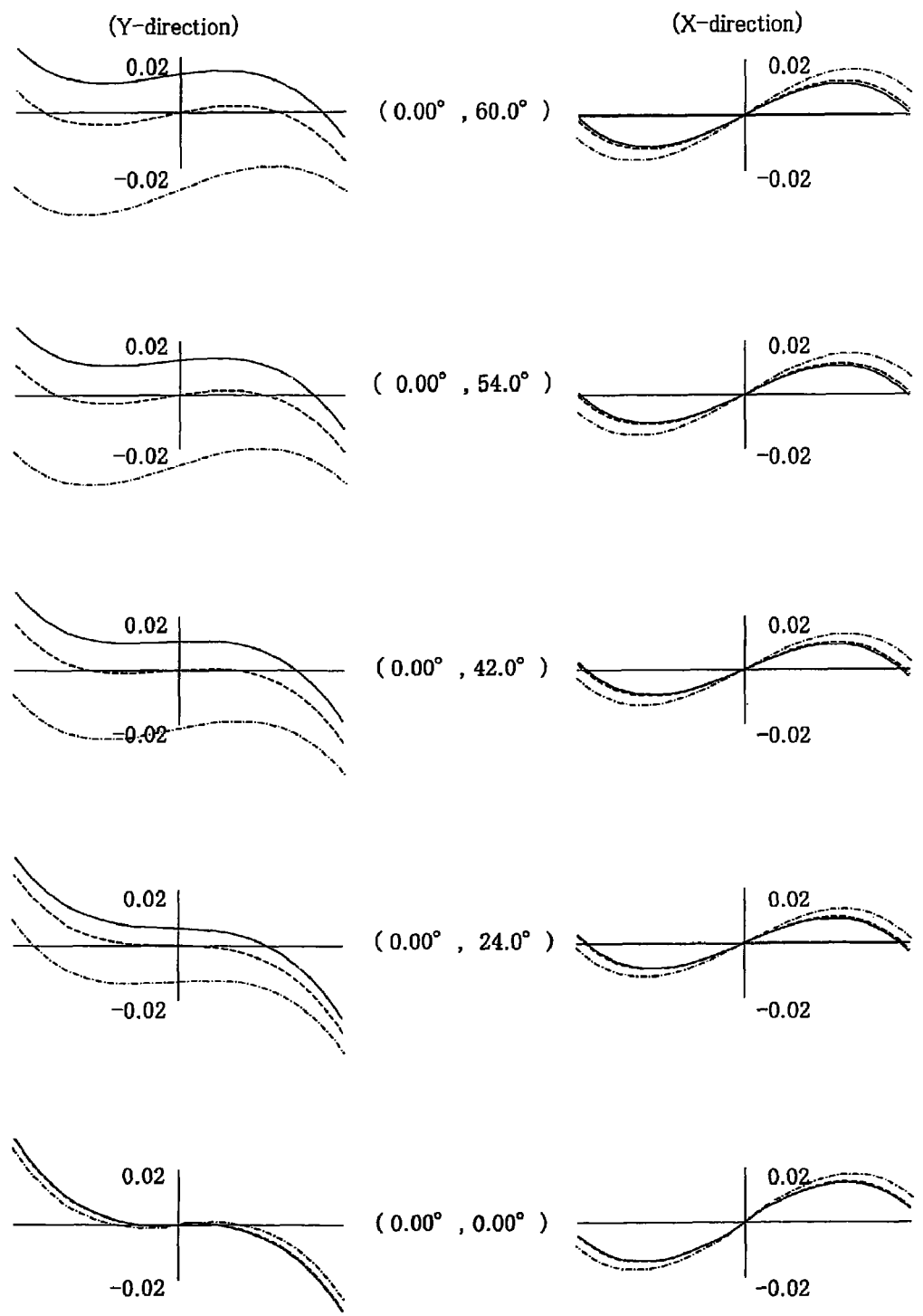
FIG. 33 is a schematic illustration of the transverse aberrations of the overall optical system of Example 10 on the direct view optical path thereof.

FIG. 31 is a schematic cross sectional view of the optical system 1 of Example 10 taken along the central axis 2 thereof. FIG. 32 is a schematic illustration of the transverse aberrations of the overall optical system of this example on the side view optical path thereof. FIG. 33 is a schematic illustration of the transverse aberrations of the overall optical system of this example on the direct view optical path thereof. In each of the views representing the transverse aberrations, each pair of angle values represented at the center indicates (the view angle in the horizontal direction, the view angle in the vertical direction). The transverse aberrations in the Y direction (the meridional direction) and those in the X-direction (the sagittal direction) are also denoted. Note that a negative view angle in the horizontal direction denotes a clockwise angle observed by facing in the positive direction of the Y-axis, whereas a negative view angle in the vertical direction also denotes a clockwise angle observed by facing in the positive direction of the X-axis. This note is also applicable in the following similar descriptions.

In this example, each of the reflective surfaces of the transparent medium that is rotationally symmetric relative to the central axis 2 of the optical system 1 and has a refractive index greater than 1 is designed as an extended rotary free curved surface.

The optical system 1 includes a front group Gf that is rotationally symmetric relative to the central axis 2, a back group Gb that is also rotationally symmetric relative to the central axis 2 and an aperture S arranged between the front group Gf and the back group Gb so as to be coaxial with the central axis 2. The front group Gf includes a first group G1 and a second group G2, while the back group Gb includes a third group G3 and a fourth group G4.

The first group G1 is formed by a transparent medium L1 that is rotationally symmetric relative to the central axis 2 and has a refractive index greater than 1. The transparent medium L1 has a direct view first transmissive surface 11 whose radius of curvature is infinity and a direct view second transmissive surface 12 that is arranged at the side of the image plane 5 relative to the direct view first transmissive surface 11 and formed by a spherical surface and has negative power.

The second group G2 is formed by a transparent medium L2 that is rotationally symmetric around the central axis 2 and has a refractive index greater than 1. It is an optical path synthesizing optical system for synthetically combining the side view optical path A and the direct view optical path B. The transparent medium L2 has a cylindrical side view first transmissive surface 21 that is arranged at the external side vis-a-vis the object surface 3 and parallel to the Z-axis so as to operate as a first transmissive surface, a side view first reflective surface 22 that is formed by an extended rotary free curved surface in the inside of the transparent medium L2 at the side of the central axis 2 relative to the side view first transmissive surface 21 and has negative power so as to operate as a first reflective surface, a side view second reflective surface 23 that is formed by an extended rotary free curved surface in the inside of the transparent medium L2 at the side opposite to the image plane 5 as viewed from the side view first reflective surface 22 and has positive power so as to operate as a second reflective surface and a side view second transmissive surface 24 that is formed by an extended rotary free curved surface and arranged at the side of the image plane 5 relative to the side view second reflective surface 23 and has negative power so as to operate as a second transmissive surface as well as a direct view third transmissive surface 25 that is formed by an extended rotary free curved surface and has negative power and a direct view fourth transmissive surface 26 that is formed by a spherical surface and arranged at the side of the image plane 5 relative to the direct view third transmissive surface 25 and has negative power. The side view second transmissive surface 24 and the direct view fourth transmissive surface 26 are the same surface.

The third group G3 is formed by a positive meniscus lens L3 with its convex surface directed to the image plane 5 and has a common first transmissive surface 31 and a common second transmissive surface 32 arranged at the side of the image plane 5 relative to the common first transmissive surface 31.

The fourth group G4 is formed by a cemented lens of a negative meniscus lens L4 with its concave surface directed to the image plane and a double convex positive lens L5 and has a common third transmissive surface 41, a cementing surface 45 arranged at the side of the image plane 5 relative to the common third transmissive surface 41 and a common fourth transmissive surface 51 arranged at the side of the image plane 5 relative to the cementing surface 45.

The optical system 1 forms a side view optical path A and a direct view optical path B. As for the side view optical path A, the flux of light entering it from the side view object surface 3 at the side of the optical system 1 proceeds sequentially by way of the second group G2 of the front group Gf and the back group Gb and forms an annular image off the central axis 2 of the image plane 5 extending perpendicularly relative to the central axis 2. As for the direct view optical path B, the flux of light entering it from the direct view object surface near the central axis 2 of the optical system 1 proceeds sequentially by way of the front group Gf and the back group Gb and forms a circular image near the central axis 2 of the image plane 5 extending perpendicularly relative to the central axis 2.

The flux of light entering the optical system 1 from a lateral side of the optical system 1 to proceed along the side view optical path A goes into the transparent medium L2 of the second group G2 of the front group Gf by way of the side view first transmissive surface 21 and is reflected by the side view first reflective surface 22 at the side of the central axis 2 to the side opposite to the image plane 5 and then by the side view second reflective surface 23 to the side of the image plane 5 to form a substantially Z-shaped optical path before going out from the transparent medium L2 to the outside by way of the side view second transmissive surface 24.

Subsequently, the flux of light goes into the positive meniscus lens L3 of the third group G3 of the back group Gb at the opposite side relative to the central axis 2 by way of the aperture S arranged coaxially with the central axis 2 between the front group Gf and the back group Gb to operate as a stop and the common first transmissive surface 31 and then goes out from the common second transmissive surface 32. Thereafter, it goes into the negative meniscus lens L4 of the fourth group G4 by way of the common third transmissive surface 41 and goes out from the common fourth transmissive surface 51 of the double convex positive lens L5 by way of the cementing surface 45 to form an image at a predetermined radial position off the central axis 2 of the image plane 5.

The flux of light entering the optical system 1 to proceed along the direct view optical path B goes into the transparent medium L1 of the first group G1 of the front group Gf by way of the direct view first transmissive surface 11 and goes out from the transparent medium L1 by way of the direct view second transmissive surface 12 arranged at the side of the image plane 5 relative to the direct view first transmissive surface 11. Thereafter, it goes into the transparent medium L2 of the second group G2 by way of the direct view third transmissive surface 25 and goes out from the transparent medium L2 by way of the direct view fourth transmissive surface 26 arranged at the side of the image plane 5 relative to the direct view first transmissive surface 11.

Subsequently, the flux of light goes into the positive meniscus lens L3 of the third group G3 of the back group Gb by way of the aperture S arranged coaxially with the central axis 2 between the front group Gf and the back group Gb to operate as a stop and the common first transmissive surface 31 and then goes out from the common second transmissive surface 32. Thereafter, it goes into the negative meniscus lens L4 of the fourth group G4 by way of the common third transmissive surface 41 and goes out from the common fourth transmissive surface 51 of the double convex positive lens L5 byway of the cementing surface 45 to form an image on the central axis 2 of the image plane 5.

The specifications of Example 10 are as follows.

| | |
|---|---|
| view angle (side view) | 89.5° to 135° |
| view angle (direct view) | 0° to 60° |
| stop diameter | ø0.5 mm |
| image size (side view) | ø1.80 to ø2.57 |
| (direct view) | ø1.54 |

Some of the parameters of the above-described Examples 6 through 10 are listed below. In the table depicted below, "ASS" denotes an aspheric surface and "ERFS" denotes an extended rotary free curved surface, while "Re" denotes a reflective surface.

Example 6

| Side view optical path | | | | | |
|---|---|---|---|---|---|
| Surface number | Radius of curvature | Plane gap | Eccentricity | Refractive index | Abbe number |
| Object surface | 10.00 | 10.00 | eccentricity(1) | | |
| 1 | ERFS[1] | | eccentricity(2) | 1.8348 | 42.7 |
| 2 | ERFS[2] (RE) | | eccentricity(3) | 1.8348 | 42.7 |
| 3 | ERFS[3] (RE) | | eccentricity(4) | 1.8348 | 42.7 |
| 4 | ERFS[2] | | eccentricity(3) | | |
| 5 | ∞ | −0.50 | eccentricity(5) | 1.5163 | 64.1 |
| 6 | ∞ (Stop) | 0.35 | | | |
| 7 | −1.96 | 1.00 | | 1.7292 | 54.7 |
| 8 | −1.54 | 0.10 | | | |
| 9 | 2.41 | 0.30 | | 1.7529 | 27.7 |
| 10 | 1.25 | 1.60 | | 1.6583 | 53.9 |
| 11 | 31.16 | 1.87 | | | |
| 12 | ∞ | 0.40 | | 1.5163 | 64.1 |
| 13 | ∞ | 0.10 | | | |
| Image surface | ∞ | | | | |

| ERFS[1] | |
|---|---|
| RY | ∞ |
| θ | 90.00 |
| R | −3.00 |

| ERFS[2] | |
|---|---|
| RY | 2.04 |
| θ | 54.52 |
| R | −1.66 |

| ERFS[3] | |
|---|---|
| RY | 5.71 |
| θ | 18.97 |
| R | −1.86 |

| eccentricity(1) | | | | | |
|---|---|---|---|---|---|
| X | 0.00 | Y | −9.24 | Z | 3.83 |
| α | 112.50 | β | 0.00 | γ | 0.00 |

| eccentricity(2) | | | | | |
|---|---|---|---|---|---|
| X | 0.00 | Y | 0.00 | Z | 1.24 |
| α | 0.00 | β | 0.00 | γ | 0.00 |

| eccentricity(3) | | | | | |
|---|---|---|---|---|---|
| X | 0.00 | Y | 0.00 | Z | 0.96 |
| α | 0.00 | β | 0.00 | γ | 0.00 |

| eccentricity(4) | | | | | |
|---|---|---|---|---|---|
| X | 0.00 | Y | 0.00 | Z | −0.61 |
| α | 0.00 | β | 0.00 | γ | 0.00 |

| eccentricity(5) | | | | | |
|---|---|---|---|---|---|
| X | 0.00 | Y | 0.00 | Z | 2.57 |
| α | 0.00 | β | 0.00 | γ | 0.00 |

| Direct view optical path | | | | | |
|---|---|---|---|---|---|
| Surface number | Radius of curvature | Plane gap | Eccentricity | Refractive index | Abbe number |
| Object surface | 20.00 | 20.00 | | | |

Direct view optical path

| | | | | | |
|---|---|---|---|---|---|
| 1 | ∞ | 1.00 | | 1.5163 | 64.1 |
| 2 | 2.27 | 2.13 | | | |
| 3 | ERFS[3] | | eccentricity(4) | 1.8348 | 42.7 |
| 4 | ERFS[2] | | eccentricity(3) | | |
| 5 | ∞ | 0.50 | eccentricity(5) | 1.5163 | 64.1 |
| 6 | ∞ (Stop) | | | | |
| 7 | −1.96 | 1.00 | | 1.7292 | 54.7 |
| 8 | −1.54 | 0.10 | | | |
| 9 | 2.41 | 0.30 | | 1.7529 | 27.7 |
| 10 | 1.25 | 1.60 | | 1.6583 | 53.9 |
| 11 | 31.16 | 1.87 | | | |
| 12 | ∞ | 0.40 | | 1.5163 | 64.1 |
| 13 | ∞ | 0.10 | | | |
| Image surface | ∞ | | | | |

ERFS[2]

| | |
|---|---|
| RY | 2.04 |
| θ | 54.52 |
| R | −1.66 |

ERFS[3]

| | |
|---|---|
| RY | 5.71 |
| θ | 18.97 |
| R | −1.86 | eccentricity(3)

| X | 0.00 | Y | 0.00 | Z | 0.96 |
|---|---|---|---|---|---|
| α | 0.00 | β | 0.00 | γ | 0.00 | eccentricity(4)

| X | 0.00 | Y | 0.00 | Z | −0.61 |
|---|---|---|---|---|---|
| α | 0.00 | β | 0.00 | γ | 0.00 | eccentricity(5)

| X | 0.00 | Y | 0.00 | Z | 2.57 |
|---|---|---|---|---|---|
| α | 0.00 | β | 0.00 | γ | 0.00 |

Example 7

Side view optical path

| Surface number | Radius of curvature | Plane gap | Eccentricity | Refractive index | Abbe number |
|---|---|---|---|---|---|
| Object surface | 10.00 | 10.00 | eccentricity(1) | | |
| 1 | ERFS[1] | | eccentricity(2) | 1.8348 | 42.7 |
| 2 | ERFS[2] (RE) | | eccentricity(3) | 1.8348 | 42.7 |
| 3 | ERFS[3] (RE) | | eccentricity(4) | 1.8348 | 42.7 |
| 4 | ERFS[4] | | eccentricity(5) | | |
| 5 | ∞ | 0.50 | eccentricity(6) | 1.5163 | 64.1 |
| 6 | ∞ (Stop) | 0.20 | | | |
| 7 | −2.18 | 1.00 | | 1.7292 | 54.7 |
| 8 | −1.32 | 0.10 | | | |
| 9 | 3.43 | 0.30 | | 1.7063 | 29.9 |
| 10 | 0.91 | 1.60 | | 1.7038 | 48.4 |
| 11 | 21.69 | 1.61 | | | |
| 12 | ∞ | 0.40 | | 1.5163 | 64.1 |
| 13 | ∞ | 0.10 | | | |
| Image surface | ∞ | | | | |

ERFS[1]

| | |
|---|---|
| RY | ∞ |
| θ | 90.00 |
| R | −3.00 |

ERFS[2]

| | |
|---|---|
| RY | 4.75 |
| θ | 50.15 |
| R | −1.72 |

ERFS[3]

| | |
|---|---|
| RY | 5.62 |
| θ | 17.31 |
| R | −1.67 |

ERFS[4]

| | |
|---|---|
| RY | 1.45 |
| θ | 45.27 |
| R | −1.03 | eccentricity(1)

| X | 0.00 | Y | −9.24 | Z | 3.83 |
|---|---|---|---|---|---|
| α | 112.50 | β | 0.00 | γ | 0.00 | eccentricity(2)

| X | 0.00 | Y | 0.00 | Z | 1.24 |
|---|---|---|---|---|---|
| α | 0.00 | β | 0.00 | γ | 0.00 | eccentricity(3)

| X | 0.00 | Y | 0.00 | Z | 0.97 |
|---|---|---|---|---|---|
| α | 0.00 | β | 0.00 | γ | 0.00 | eccentricity(4)

| X | 0.00 | Y | 0.00 | Z | −0.63 |
|---|---|---|---|---|---|
| α | 0.00 | β | 0.00 | γ | 0.00 | eccentricity(5)

| X | 0.00 | Y | 0.00 | Z | 0.24 |
|---|---|---|---|---|---|
| α | 0.00 | β | 0.00 | γ | 0.00 | eccentricity(6)

| X | 0.00 | Y | 0.00 | Z | 1.83 |
|---|---|---|---|---|---|
| α | 0.00 | β | 0.00 | γ | 0.00 |

Direct view optical path

| Surface number | Radius of curvature | Plane gap | Eccentricity | Refractive index | Abbe number |
|---|---|---|---|---|---|
| Object surface | 20.00 | 20.00 | | | |
| 1 | ∞ | 1.00 | | 1.5163 | 64.1 |
| 2 | 3.47 | 2.25 | | | |
| 3 | ERFS[3] | | eccentricity(4) | 1.8348 | 42.7 |
| 4 | ERFS[4] | | eccentricity(5) | | |
| 5 | ∞ | 0.50 | eccentricity(6) | 1.5163 | 64.1 |
| 6 | ∞ (Stop) | 0.20 | | | |
| 7 | −2.18 | 1.00 | | 1.7292 | 54.7 |
| 8 | −1.32 | 0.10 | | | |
| 9 | 3.43 | 0.30 | | 1.7063 | 29.9 |
| 10 | 0.91 | 1.60 | | 1.7038 | 48.4 |
| 11 | 21.69 | 1.61 | | | |
| 12 | ∞ | 0.40 | | 1.5163 | 64.1 |
| 13 | ∞ | 0.10 | | | |
| Image surface | ∞ | | | | |

ERFS[3]

| | |
|---|---|
| RY | 5.62 |
| θ | 17.31 |
| R | −1.67 |

ERFS[4]

| | |
|---|---|
| RY | 1.45 |
| θ | 45.27 |
| R | −1.03 |

-continued

Direct view optical path

| eccentricity(4) | | | | | |
|---|---|---|---|---|---|
| X | 0.00 | Y | 0.00 | Z | −0.63 |
| α | 0.00 | β | 0.00 | γ | 0.00 |
| eccentricity(5) | | | | | |
| X | 0.00 | Y | 0.00 | Z | 0.24 |
| α | 0.00 | β | 0.00 | γ | 0.00 |
| eccentricity(6) | | | | | |
| X | 0.00 | Y | 0.00 | Z | 1.83 |
| α | 0.00 | β | 0.00 | γ | 0.00 |

Example 8

Side view optical path

| Surface number | Radius of curvature | Plane gap | Eccentricity | Refractive index | Abbe number |
|---|---|---|---|---|---|
| Object surface | 10.00 | 10.00 | eccentricity(1) | | |
| 1 | ERFS[1] | | eccentricity(2) | 1.8348 | 42.7 |
| 2 | ERFS[2] (RE) | | eccentricity(3) | 1.8348 | 42.7 |
| 3 | ASS[1] (RE) | | eccentricity(4) | 1.8348 | 42.7 |
| 4 | ASS[2] | | eccentricity(5) | | |
| 5 | ∞ | 0.50 | | 1.5163 | 64.1 |
| 6 | ∞ (Stop) | 0.20 | | | |
| 7 | −2.11 | 1.00 | | 1.7292 | 54.7 |
| 8 | −1.53 | 0.10 | | | |
| 9 | 3.51 | 1.60 | | 1.6204 | 60.3 |
| 10 | −1.30 | 0.50 | | 1.7552 | 27.6 |
| 11 | −2.52 | 2.12 | | | |
| 12 | ∞ | 0.40 | | 1.5163 | 64.1 |
| 13 | ∞ | 0.10 | | | |
| Image surface | ∞ | | | | |

ERFS[1]

| RY | ∞ |
|---|---|
| θ | 90.00 |
| R | −3.00 |

ERFS[2]

| RY | 8.21 |
|---|---|
| θ | 41.24 |
| R | −2.36 |

ASS[1]

| RY | 6.48 |
|---|---|
| k | 0.0000 |

ASS[2]

| RY | 0.80 |
|---|---|
| k | 0.0000 |

| eccentricity(1) | | | | | |
|---|---|---|---|---|---|
| X | 0.00 | Y | −9.24 | Z | 3.83 |
| α | 112.50 | β | 0.00 | γ | 0.00 |
| eccentricity(2) | | | | | |
| X | 0.00 | Y | 0.00 | Z | 1.24 |
| α | 0.00 | β | 0.00 | γ | 0.00 |
| eccentricity(3) | | | | | |
| X | 0.00 | Y | 0.00 | Z | 1.11 |
| α | 0.00 | β | 0.00 | γ | 0.00 |
| eccentricity(4) | | | | | |
| X | 0.00 | Y | 0.00 | Z | −0.72 |

-continued

| α | 0.00 | β | 0.00 | γ | 0.00 |
|---|---|---|---|---|---|
| eccentricity(5) | | | | | |
| X | 0.00 | Y | 0.00 | Z | −0.18 |
| α | 0.00 | β | 0.00 | γ | 0.00 |
| eccentricity(6) | | | | | |
| X | 0.00 | Y | 0.00 | Z | 1.19 |
| α | 0.00 | β | 0.00 | γ | 0.00 |

Direct view optical path

| Surface number | Radius of curvature | Plane gap | Eccentricity | Refractive index | Abbe number |
|---|---|---|---|---|---|
| Object surface | 20.00 | 20.00 | | | |
| 1 | ∞ | 1.00 | | 1.5163 | 64.1 |
| 2 | ∞ | 1.22 | | | |
| 3 | ASS[1] | | eccentricity(4) | 1.8348 | 42.7 |
| 4 | ASS[2] | | eccentricity(5) | | |
| 5 | ∞ | 0.50 | eccentricity(6) | 1.5163 | 64.1 |
| 6 | ∞ (Stop) | 0.20 | | | |
| 7 | −2.11 | 1.00 | | 1.7292 | 54.7 |
| 8 | −1.53 | 0.10 | | | |
| 9 | 3.51 | 1.60 | | 1.6204 | 60.3 |
| 10 | −1.30 | 0.50 | | 1.7552 | 27.6 |
| 11 | −2.52 | 2.12 | | | |
| 12 | ∞ | 0.40 | | 1.5163 | 64.1 |
| 13 | ∞ | 0.10 | | | |
| Image surface | ∞ | | | | |

ASS[1]

| R | 6.48 |
|---|---|
| k | 0.0000 |

ASS[2]

| R | 0.80 |
|---|---|
| k | 0.0000 |

| Eccentricity(4) | | | | | |
|---|---|---|---|---|---|
| X | 0.00 | Y | 0.00 | Z | −0.72 |
| α | 0.00 | β | 0.00 | γ | 0.00 |
| eccentricity(5) | | | | | |
| X | 0.00 | Y | 0.00 | Z | −0.18 |
| α | 0.00 | β | 0.00 | γ | 0.00 |
| eccentricity(6) | | | | | |
| X | 0.00 | Y | 0.00 | Z | 1.19 |
| α | 0.00 | β | 0.00 | γ | 0.00 |

Example 9

Side view optical path

| Surface number | Radius of curvature | Plane gap | Eccentricity | Refractive index | Abbe number |
|---|---|---|---|---|---|
| Object surface | 10.00 | 10.00 | eccentricity(1) | | |
| 1 | ERFS[1] | | eccentricity(2) | 1.8348 | 42.7 |
| 2 | ASS[1] (RE) | | eccentricity(3) | 1.8348 | 42.7 |
| 3 | ASS[2] (RE) | | eccentricity(4) | 1.8348 | 42.7 |
| 4 | ASS[1] | | eccentricity(3) | | |

-continued

Side view optical path

| | | | | | |
|---|---|---|---|---|---|
| 5 | ∞ | 0.50 | eccentricity(5) | 1.5163 | 64.1 |
| 6 | ∞ (Stop) | 2.28 | | | |
| 7 | 7.24 | 1.40 | | 1.7292 | 54.7 |
| 8 | −3.73 | 0.10 | | | |
| 9 | 4.26 | 0.30 | | 1.7479 | 27.9 |
| 10 | 1.56 | 1.80 | | 1.5311 | 66.1 |
| 11 | −9.12 | 2.33 | | | |
| 12 | ∞ | 0.40 | | 1.5163 | 64.1 |
| 13 | ∞ | 0.10 | | | |
| Image surface | ∞ | | | | |

ERFS[1]

| | | |
|---|---|---|
| RY | | ∞ |
| θ | | 90.00 |
| R | | −3.00 |

ASS[1]

| | | |
|---|---|---|
| R | | 2.36 |
| k | | 0.0000 |

ASS[2]

| | | |
|---|---|---|
| R | | 8.35 |
| k | | 0.0000 | eccentricity(1)

| | | | | | | | |
|---|---|---|---|---|---|---|---|
| X | 0.00 | Y | −8.67 | Z | 4.98 | | |
| α | 120.00 | β | 0.00 | γ | 0.00 | | | eccentricity(2)

| | | | | | | |
|---|---|---|---|---|---|---|
| X | 0.00 | Y | 0.00 | Z | 1.71 | |
| α | 0.00 | β | 0.00 | γ | 0.00 | | eccentricity(3)

| | | | | | | |
|---|---|---|---|---|---|---|
| X | 0.00 | Y | 0.00 | Z | 0.42 | |
| α | 0.00 | β | 0.00 | γ | 0.00 | | eccentricity(4)

| | | | | | | |
|---|---|---|---|---|---|---|
| X | 0.00 | Y | 0.00 | Z | −1.45 | |
| α | 0.00 | β | 0.00 | γ | 0.00 | | eccentricity(5)

| | | | | | | |
|---|---|---|---|---|---|---|
| X | 0.00 | Y | 0.00 | Z | 3.18 | |
| α | 0.00 | β | 0.00 | γ | 0.00 | |

Direct view optical path

| Surface number | Radius of curvature | Plane gap | Eccentricity | Refractive index | Abbe number |
|---|---|---|---|---|---|
| Object surface | 20.00 | 20.00 | | | |
| 1 | ∞ | 1.00 | | 1.5163 | 64.1 |
| 2 | 1.98 | 2.16 | | | |
| 3 | ASS[2] | | eccentricity(4) | 1.8348 | 42.7 |
| 4 | ASS[1] | | eccentricity(3) | | |
| 5 | ∞ | 0.50 | eccentricity(5) | 1.5163 | 64.1 |
| 6 | ∞ (Stop) | 2.28 | | | |
| 7 | 7.24 | 1.40 | | 1.7292 | 54.7 |
| 8 | −3.73 | 0.10 | | | |
| 9 | 4.26 | 0.30 | | 1.7479 | 27.9 |
| 10 | 1.56 | 1.80 | | 1.5311 | 66.1 |
| 11 | −9.12 | 2.33 | | | |
| 12 | ∞ | 0.40 | | 1.5163 | 64.1 |
| 13 | ∞ | 0.10 | | | |
| Image surface | ∞ | | | | |

ASS[1]

| | | |
|---|---|---|
| R | | 2.36 |

-continued

Direct view optical path

| | | |
|---|---|---|
| k | | 0.0000 |

ASS[2]

| | | |
|---|---|---|
| R | | 8.35 |
| k | | 0.0000 | eccentricity(3)

| | | | | | | |
|---|---|---|---|---|---|---|
| X | 0.00 | Y | 0.00 | Z | 0.42 | |
| α | 0.00 | β | 0.00 | γ | 0.00 | | eccentricity(4)

| | | | | | | |
|---|---|---|---|---|---|---|
| X | 0.00 | Y | 0.00 | Z | −1.45 | |
| α | 0.00 | β | 0.00 | γ | 0.00 | | eccentricity(5)

| | | | | | | |
|---|---|---|---|---|---|---|
| X | 0.00 | Y | 0.00 | Z | 3.18 | |
| α | 0.00 | β | 0.00 | γ | 0.00 | |

Example 10

Side view optical path

| Surface number | Radius of curvature | Plane gap | Eccentricity | Refractive index | Abbe number |
|---|---|---|---|---|---|
| Object surface | 10.00 | 10.00 | eccentricity(1) | | |
| 1 | ERFS[1] | | eccentricity(2) | 1.8348 | 42.7 |
| 2 | ERFS[2] (RE) | | eccentricity(3) | 1.8348 | 42.7 |
| 3 | ERFS[3] (RE) | | eccentricity(4) | 1.8348 | 42.7 |
| 4 | ERFS[4] | | eccentricity(5) | | |
| 5 | ∞ | 0.50 | eccentricity(6) | 1.5163 | 64.1 |
| 6 | ∞ (Stop) | 0.48 | | | |
| 7 | −19.12 | 1.00 | | 1.7292 | 54.7 |
| 8 | −1.87 | 0.10 | | | |
| 9 | 10.85 | 0.30 | | 1.7552 | 27.6 |
| 10 | 1.03 | 1.60 | | 1.7427 | 44.9 |
| 11 | −8.15 | 1.91 | | | |
| 12 | ∞ | 0.40 | | 1.5163 | 64.1 |
| 13 | ∞ | 0.10 | | | |
| Image surface | ∞ | | | | |

ERFS[1]

| | | |
|---|---|---|
| RY | | ∞ |
| θ | | 90.00 |
| R | | −3.00 |

ERFS[2]

| | | |
|---|---|---|
| RY | | 2.97 |
| θ | | 48.06 |
| R | | −1.96 |

ERFS[3]

| | | |
|---|---|---|
| RY | | 3.99 |
| θ | | 15.59 |
| R | | −1.80 |

ERFS[4]

| | | |
|---|---|---|
| RY | | 1.50 |
| θ | | 50.66 |
| R | | −1.16 | eccentricity(1)

| | | | | | | |
|---|---|---|---|---|---|---|
| X | 0.00 | Y | −9.24 | Z | 3.83 | |
| α | 112.50 | β | 0.00 | γ | 0.00 | | eccentricity(2)

| | | | | |
|---|---|---|---|---|
| X | 0.00 | Y | 0.00 | Z | 1.24 |

-continued

| Side view optical path | | | | | |
|---|---|---|---|---|---|
| α | 0.00 | β | 0.00 | γ | 0.00 |
| eccentricity(3) | | | | | |
| X | 0.00 | Y | 0.00 | Z | 1.02 |
| α | 0.00 | β | 0.00 | γ | 0.00 |
| eccentricity(4) | | | | | |
| X | 0.00 | Y | 0.00 | Z | −0.53 |
| α | 0.00 | β | 0.00 | γ | 0.00 |
| eccentricity(5) | | | | | |
| X | 0.00 | Y | 0.00 | Z | 0.32 |
| α | 0.00 | β | 0.00 | γ | 0.00 |
| eccentricity(6) | | | | | |
| X | 0.00 | Y | 0.00 | Z | 2.49 |
| α | 0.00 | β | 0.00 | γ | 0.00 |

Direct view optical path

| Surface number | Radius of curvature | Plane gap | Eccentricity | Refractive index | Abbe number |
|---|---|---|---|---|---|
| Object surface | 20.00 | 20.00 | | | |
| 1 | ∞ | 1.00 | | 1.5163 | 64.1 |
| 2 | 2.91 | 2.09 | | | |
| 3 | ERFS[5] | | eccentricity(7) | 1.8348 | 42.7 |
| 4 | ERFS[4] | | eccentricity(5) | | |
| 5 | ∞ | 0.50 | eccentricity(6) | 1.5163 | 64.1 |
| 6 | ∞ (Stop) | 0.48 | | | |
| 7 | −19.12 | 1.00 | | 1.7292 | 54.7 |
| 8 | −1.87 | 0.10 | | | |
| 9 | 10.85 | 0.30 | | 1.7552 | 27.6 |
| 10 | 1.03 | 1.60 | | 1.7427 | 44.9 |
| 11 | −8.15 | 1.91 | | | |
| 12 | ∞ | 0.40 | | 1.5163 | 64.1 |
| 13 | ∞ | 0.10 | | | |
| Image surface | ∞ | | | | |

| ERFS[4] | |
|---|---|
| RY | 1.50 |
| θ | 50.66 |
| R | −1.16 |

| ERFS[5] | |
|---|---|
| RY | 4.09 |
| θ | 7.31 |
| R | −0.52 |

| eccentricity[5] | | | | | |
|---|---|---|---|---|---|
| X | 0.00 | Y | 0.00 | Z | 0.32 |
| α | 0.00 | β | 0.00 | γ | 0.00 |
| eccentricity[6] | | | | | |
| X | 0.00 | Y | 0.00 | Z | 2.49 |
| α | 0.00 | β | 0.00 | γ | 0.00 |
| eccentricity[7] | | | | | |
| X | 0.00 | Y | 0.00 | Z | −0.74 |
| α | 0.00 | β | 0.00 | γ | 0.00 |

Examples 6 through 10 represent the following values for d1, d2 and d1/d2, where d1 is the distance from the aperture to the position where the central principal ray of light strikes the side view first reflective surface 22 as observed in the direction of the axis of rotational symmetry, the object side being the positive side, and d2 is the distance from the aperture to the position where the central principal ray of light strikes the side view second reflective surface 23.

| | Example 6 | Example 7 | Example 8 | Example 9 | Example 10 |
|---|---|---|---|---|---|
| d1 | 2.11 | 1.36 | 0.59 | 3.26 | 1.96 |
| d2 | 3.68 | 2.96 | 2.41 | 2.23 | 3.51 |
| d1/d2 | 0.62 | 0.46 | 0.25 | 1.46 | 0.55 |

Additionally and preferably, the following relationship holds true.

$$d1 > 0 \qquad (3)$$

The above conditional inequality indicates that the side view first reflective surface 22 is arranged between the aperture and the side view second reflective surface 23. Particularly, it provides the condition to be satisfied for positioning it at an optimal position where it hardly gives rise to interference with the optical system of the back group Gb.

More preferably, the condition depicted below is satisfied.

$$d1/d2 > 0 \qquad (4)$$

The optical system can be made compact when the above condition is satisfied. The angle of reflection of the second reflective surface becomes too large when the upper limit is exceeded. Then, the external dimension becomes too large and the eccentric aberration produced at the second reflective surface can no longer be corrected by other surfaces.

While each of the transmissive surfaces and the reflective surfaces of the transparent medium that is concentric with the central axis 2 of the optical system 1 and has a refractive index greater than 1 is designed as an extended rotary free curved surface in each of the above describe examples, an extended rotary free curved surface is equivalent to a spherical surface when the extended rotary free curved surface is orthogonal to a rotationally symmetric surface and does not involve any term of higher degree.

While each of the reflective surfaces and the refractive surfaces of the front group Gf is designed as an extended rotary free curved surface that is formed by rotating a line segment of an arbitrary shape around the axis of rotational symmetry 1 and does not have the surface vertex on the axis of rotational symmetry 1, it may be replaced by an arbitrary curved surface.

Additionally, in an optical system according to the present invention, the inclination of the image plane 5 that arises due to eccentricity and the pupil aberration that arises when the stop is back-projected are corrected by using a formula that involves one or more than one odd-number-th degree terms for the formula for defining a line segment of an arbitrary shape for forming a rotationally symmetric surface.

An image with an omni-directional view angle of 360° can be picked up and projected by using a transparent medium that is rotationally symmetric around the central axis 2 of the front group Gf for the purpose of the present invention. However, an image with a view angle of 180°, 120°, 240° or some other angle may be picked up or projected by cutting the transparent medium along a cross section that includes the central axis 2 to a half, one-third, two-third or the like.

An optical system according to the present invention is described above as an image pickup or observation optical system that can obtain an image with an omni-directional (all-around) view angle of 360° including the vertex and the central axis (the axis of rotational symmetry) 1 vertically directed, the present invention is not limited to image pickup optical systems and observation optical systems and an optical system according to the present invention can be used as a projection optical system for projecting an image with an omni-directional (all-around) view angle of 360° including the vertex where the optical path is followed reversely. Furthermore, an optical system according to the present invention can be used as an omni-directional optical system of an endoscope or an intra-canal observation apparatus.

Figure 34:
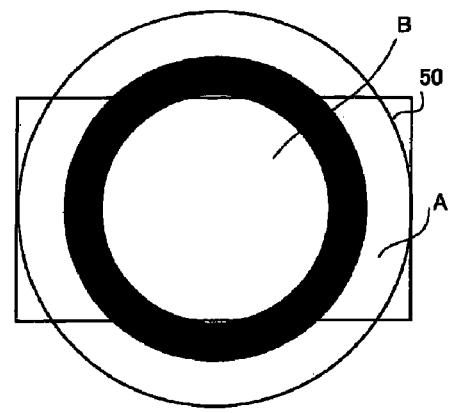
FIG. 34 is a schematic illustration of an exemplar positional arrangement of an image of an optical system according to the present invention and an imaging element.
Figure 34:
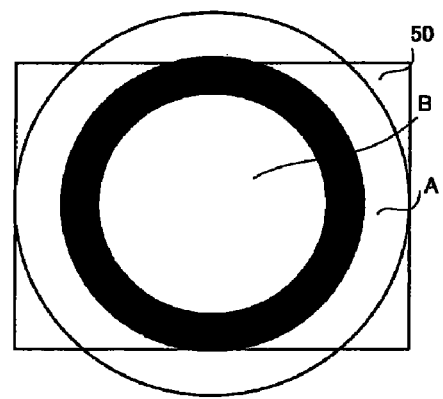
Figure 34:
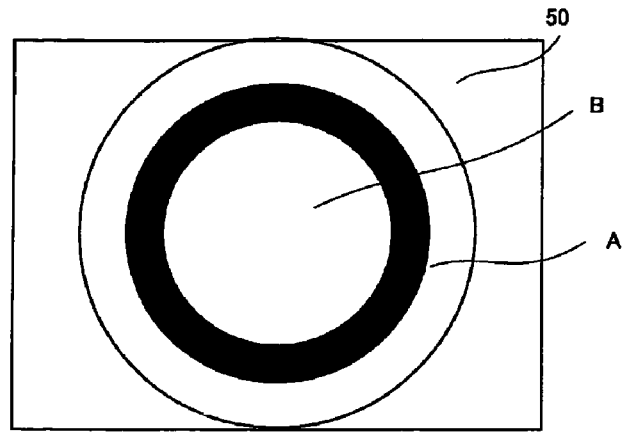

FIG. 34 is a schematic illustration of an exemplar positional arrangement of an image of an optical system according to the present invention and an imaging element. In FIG. 34, (a) is an example of using an imaging element with an aspect ratio of 16:9. When no vertically long image is used, the dimension of the imaging element 50 is preferably made equal to the distance between the left margin and the right margin of the image A1 of the side view optical path A. In FIG. 34, (b) is an example of using an imaging element 50 with an aspect ratio of 4:3 and making the dimension of the imaging element 50 agree with that of the image B1 of the direct view optical path B in a situation where no vertically long image is used as in (a) of FIG. 34. In FIG. 34, (c) is an example of using an imaging element 50 with an aspect ratio of 4:3 and making the dimension of the imaging element 50 agree with that of the image A1 of the side view optical path A. With this arrangement, both the image A1 of the side view optical path A and the image B1 of the direct view optical path B can be entirely picked up.

Figure 35:
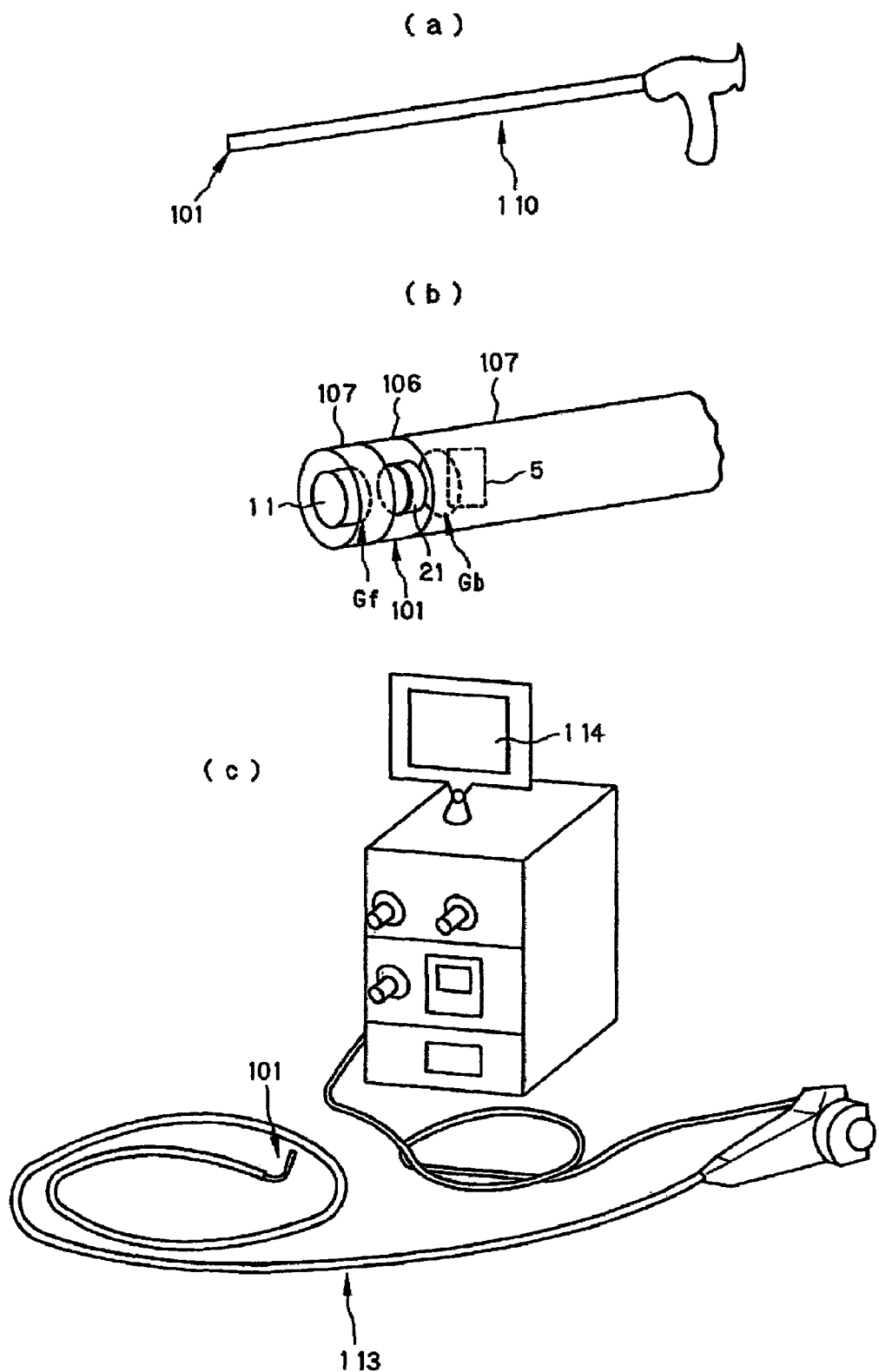
FIG. 35 is a schematic illustration of an example of using an optical system according to the present invention as an image pickup optical system at the front end of an endoscope.

Now, examples of using an image pickup optical system 101 and those of using a projection optical system 102 will be described below as applications of an optical system 1 according to the present invention. FIG. 35 is a schematic illustration of an example of using an image pickup optical system 101 according to the present invention as an image pickup optical system at the front end of an endoscope. In FIG. 35, (a) illustrates an example of mounting an image pickup optical system according to the invention to the front end 101 of a rigid endoscope 110 and picking up and observing a 360° omni-directional image and (b) schematically illustrates the configuration of the front end thereof. A flare stop 107 that is formed by a casing having a peripherally extending slit-like aperture 106 is arranged at the incident surface 21 of the front group Gf of a panoramic image pickup optical system 101 according to the present invention in order to prevent flare from entering. In FIG. 35, (c) illustrates an example of similarly mounting a panoramic image pickup optical system 101 according to the invention to the front end of a soft electronic endoscope 113 and displaying a picked up image on a display apparatus 114 after subjecting it to image processing.

Figure 36:
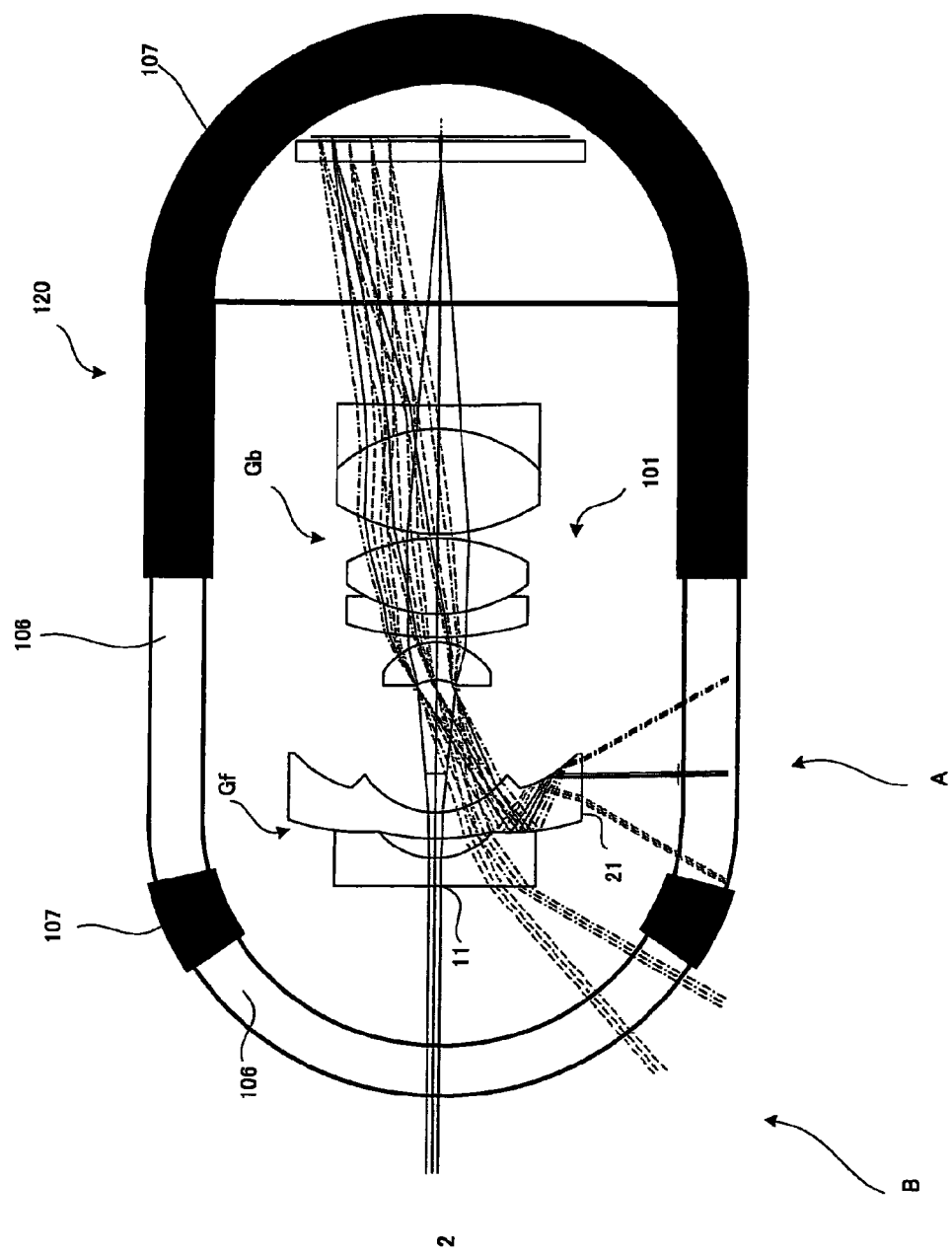
FIG. 36 is a schematic illustration of an example of using the optical system of Example 1 of the present invention as an image pickup optical system of a capsule endoscope.
Figure 37:
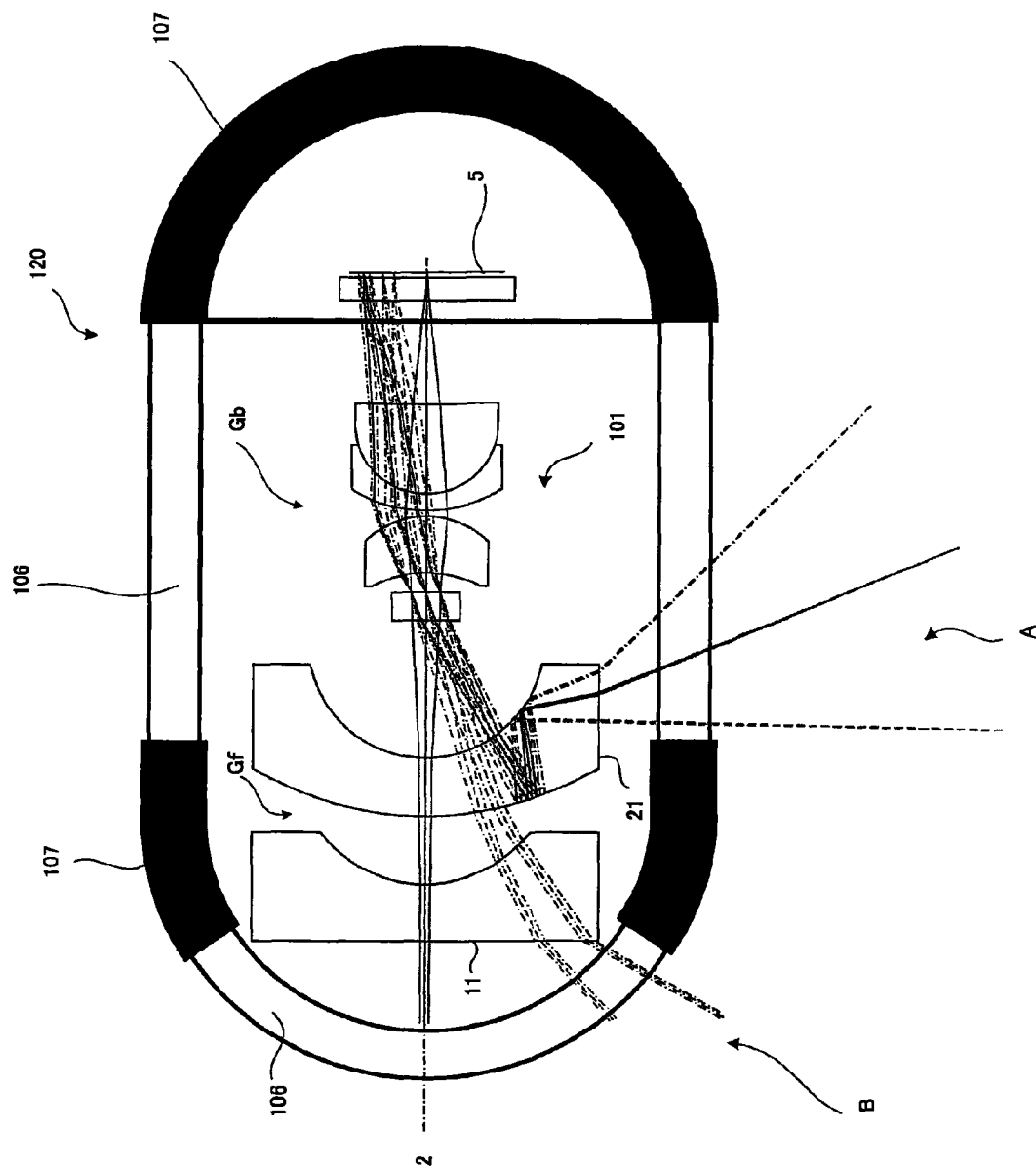
FIG. 37 is a schematic illustration of an example of using the optical system of Example 6 of the present invention as an image pickup optical system of a capsule endoscope.

FIGS. 36 and 37 are schematic illustrations of examples of mounting an image pickup optical system 101 according to the present invention to a capsule endoscope 120 and picking up and observing a 360° omni-directional image. A flare stop 107 is formed at a casing having a peripherally extending slit-like aperture 106 around the side view first transmissive surface 21 of the second group of the front group Gf at the side view optical path A of an image pickup optical system 101 as well as a flare stop 107 is formed at a casing having a peripherally extending circular aperture 106 in front of the direct view first transmissive surface 11 of the first group of the front group Gf at the direct view optical path B of an image pickup optical system 101 according to the present invention in order to prevent flare from entering.

As illustrated in FIGS. 35, 36 and 37, an image of any of various parts can be picked up for observation from behind an image pickup optical system 101 according to the present invention when it is applied to an endoscope so that the part can be shot from various angles in order to pick up images therefore for the purpose of observation, although no such images can be picked up according to the conventional art.

Figure 38:
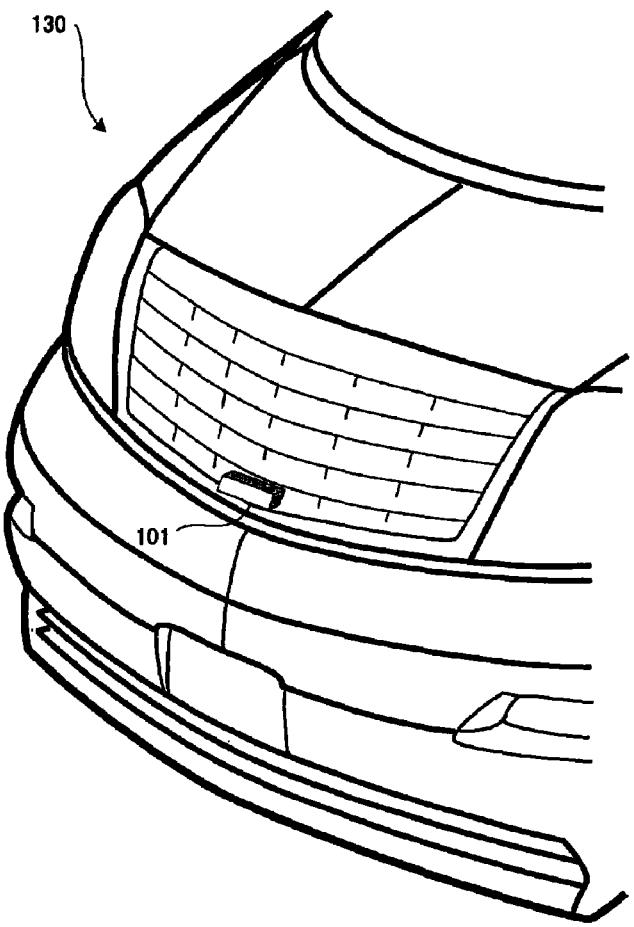
FIG. 38 is a schematic illustration of examples of using an optical system according to the present invention as an image pickup optical system of an automobile.
Figure 38:
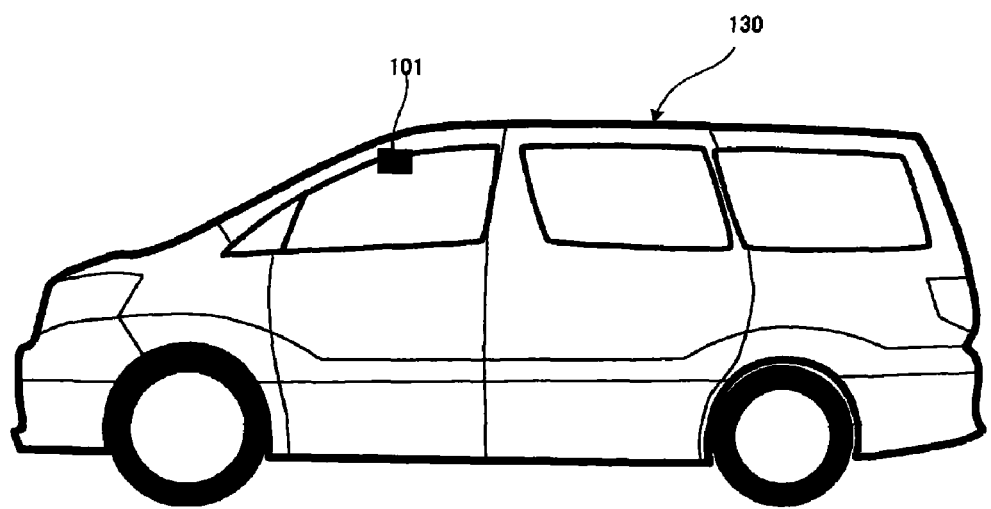

In FIG. 38, (a) illustrates an example of fitting an image pickup optical system 101 according to the present invention to the front side of an automobile 130, processing the images picked up by each of the image pickup optical systems 101 fitted to the automobile including the above-described one to correct distortions and displaying the images simultaneously. In FIG. 38, (b) illustrates an example of fitting a plurality of image pickup optical systems 101 according to the present invention respectively to various parts of an automobile 130 including corners and the top of the pole at the head of the automobile 130, processing the images picked up by each of the image pickup optical systems 101 to correct distortions and displaying the images simultaneously. The dimension of each of the imaging elements 50 is preferably made equal to the distance between the left margin and the right margin of the image A1 of the corresponding side view optical path A as described above by referring to (a) of FIG. 34 to obtain a horizontally broad view.

Figure 39:
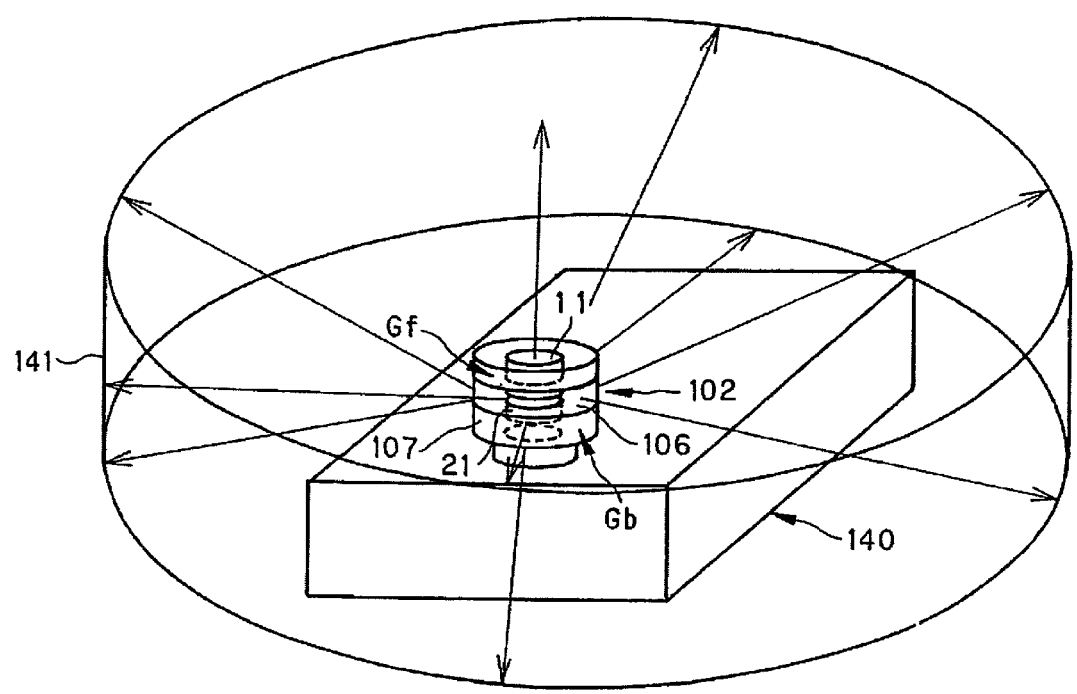
FIG. 39 is a schematic illustration of an example of using an optical system according to the present invention as a projection optical system of a projection apparatus.

FIG. 39 is a schematic illustration of an example of using a projection optical system 102 according to the present invention as a projection optical system of a projection apparatus 140. The picked up panoramic image is displayed on a display element arranged on the image plane 5 of the optical system and then a 360° omni-directional image is projected and displayed on a screen 141 arranged 360° omni-directionally by way of a projection optical system 102.

Figure 40:
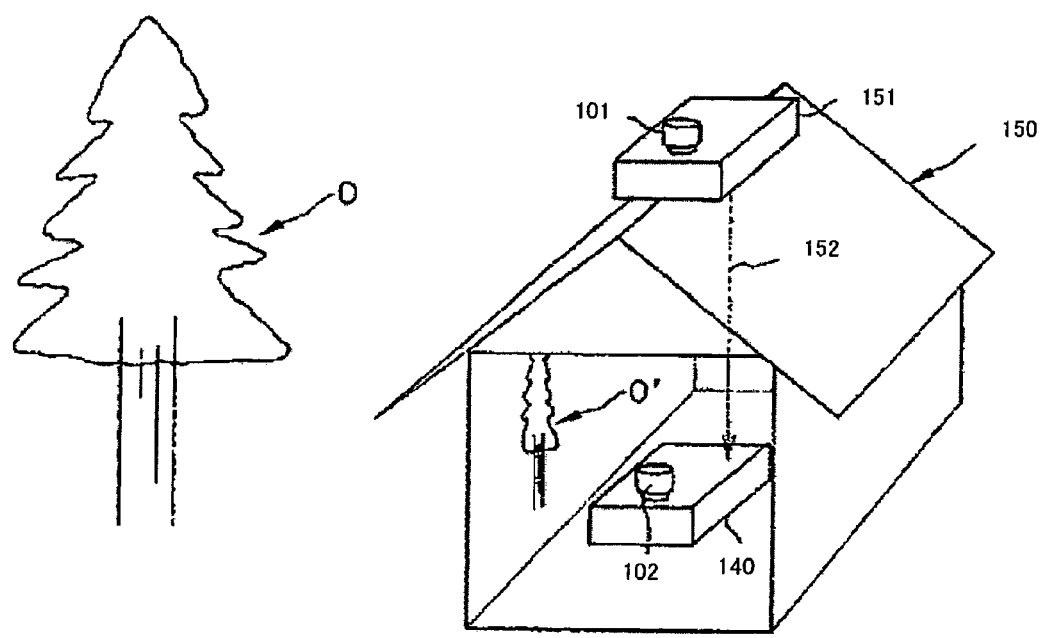
FIG. 40 is a schematic illustration of an example of using an optical system according to the present invention as an image pickup optical system for picking up an image of an outdoor object.

In the example of FIG. 40, an image pickup apparatus 151 including an image pickup optical system 101 according to the present invention is arranged at the outside of a building 150, while a projection apparatus 140 including another image pickup optical system 101 according to the present invention is arranged in the inside of the building and connected to the image pickup apparatus 151, and the image picked up by the image pickup apparatus 151 is sent to the projection apparatus 140 by way of an electric wire 152. An 360° omni-directional image of an outdoor object O is picked up by the image pickup apparatus 151 by way of the image pickup optical system 101 and the video signal of the picked up image is sent to the projection apparatus 140 by way of the electric wire 152 so that the image is displayed on the display element arranged on the image plane and then an enlarged image 0' of the object O is projected and displayed on a wall in the building by way of the projection optical system 102.

The invention claimed is:

1. An optical element rotationally symmetric around a central axis and formed by a transparent medium having a refractive index greater than 1, wherein:
the transparent medium includes:
a first transmissive surface, a first reflective surface arranged at the central axis side relative to the first transmissive surface,
a second reflective surface arranged at the far side to the image plane relative to the first reflective surface, a second transmissive surface arranged at the image plane side relative to the second reflective surface, and
a third transmissive surface and a fourth transmissive surface arranged at the image plane side relative to the third transmissive surface; and
a flux of light entering the transparent medium has a side view optical path and a direct view optical path therein and goes into the transparent medium to proceed along the side view optical path by way of the first transmissive surface so as to be reflected to the side opposite to the image plane by the first reflective surface and then to the image plane side by the second reflective surface to form an optical path before going out from the transparent medium to the outside at the image plane side by way of the second transmissive surface in the order of forward ray tracing and also along the direct view optical path by way of the third transmissive surface to form another optical path before going out from the transparent medium into the outside at the image plane side by way of the fourth transmissive surface also as viewed in the order of forward ray tracing.

2. The optical element according to claim 1, wherein the side view optical path is formed a substantially Z-shaped optical path.

3. The optical element according to claim 1, wherein the side view optical path is formed only at a side relative to the central axis.

4. The optical element according to claim 1, wherein the second transmissive surface is arranged in the vicinity of the central axis and the first reflective surface and the second reflective surface are arranged in a peripheral part thereof, while the first transmissive surface is arranged in the outermost peripheral part thereof.

5. The optical element according to claim 1, wherein the first reflective surface is a surface arranged at a position same as that of and having a shape same as that of the second transmissive surface.

6. The optical element according to claim 1, wherein the first reflective surface is a surface arranged at a position same as that of and having a shape same as that of the fourth transmissive surface.

7. The optical element according to claim 1, wherein the second reflective surface is a surface arranged at a position same as that of and having a shape same as that of the third transmissive surface.

8. The optical element according to claim 1, wherein the first reflective surface and the second reflective surface have a total reflection effect.

9. The optical element according to claim 1, wherein the first transmissive surface is a cylindrical or conical surface.

10. The optical element according to claim 1, wherein at least either the first reflective surface and the second reflective surface is formed by an extended rotary free curved surface formed by rotating a line segment of arbitrary shape having no plane of symmetry around the central axis.

11. The optical element according to claim 1, wherein at least one of the surfaces that the transparent medium has is formed by an extended rotary free curved surface formed by rotating a line segment of arbitrary shape including one or more than one odd-number-th degree terms.

12. An optical system wherein it includes a front group, a back group arranged at the side of the image plane relative to the front group and an aperture arranged between the front group and the back group and that optical elements according to claim 1 are arranged in the front group and the direct view optical path picks up or projects an image of an object point in the vicinity of the central axis while the side view optical path picks up or projects an image of an object point on the periphery of the central axis.

13. The optical system according to claim 12, wherein the side view optical path and the direct view optical path share part of the optical elements for use and an circular image of the direct view optical path and an annular image of the side view optical path on the outer periphery thereof are formed on the same plane.

14. The optical system according to claim 12, wherein the second reflective surface is arranged with its concave surface directed to the aperture.

15. The optical system according to claim 12, wherein the first reflective surface is arranged with its concave surface directed to the aperture.

16. The optical system according to claim 12, wherein the image of the side view optical path does not form any intermediate image on the optical path.

17. The optical system according to claim 12, wherein it satisfies the condition of $$D<10 \text{ mm} \tag{1},$$

where D is the external dimension of the optical element.

18. The optical system according to claim 12, wherein it satisfies the condition of $$D/Dr<2 \tag{2},$$

where Dr is the external dimension of the image of the side view optical path.

19. An endoscope formed by using an optical system according to claim 12.

20. An optical system comprising:
a front group having negative power and which is rotationally symmetric around a central axis, an aperture and a back group having positive power;
wherein the optical system forms or projects an image without forming an intermediate image on any optical path, and
the front group has an effect of synthetically combining a direct view optical path for forming or projecting an image on the central axis by a transmission effect and a side view optical path for forming or projecting an omnidirectional image in a direction substantially orthogonal to the central axis by a reflection effect;
a transparent medium including:
a first transmissive surface, a first reflective surface arranged at the central axis side relative to the first transmissive surface,
a second reflective surface arranged at the far side to the image plane relative to the first reflective surface, a second transmissive surface arranged at the image plane side relative to the second reflective surface, and
a third transmissive surface and a fourth transmissive surface arranged at the image plane side relative to the third transmissive surface; and
wherein a flux of light entering the front group goes into the transparent medium by way of the first transmissive surface to proceed along the side view optical path so as to be reflected to the side opposite to the image plane by the first reflective surface and then to the image plane side by the second reflective surface to form an optical path before going out from the transparent medium to the outside at the image plane side by way of the second transmissive surface in the order of forward ray tracing and also along the direct view optical path by way of the third transmissive surface before going out from the transparent medium into the outside at the image plane side by way of the fourth transmissive surface also as viewed in the order of forward ray tracing, and
if a ray of light passing through the center of the aperture is referred to as a central principal ray of light, the central principal ray of light striking the first transmissive surface is inclined toward the image plane side relative to a line orthogonal to the central axis.

21. The optical system according to claim 20, wherein the side view optical path is formed a substantially Z-shaped optical path.

22. The optical system according to claim 20, wherein the first reflective surface and the second reflective surface are arranged with their concave surfaces directed to the aperture and, if the center of the view angle of the meridional cross section of an omni-directional image is referred to as the central view angle and the ray of light passing through the center of the aperture is referred to as a central principal ray of light, the position at which the central principal ray of light strikes the first reflective surface is located at the side opposite to the image plane relative to the aperture.

23. The optical system according to claim 20, wherein the first reflective surface has a total reflection effect.

24. The optical system according to claim 20, wherein a transmissive surface is arranged at the side opposite to the image plane relative to the first reflective surface.

25. The optical system according to claim 20, wherein the first reflective surface and the second transmissive surface are formed at the same position with the same surface shape.

26. The optical system according to claim 20, wherein the first reflective surface and the fourth transmissive surface are formed at the same position with the same surface shape.

27. The optical system according to claim 20, wherein the second reflective surface and the third transmissive surface are formed at the same position with the same surface shape.

28. The optical system according to claim 20, wherein the optical path from the first reflective surface to the second reflective surface is in a direction divergent relative to the central axis.

29. The optical system according to claim 20, wherein the first transmissive surface is a cylindrical or conical surface.

30. The optical system according to claim 20, wherein at least one of the surfaces that the front group has is formed by an extended rotary free curved surface formed by rotating a line segment of arbitrary shape having no plane of symmetry around the central axis.

31. The optical system according to claim 20, wherein at least one of the surfaces that the front group has is formed by a rotary free curved surface formed by rotating a line segment of arbitrary shape including one or more than one odd-number-th degree terms.

32. An endoscope formed by using an optical system according to claim 20.

* * * * *